US010314888B2

(12) United States Patent
Gold et al.

(10) Patent No.: US 10,314,888 B2
(45) Date of Patent: Jun. 11, 2019

(54) THERAPEUTIC AND COSMETIC USES AND APPLICATIONS OF CALRETICULIN

(71) Applicant: NEW YORK UNIVERSITY, New York, NY (US)

(72) Inventors: Leslie I. Gold, New York, NY (US); Marek Michalak, Edmonton (CA)

(73) Assignee: New York University, New York, NY (US)

(*) Notice: Subject to any disclaimer, the term of this patent is extended or adjusted under 35 U.S.C. 154(b) by 0 days.

(21) Appl. No.: 15/004,372

(22) Filed: Jan. 22, 2016

(65) Prior Publication Data

US 2016/0354438 A1 Dec. 8, 2016

Related U.S. Application Data

(62) Division of application No. 13/717,349, filed as application No. PCT/US2011/040979 on Jun. 17, 2011, now Pat. No. 9,254,310.

(60) Provisional application No. 61/355,987, filed on Jun. 17, 2010.

(51) Int. Cl.

| | |
|---|---|
| ***A61K 38/17*** | (2006.01) |
| ***A61K 8/64*** | (2006.01) |
| ***A61K 8/73*** | (2006.01) |
| ***A61Q 19/08*** | (2006.01) |
| ***A61Q 7/00*** | (2006.01) |
| ***A61K 8/02*** | (2006.01) |

(52) U.S. Cl.

CPC ........ *A61K 38/1738* (2013.01); *A61K 8/0208* (2013.01); *A61K 8/64* (2013.01); *A61K 8/735* (2013.01); *A61Q 7/00* (2013.01); *A61Q 19/08* (2013.01); *A61K 2800/91* (2013.01)

(58) Field of Classification Search

CPC ............ A61K 2800/91; A61K 38/1738; A61K 8/0208; A61K 8/64; A61K 8/735

See application file for complete search history.

(56) References Cited

U.S. PATENT DOCUMENTS

| | | | |
|---|---|---|---|
| 3,691,016 | A | 9/1972 | Patel |
| 3,969,287 | A | 7/1976 | Jaworek et al. |
| 4,195,128 | A | 3/1980 | Hildebrand et al. |
| 4,229,537 | A | 10/1980 | Hodgins et al. |
| 4,247,642 | A | 1/1981 | Hirohara et al. |
| 4,330,440 | A | 5/1982 | Ayers et al. |
| 5,591,716 | A | 1/1997 | Siebert et al. |
| 6,171,864 | B1 | 1/2001 | Coughlan et al. |
| 7,351,745 | B2 | 4/2008 | Dryer et al. |
| 7,491,709 | B2 | 2/2009 | Carey |
| 7,514,092 | B2 | 4/2009 | Dryer et al. |
| 7,709,017 | B2 | 5/2010 | Tayot |
| 8,323,648 | B2 | 12/2012 | Roos et al. |
| 8,440,629 | B2 | 5/2013 | Starr et al. |
| 8,470,307 | B2 | 6/2013 | Frankel |
| 8,747,833 | B2 | 6/2014 | Chen et al. |
| 2004/0137009 | A1 | 7/2004 | Kojima et al. |
| 2005/0171016 | A1 | 8/2005 | Streit et al. |
| 2008/0045909 | A1 | 2/2008 | Fossel |
| 2010/0048484 | A1 | 2/2010 | Gold |
| 2010/0158930 | A1 | 6/2010 | Zhu et al. |
| 2010/0196517 | A1 | 8/2010 | Fossel |
| 2013/0045918 | A1 | 2/2013 | Gold et al. |
| 2013/0085096 | A1 | 4/2013 | Pepicelli et al. |
| 2016/0310563 | A1 | 10/2016 | Gold et al. |

FOREIGN PATENT DOCUMENTS

| | | |
|---|---|---|
| EP | 75444 | 3/1983 |
| WO | 1996/028469 A1 | 9/1996 |
| WO | 2008015249 | 2/2008 |

OTHER PUBLICATIONS

Lillian B. Nanney, Calreticulin Enhances Porcine Wound Repair by Diverse Biological Effects, The American Journal of Pathology, vol. 173, No. 3, Sep. 2008.*

Christopher B. Ballas, Delayed wound healing in aged rats is associated with increased collagen gel remodeling and contraction by skin fibroblasts, not with differences in apoptotic or myofibroblast cell populations, Wound Rep Reg 2001;9:223-237.*

Medscape, Amiriak, Skin Anatomy, Epidermal Appednages, Nov. 29, 2017.*

International Preliminary Report on Patentability Issued in PCT/US2009/054922 dated Mar. 1, 2011, 4 pages.

Leach, Michael R. et al., "Localization of the Lectin, ERp57 Binding, and Polypeptide Binding Sites of Calnexin Calreticulin", The Journal of Biological Chemistry (2002), vol. 277, No. 3., pp. 29686-29697.

Written Opinion of the International Search Authority Issued in PCT/US2009/054922 dated Mar. 12, 2010, 3 pages.

Wollenberg, Michael S. et al., "Signal Sequence Cleavage of Peptidyl-tRNA Prior to Release from the Ribosome and Translocon", The Journal of Biological Chemistry (2004), vol. 279, No. 24, pp. 24919-24922.

Wang et al., "Nitric Oxide Donors: For Pharmaceutical and Biological Applications", Wiley-VCH Verlag GmbH & Co. KGaA (2005), 49 pages.

Acosta et al., Epidermal growth factor intralesional infiltrations can prevent amputation in patients with advanced diabetic foot wounds, Int Wound Journal, vol. 3, pp. 232-239, 2006.

Adelman et al., In Vitro Deletional Mutagenesis for Bacterial Production of the 20,000-Dalton Form of Human Pituitary Growth Hormone, DNA, vol. 2, pp. 183-193, 1983.

(Continued)

*Primary Examiner* — James H Alstrum-Acevedo
*Assistant Examiner* — Erinne R Dabkowski
(74) *Attorney, Agent, or Firm* — Troutman Sanders LLP

(57) ABSTRACT

The invention relates to therapeutic and cosmetic uses of calreticulin including reducing or eliminating wrinkles and/or fine lines, tissue repair and reconstruction, repairing damaged bone and/or cartilage, stimulating regeneration of an epidermal appendage, enhancing phagocytosis of bacteria by phagocytes within a wound, treating a wound in a patient suffering from delayed wound healing, treating a corneal wound, and treating or preventing a surgical adhesion.

3 Claims, 43 Drawing Sheets

Specification includes a Sequence Listing.

(56) References Cited

OTHER PUBLICATIONS

Albert et al., Cost effective management of recalcitrant diabetic foot ulcers, Clin Podiatr Med Surg, vol. 19, pp. 483-491, 2002.
Baksh et al., Expression and Purification of Recombinant and Native Calreticulin, Prot Express Purific., vol. 3, pp. 322-331, 1992.
Baksh et al., Expression of Calreticulin in *Escherichia coli* and identification of its CA2+ binding domains, J Biol Chem, vol. 266, pp. 21458-21465, 1991.
Ballas et al., Delayed wound healing in aged rats is associated with increased collagen gel remodeling and contraction by skin fibroblasts, not with differences in apoptotic or myofibroblast cell populations, Wound Repair Regen., vol. 9, pp. 223-237, 2001.
Bandyopadhyay et al., A 'traffic control' role for TGFb3: orchestrating dermal and epidermal cell motility during wound healing, J Cell Biol., vol. 172, pp. 1093-1105, 2006.
Bedard et al.. Cellular Functions of Endoplasmic Reticulum Chaperones Calreticulin, Calnexin, and ERp57, International Review of Cytology, vol. 245, pp. 91-121, 2005.
Brem et al., Cellular and molecular basis of wound healing in diabetes, J. Clin. Invest., vol. 117, pp. 1219-1222, 2007.
Clark et al., Tissue Engineering for Cutaneous Wounds, J Invest. Dermatol., vol. 127, pp. 1018-1029, 2007.
Deveci et al., Glutathione enhances fibroblast collagen contraction and protects keratinocytes from apoptosis in hyperglycaemic culture, British J of Dermatology, vol. 152, pp. 217-224, 2005.
Ellis et al., Motogenic and Biosynthetic response of adult skin fibroblasts to TGF-Beta Isoforms (-1, -2 and -3) determined by 'tissue response unit' role of cell density and substratum, Cell Biology International, vol. 23, pp. 593-602, 1999.
Embil et al., Recombinant human platelet-derived growth factor-BB (becaplermin) for healing chronic lower extremity diabetic ulcers: an open-label clinical evaluation of efficacy, Wound Repair Regen, vol. 8, pp. 162-168, 2000.
Fliegel et al., Molecular Cloning of the High Affinity Calcium-binding Protein Calreticulin of Skeletal Muscle Sarcoplasmic Reticulum, J Biol Chem, vol. 264, pp. 21522-21528, 1989.
Gailit et al., Wound repair in the context of extracellular matrix, Curr Opin Cell Biol, vol. 6, pp. 717-725, 1994.
Galiano et al., Topical Vascular Endothelial Growth Factor Accelerates Diabetic Wound Healing through Increased Angiogenesis and by mobilizing and recruiting bone marrow-derived cells, Am J Pathol., vol. 164, pp. 1935-1947, 2004.
Galiano, et al., Quantitative and reproducible murine model of excisional wound healing, Wound Repair and Regeneration, vol. 12, pp. 485-492, 2004.
Gardai et al., Cell-Surface Calreticulin Initiates Clearance of Viable or Apoptotic Cells through trans-Activation of LRP on the Phagocte, Cell, vol. 123, pp. 321-334 , 2005.
Gold et al., Overview of the Role for Calreticulin in the Enhancement of wound healing through multiple biological effects, J Investing. Dermatol. Symp. Proc., vol. 11 , pp. 57-65, 2006.
Gold, et al., Calreticulin: non-endoplasmic reticulum functions in physiology and disease, The FASEB Journal, vol. 24, pp. 665-683, 2010.
Greenhalgh et al., PDGF and FGF Stimulate Wound Healing in the Genetically Diabetic Mouse, Am J Pathol, vol. 136, pp. 1235-1246, 1990.
Guo et al., Identification of an N-domain histidine essential for chaperone function in calreticulin, J Biol Chem, vol. 278, pp. 50645-50653, 2003.
Huang et al., The role of tyrosine phosphorylation of cortactin in the locomotion of endothelial cells, J Biol Chem, vol. 273, pp. 25770-25776, 1998.
International Search Report for Int. Patent Appl. No. PCT/US11/40979, dated Feb. 3, 2012.
Ito, et al., Wnt-dependent de novo hair follicle regeneration in adult mouse skin after wounding, Nature, vol. 447, pp. 316-321, 2007.
Jasny et al., Insect viruses invade biotechnology, Science, vol. 238, p. 1653, 1987.
Johnson et al., The ins and outs of calreticulin: from the ER lumen to the extracellular space, Trends Cell Biol., vol. 11, pp. 122-129, 2001.
Kinbara et al., Transforming Growth Factor-b Isoforms Differently Stimulate Proa 2 (I) Collegen Gene Expression During Wound Healing Process in Transgenic Mice, J Cell Physiol, vol. 190, pp. 375-381, 2002.
Ksander et al., Transforming Growth Factors-b and b2 Enhance Connective Tissue Formation in Animal Models of Dermal Wound healing by Second Intent, Ann NY Acad Sci, vol. 593, pp. 135-147, 1990.
Lampugnani et al., Cell Migration into a wounded area in vitro, Methods Mol Biol., pp. 177-182, 1999.
Leibovich et al., The Role of the Macrophage in Wound Repair, Am J Pathol, vol. 78, pp. 71-100, 1975.
Lerman et al., Cellular Dysfunction in the Diabetic Fibroblast, Am J Pathol, vol. 162, pp. 303-312, 2003.
Levine et al., Spatial and Temporal Patterns of Immunoreactive Transforming Growth Factor b1, b2, and b3 during excisional wound repair, Amer J Pathol., vol. 143, pp. 368-380, 1993.
Li et al., Transforming growth factor-b3 affects plasminogen activator inhibitor-1 expression in fetal mice and modulates fibroblast-mediated collagen gel contraction, Wound Repair Regen, vol. 14, pp. 516-525, 2006.
Loots et al., Cultured fibroblasts from chronic diabetic wounds on the lower extremity (non-insulin-dependent diabetes mellitus) show disturbed proliferation, Archives of Dermatological Research, vol. 291, pp. 93-99, 1999.
McCauliffe et al., A Human Ro/SS-A Autoanigen Is the Homologue of Calreticulin and is highly homologous with onchocercal RAL-1 antigen and an aplysia Memory Molecule J Clin Invest, vol. 86, p. 332, 1990.
McMullen et al., Spatial and temporal expression of transforming growth factor-beta isoforms during ovine excisional and incisional wound repair, Wound Repair Regen, vol. 3, pp. 141-156, 1995.
Meier et al., Emerging new drugs for scar reduction, Expert Opin Emerg Drugs, vol. 11, pp. 23-37, 2006.
Meier et al., Emerging new drugs for wound repair, Expert Opinion Emerg Drugs, vol. 11, pp. 39-47, 2006.
Michaels et al., Topical vascular endothelial growth factor reverses delayed wound healing secondary to angiogenesis inhibitor administration, Wound Repair and Regeneration vol. 13, pp. 506-512, 2005.
Michalak et al., Calreticulin Biochem J, vol. 285, pp. 681-692, 1992.
Michalak et al., Calreticulin: one protein, one gene, many functions, Biochem J, vol. 344, pt 2, pp. 281-292, 1999.
Nanney et al., Calreticulin Enhances Porcine Wound Repair by Diverse Biological Effects, Am J Pathol, vol. 173, pp. 610-630, 2008.
Obara et al., Acceleration of wound healing in healing-impaired db/db mice with a photocrosslinkable chitosan hydrogel containing fibroblast growth factor-2, Wound Repair and Regeneration, vol. 13, pp. 390-397, 2005.
Obeid et al.. Calreticulin exposure dictates the immunogenicity of cancer cell death, Nature Medicine, vol. 13, pp. 54-61, 2007.
Ogawa et al., Differences in the Biological Activities of Transforming Growth Factor-beta and Platelet-Derived Growth Factor in vivo, Growth Factors, vol. 5, pp. 57-68, 1991.
O'Kane et al., Transforming Growth Factor bs and Wound Healing, Int J Biochem Cell Biol., vol. 29, pp. 63-78, 1997.
Okwueze et al., Modulation of Porcine Wound Repair with a Transfected ErbB3 Gene and Relevant EGF-Like Ligands, J Invest Dermatol., vol. 127, pp. 1030-1041, 2007.
Onuma et al., Quantitative analysis of the proliferation of epidermal cells using a human skin organ culture system and the effect of DbcAMP using markers of proliferation (BrdU, Ki-67, PCNA), Archives of Dermatological Research, vol. 293, pp. 133-138, 2001.
Pelton et al., Immunohistochemical localization of TGFb1, TGFb2, and TGFb3 in the mouse embryo: expression patterns suggest multiple roles during embryonic development, J Cell Biol., vol. 115, pp. 1091-1105, 1991.

(56) References Cited

OTHER PUBLICATIONS

Reiber et al., The burden of diabetic foot ulcers, Am J Surg, vol. 176, Suppl. 2A, 1998.
Roberts, et al., Transforming Growth Factor-beta. The Molecular and Cellular Biology of Wound Repair (2 Ed.), edited by R. Clark. New York: Plenum Press, pp. 275-308, 1996.
Rokeach et al., High-level bacterial expression, purification and characterization of human calreticulin, Engineering, vol. 4, pp. 981-987, 1991.
Schor et al., A Novel 'Sandwich' Assay for quantifying chemo-regulated cell migration within 3-dimensional matrices: wound healing cytokines exhibit distinct motogenic activities compared to the transmembrane assay, Cell Motil Cytoskeleton, vol. 63, pp. 287-300, 2006.
Sezestakowska et al., The Complexities of Calreticulin From Protein Folding to Disease Prevention and Therapeutic Application, Calcium Binding Proteins, vol. 12, pp. 135-139, 2006.
Shah Met al., Neutralisation of TGF-b1 and TGF-b2 or exogenous addition of TGF-b3 to cutaneous rat wounds reduces scarring, J Cell Sci, vol. 108, pp. 985-1002, 1995.
Singer et al., Cutaneous wound healing, Engl J Med, vol. 341, pp. 738-746, 1999.
Tesniere et al., Immunogenic cancer cell death: a key-lock paradigm, Curr Opin Immunology, vol. 20, pp. 504-511, 2008.
Werner et al., Suppression of Keratin 15 Expression by Transforming Growth Factor b in Vitro and by Cutaneous Injury in Vivo, Experimental Cell Research, vol. 254, pp. 80-90, 2000.
Wetzler et al., Large and Sustained Induction of Chemokines during Impaired Wound healing in the Genetically Diabetic Mouse: Prolonged Persistence of Neutrophils and Macrophages during the Late Phase of Repair, J. Invest. Derm., vol. 115, pp. 245-253, 2000.
Wu et al., Differential expression and activity of matrix metalloproteinase-2 and -9 in the calreticulin deficient cells, Matrix Biol., vol. 26, pp. 463-472, 2007.
Wu et al., Transforming Growth Factor Beta3 TGFBeta3 Accelerates Wound Healing Without Alteration of Scar Prominence, Arch Surgery, vol. 132, pp. 753-760, 1997.
Beatrice M. Magnusson, Simple Rules Defining the Potential U of Compounds for Transdermal Delivery or Toxicity, Pharmaceutical Research, vol. 21, No. 6, Jun. 2004.
Bos JD,The 500 Dalton rule for the skin penetration of chemical compounds and drugs, Exp Dermatol 2000: 9: 165-169.
Janet Kielhorn, Environmental Health Criteria 235, Dermal Absorption, WHO, 2006.
Arora et al. "The Role of Calreticulin Transacetylase in the Activation of Human Platelet Nitrite Reductase by Polyphenolic Acetates" Biol. Pharm. Bull. (2009), 32(2):161-165.
Bansal et al. "Autoacetylation of Purified Calreticulin Transacetylase Utilizing Acetoxycoumarin as the Acetyl Group Donor" Appl Biochem Biotechnol (2009), 157:285-298.
L. Van Duyn Graham et al.; "Intracellular Calreticulin Regulates Multiple Steps in Fibrillar Collagen Expression, Trafficking, and Processing into the Extracellular Matrix", Journal of Biological Chemistry, 2010, vol. 285, No. 10, pp. 7067-7078; originally published online Dec. 31, 2009.
Supplementary European Search Report and European Search Opinion dated Mar. 5, 2014, which issued during the prosecution of European Application No. 11796554.1, which corresponds to the present application.
Keisuke Kuwabara, Calreticulin, an Antithrombotic Agent Which Binds to Vitamin K-dependent Coagulaton Factors, Stimulates Endothelial Nitric Oxide Production, and Limits Thrombosis in Canine Coronary Arteries, The Journal of Biological Chemistry, vol. 270, No. 14, Issue Apr. 7, pp. 8179-8187, 1995.
UniProt Protein Database, protein Acession P27797, Calreticulin, pp. 1-12, Accessed on Oct. 16, 2014.
WebMD, Hyaluronic Acid, pp. 1-4, accessed on Oct. 17, 2014.
Meier, et al., Emerging new drugs for wound repair, Expert Opin. Emerging Drugs, vol. 11, pp. 23-37, 2006.
Meier et al., Emerging new drugs for scar reduction, Expert Opin. Emerging Drugs, vol. 11, pp. 39-47, 2006.
Cai et al, NO and NO Donors, Part 1: Chemistry of NO Donors, In Nitric Oxide Donors for Pharmaceutical and Biological Applications, Wang et al. eds., Wiley-VCH, pp. 1-31, 2005.
Rudinger, Peptide Hormones, JA Parsons, Ed., 1976, pp. 1-7.
SIGMA, 2004, pp. 1-2.
Berendsen, A Glimpse of the Holy Grail? Science, 1998,282, pp. 642-643.
Voet et al, Biochemistry, John Wiley & Sons Inc., 1995, pp. 235-241.
Ngo et al, Computational Complexity, Protein Structure Protection, and the Levinthal Paradox, 1994, pp. 491-494.
Bradley et al., Limits of Cooperativity in a Structurally Modular Protein: Response of the Notch Ankyrin Domain to Analogous Alanine Substitutions in Each Repeat, J. Mol. Biol (2002) 324, 373-386.
The On-line Medical Dictionary, Definition of a Derivative, pp. 1-5, Accessed Jul. 7, 2005.
International Preliminary Report on Patentability for PCT/US2011/040979, dated Dec. 18, 2012.
PCT Written Opinion of the ISR for PCT/US2011/040979, dated Feb. 3, 2012.
Communication issued by the European Patent Office in European Application No. 11796554.1, dated Jun. 29, 2015.
Communication issued by the European Patent Office in European Application No. 11796554.1, dated Feb. 23, 2016.
Communication issued by the European Patent Office in European Application No. 17166248.9, dated Dec. 22, 2017.
Martin, P. et al., "Wound Healing-Aiming for Perfect Skin Regeneration" Science (1997) vol. 276, pp. 75-81.
Communication issued by the Canada Patent Office in Canadian Application No. 2,805,412 dated Jun. 13, 2017, 4 pages total.
Communication issued by the Canada Patent Office in Canadian Application No. 2,805,412 dated May 25, 2018, 4 pages total.

* cited by examiner

Calreticulin induces TGF-β3 isoform in fibroblasts but not keratinocytes (24 hr)

SDS-PAGE: Comparison of molecular weight and purity of recombinant his-tagged human calreticulin (Genway Biotech) and recombinant rabbit calreticulin from Marek Michalak Lab These calreticulins from different sources were used in proliferation and migration assays giving similar specific activities

THERAPEUTIC AND COSMETIC USES AND APPLICATIONS OF CALRETICULIN

CROSS-REFERENCE TO RELATED APPLICATIONS

This application is a divisional application of U.S. patent application Ser. No. 13/717,349, filed on Dec. 17, 2012, now U.S. Pat. No. 9,254,310, which is the National Stage of International Patent Application No. PCT/US11/40979 filed on Jun. 17, 2011, which claims the benefit of priority to U.S. Provisional Patent Application No. 61/355,987, filed on Jun. 17, 2010, the entire contents of which applications are hereby incorporated by reference.

FIELD OF THE INVENTION

The present invention relates to therapeutic and cosmetic uses and applications of calreticulin. In particular, the invention relates to the therapeutic and cosmetic uses and applications of calreticulin to a patient in need of such treatment including in tissue repair, wound healing, acute and extensive deep tissue damage, burn wounds, healing of chronic wounds including venous and arterial stasis ulcers, pressure ulcers, diabetic foot ulcers (DFUs), ulcers resulting form sickle cell disease (SCU), orphan skin diseases with delayed wound healing (e.g., epidermolysis bullosa), reducing scar formation (e.g., keyloid), reducing or eliminating wrinkles including preventing fibroblast senescence (aging), corneal wound repair, bone and cartilage repair, (re)-growth of hair follicles and other epidermal appendages, obviating infection, tissue repair and preventing adhesions following surgical procedures, tissue reconstruction, and regeneration of peripheral nerves and of the central nervous system, skin diseases lacking the function of cell proliferation (e.g., Lentiga maligna) and immunologic disorders due to lack of cellular migration and the ability of cells to phagocytose bacteria and parasites (e.g., Wiscott-Aldrich Syndrome).

BACKGROUND OF THE INVENTION

Wounds can be divided into two major categories: acute wounds, such as those associated with surgical incisions and excisions, bites, burns, cuts and abrasions, as well as more traumatic wounds such as lacerations and those caused by crush or gun shot injuries, and chronic or impaired non-healing wounds, such as those associated with diabetes, venous and arterial stasis leg ulcers, foot ulcers, and pressure sores to name a few.

Acute wound healing has been categorized into four phases: coagulation, inflammation, proliferation, and remodeling (Singer, A. J. and Clark, R. A. (1999) N. Engl. J. Med. 341:738-746). At the time of injury, coagulation is initiated by activated platelets binding thrombin and forming a plug. Vasoconstriction and cytokine release also occur. For example, platelet-derived growth factor (PDGF), fibroblast growth factor (FGF), vascular endothelial growth factor (VEGF), and transforming growth factor-beta (TGF-β) are common factors released. During the second phase, inflammatory cells, such as macrophages and polymorphonuclear (PMN) cells are recruited, which phagocytose (engulf) bacteria, remove dead tissue/cells (wound debridement), and produce additional cytokines and growth factors such as IL-6 and TGF-β. Fibroblasts are also recruited and produce matrix components such as fibronectin and collagen. Within 1-2 days after injury, keratinocytes proliferate at the wound margin and subsequently migrate both, over the wound and upward from any remaining hair follicles and sweat ducts to begin wound resurfacing, termed re-epithelialization. Matrix metalloproteinases (MMPs) are produced by inflammatory cells, and help prepare the wound for angiogenesis (new blood vessel formation). In the proliferation phase, fibroblasts and endothelial cells proliferate, and fibroblasts secrete extracellular matrix proteins forming granulation tissue. Later, fibroblasts remodel tissue, macrophages continue to debride the wound, fibroblasts continue to synthesize and release growth factors and extracellular matrix (ECM) proteins, such as collagens and fibronectin, and a subpopulation of fibroblasts differentiate into myofibroblasts that produce more ECM and cause wound contraction. The granulation tissue serves as a matrix over which the keratinocytes migrate to create the new epidermal surface across the wound. The wound contracts and later a scar is formed by excessive tissue remodeling. During the final remodeling phase, collagen fibrils in the scar are degraded by MMPs. Thus, numerous cell types and complex molecular events and biologic processes must stochastically interact to bring about [cutaneous] repair of injury. The most critical molecular events involved in normal wound healing are cell migration, cell proliferation, and wound contraction. The major cell types involved in the [cutaneous] wound healing process are keratinocytes, fibroblasts, endothelial cells, and immune cells, and mesenchymal stem cells. General tissue repair involves similar cellular processes in a more regenerative sense largely involving proliferation and differentiation of the particular cell types composing a damaged organ, bone, cartilage, tendon, ligament etc. and angiogenesis to supply the repairing tissue with nutrients. The migration of mesenchymal stem cells endothelial stem cells are shown to be an important cell type involved in the wound healing and tissue repair process. Stem cells, normally involved in development, are released from the bone marrow when cytokines are released into the circulation upon injury. These progenitor cells, including mesenchymal stem cells (MSCs), fibrocytes (derived from MSCs; CD34+, Col I+, CD11b+, CD13+, MHC class II+), and endothelial progenitors cells (EPCs) provide important contributions to the wound healing/tissue repair and regeneration process (Liu, Z. J. et al (2009) J Cell Biochem. 106:984-991; Abe, R. et al (2001) J. Immunol. 166:7556-7562).

Unlike acute wound healing, chronic wound healing does not proceed normally through the four healing phases. Chronic wounds are characterized by a lack of continuity and integrity of healing with wounds lasting more than 8 weeks, no healing, or a recurring wound (Liu, Z. J. and Velasquez, O. C. (2008) Antiox. Redox. Signal. 10:1869-1882). These wounds are arrested in the inflammatory phase of healing and demonstrate persistent infection concomitant with a constant influx of neutrophils that perpetuate the release of cytotoxic enzymes, free oxygen radicals and other inflammatory mediators. There are increased levels of cytokines and continued destruction of tissue by matrix metalloproteinases (MMPs) (Singer, A. J. and Clark, R. A. (1999) N. Engl. J. Med. 341:738-746). Specifically, the inflammatory excess is characterized by excessive production of Interleukin-6 (IL-6), tumor necrosis factor-alpha (TNF-α), and MMPs). Other defects are a deficiency of important growth factors needed for proper healing, and bacterial overgrowth and senescence of fibroblasts. Further, the epithelial layer fails to cover the entire surface of the wound and, consequently, a chronic wound remains open and subject to infection. Bacteria colonize the chronic wound beneath a biofilm layer (which they secrete), activate virulence factors, and trigger NFκB-dependent inflammatory pathways, thereby continuing the process of inflammatory excess that prevents proper healing of the wound. A resulting dead tissue accumulates completely retarding healing and therefore, chronic wounds require frequent surgical debridement to remove debris. Failure of mesenchymal stem cells to home to injured sites is a problem in chronic wound healing leading to lack of proper cell differentiation and angiogenesis. It has been shown that chronic-impaired wounds, such as diabetic wounds, contain less stromal-derived factor (SDF-1$\alpha$), a protein required for homing of EPCs to the wound.

A type of chronic wound is a diabetic wound, which are largely diabetic foot ulcers (DFUs). Similar to other chronic wounds but more severe, these wounds are defective in cell proliferation, the migration of cells into the wound including macrophage infiltration, extracellular matrix production, clearance of dead tissue and apoptotic cells, and fibromyoblast differentiation (Ochoa, O. et al (2007) Vasc 15:350-355). It is also proposed that high glucose levels (hyperglycemia) in diabetics cause cell wall rigidity, which impedes red blood cell permeability, and impairs blood flow through the microvasculature causing ischemia at the wound surface. New blood vessel growth is impaired by lack of VEGF production (Galiano, R. D. et al (2004) Am. J. Pathol. 161:19351947.

Novel therapies/agents to heal all types of chronic non-healing wounds and extensively injured tissue, including epidermal and dermal skin substitutes (cell-based therapies/wound devices) have largely failed causing an insurmountable and unsolved medical problem (Clark, R. A. et al (2007) J. Invest. Dermatol. 127:1018-1029). Existing pharmaceutical agents, such as Regranex® gel, are currently used to treat acute and chronic wounds. Regranex® gel contains becaplermin, a recombinant human platelet-derived growth factor isoform dimer, BB (PDGF-BB), which promotes cellular proliferation of the cells of the dermis, which are mainly fibroblasts, and angiogenesis. It is indicated for the treatment of lower extremity diabetic neuropathic ulcers that extend into the subcutaneous tissue or beyond and have an inadequate blood supply. An increased rate of malignancies and death in patients using Regranex® gel has been reported, indicating that safer alternatives to this drug are needed. Other proteins that have shown promise in vivo include vascular endothelial growth factor (VEGF), fibroblast growth factor (FGF), epidermal growth factor (EGF), transforming growth factor-$\beta$ (TGF-$\beta$) and others. Galiano et al., Am J Pathol 2004, 164:1935-1947; Michaels et al., Wound Repair and Regeneration 2005, 13:506-512; Obara et al., Wound Repair and Regeneration 2005, 13:390-397; Greenhalgh et al., Am J Pathol 1990, 136:1235-1246; Acosta et al., International Wound Journal 2006, 3:232-239.

A role for calreticulin, a 46 kDa protein (it resolves at a higher molecular weight in SDS-page, e.g. 55-60) associated with hyaluronan, in the treatement of acute wounds (and reduced scar formation), such as surgical wounds and wounds incurred in accidental trauma, has been described by the present inventors. See, e.g., U.S. Pat. No. 5,591,716. Calreticulin is a highly conserved major calcium-binding protein of the endoplasmic reticulum (ER) consisting of three structurally and functionally distinct domains—the N, P and the C domains, as shown in FIG. 36. (Bedard, K., et al., (2005) *Int Rev Cytol* 245, 91-121; Michalak, M., et al., (2009) *Biochem J*417, 651-666) (FIGS. 37 and 38). As shown in FIGS. 36 and 37, the middle P and C-terminal domains contain a number of high- and low-affinity calcium interacting sites, respectively. The N-terminal domain contains a signal sequence for targeting to the ER and the C-terminal domain has a KDEL sequence at its C-terminus, for retrieval/retention in the ER. Within the lumen of the ER, CRT in concert with other ER-resident chaperones mainly, 1) ensures proper folding of proteins and glycoproteins mainly via its lectin-binding site, 2) prevents protein aggregation and 3) is engaged in protein quality control through identifying and banning misfolded proteins from the ER for ubiquitin-mediated destruction. Another important function for CRT directed from the ER is in the regulation of calcium metabolism, which influences a variety of cellular functions including cell signaling, particularly through integrins. The heralded functions of calreticulin are intracellular, in calcium homeostasis and in binding N-linked oligosaccharide protein intermediates to ensure proper glycoprotein conformation in the ER. Johnson, S. et al. (2001) Trends Cell Biol. 11:122-129; Bedard, K. et al. (2005) Int. Rev. Cytol. 11:122-129; Sezestakowska, D. et al. (2006) International Workshop on Calreticulin, Niagara Falls, Canada. 1:135-139; Gold, L. I. et al. (2006) J. Investig. Dermatol. Symp. Proc. 11:57-65. However, more recently, roles for calreticulin in extracellular functions have been emerging (FIG. 37) such as the processes of wound healing, adaptive immune response in cancer, clearance of apoptotic cells by phagocytes, thrombospondin-mediated migration and prevention from anoikis, and the uptake of necrotic tumor cells by dendritic cells (review Michalak, M. et al (2009) Biochem. J. 417:651-656).

Chronic wounds and their management are very different than acute wounds and, thus, therapeutic agents that are useful for the treatment of acute wounds may not be as useful for the treatment of chronic wounds. Thus, there remains a need to discover new therapeutic agents and methods of treatment that are useful for the healing of chronic wounds, including chronic diabetic wounds.

SUMMARY OF THE INVENTION

The present invention addresses multiple medical and cosmetic needs as it provides therapeutic and cosmetic methods which involve the use of calreticulin for tissue repair and reconstruction (including, among others, enhancement of corneal wound repair, bone and cartilage repair, (re)-growth of hair follicles and other epidermal appendages, and regeneration of peripheral nerves and of the central nervous system), wound healing (including, among others, treatment of acute and extensive deep tissue damage, treatment of burn wounds, healing of chronic wounds [including, among others, venous and arterial stasis ulcers, pressure ulcers, diabetic foot ulcers (DFUs), ulcers resulting form sickle cell disease (SCU)]), treatment of orphan skin diseases with delayed wound healing (e.g., epidermolysis bullosa), reduction of scar formation (e.g., keyloid) and prevention of adhesions following surgical procedures, treatment of wrinkles including preventing fibroblast senescence (aging), treatment of skin diseases lacking the function of cell proliferation (e.g., Lentiga maligna), as well as treatment/prevention of infections and treatment of immunologic disorders due to lack of cellular migration and the ability of cells to phagocytose bacteria and parasites (e.g., Wiscott-Aldrich Syndrome).

In one aspect, the invention provides a method of treating wrinkles and/or fine lines in a subject in need thereof, which method comprises administering to said wrinkles an effective amount of calreticulin or a functional fragment or derivative thereof. In one embodiment, said treatment results in at least one effect on wrinkles and/or fine lines selected from the group consisting of reducing the noticeability, improving the appearance, decreasing the depth, decreasing the number, and any combination thereof.

In another aspect, the invention provides a method of achieving a tissue reconstruction in a patient in need thereof, which method comprises administering to the patient a therapeutically effective amount of calreticulin or a functional fragment or derivative thereof.

In yet another aspect, the invention provides a method of repairing damaged bone and/or cartilage in a patient in need thereof, which method comprises administering to the damaged bone and/or cartilage of the patient a therapeutically effective amount of calreticulin or a functional fragment or derivative thereof.

In a further aspect, the invention provides a method of stimulating regeneration of an epidermal appendage (e.g., stimulating hair follicle regeneration) in a wound or skin of a patient in need thereof, which method comprises administering to the wound or skin of the patient a therapeutically effective amount of calreticulin or a functional fragment or derivative thereof.

In another aspect, the invention provides a method for enhancing phagocytosis of bacteria by phagocytes within a wound, of a patient in need thereof, which method comprises administering to the wound of the patient a therapeutically effective amount of calreticulin or a functional fragment or derivative thereof.

In a further aspect, the invention provides a method for treating a wound in a patient suffering from delayed wound healing, which method comprises administering to the wound of the patient a therapeutically effective amount of calreticulin or a functional fragment or derivative thereof. In one embodiment, the patient suffering from delayed wound healing is suffering from sickle cell disease and the wound is a skin ulcer (e.g., located on the leg). In another embodiment, the patient suffering from delayed wound healing is suffering from epidermolysis bullosa and the wound is an open wound upon epidermal sloughing.

Wounds treatable by the methods of the present invention include acute wounds and chronic wounds.

In one aspect, the invention provides a method for treating a corneal wound (e.g., corneal abrasion) in a patient in need thereof, which method comprises administering to the corneal wound of the patient a therapeutically effective amount of calreticulin or a functional fragment or derivative thereof.

In a further aspect, the invention provides a method for treating or preventing a surgical adhesion in a patient in need thereof, which method comprises administering to the site of surgery in the patient a therapeutically effective amount of calreticulin or a functional fragment or derivative thereof.

In the methods of the invention, calreticulin or a functional fragment or derivative thereof can be administered to the site of action, e.g., by a route selected from the group consisting of topical, subcutaneous (e.g., by injection), intradermal, transdermal (e.g., via a transdermal patch), and intracorporal.

In the methods of the invention, calreticulin or a functional fragment or derivative thereof can be administered in an amount ranging between about 0.001 milligram and about 100 grams (e.g., between about 0.01 milligram and about 50 milligrams).

In the methods of the invention, calreticulin or a functional fragment or derivative thereof can be administered in combination with another active agent such as, e.g., a cytokine, a growth factor (e.g., platelet-derived growth factor, vascular endothelial growth factor, fibroblast growth factor, epidermal growth factor, transforming growth factor-beta, and any mixtures thereof), a glycosaminoglycan (e.g., hyaluronic acid), a proteoglycan (e.g., perlecan or heparin sulfate), syndecan, or any mixtures thereof.

A summary of the Examples (infra), which illustrate the methods of the present invention and the effects of calreticulin on the healing of a chronic diabetic wound compared to Regranex® gel-treated (the only FDA-approved wound healing agent) and buffer-treated control wounds is provided in Table 1. The biological functions and qualities of calreticulin described in Table 1 have application to improve and enhance both acute and chronic wound healing.

TABLE 1

| | Calreticulin-treated | Regranex ® Gel-treated chronic wounds | Buffer-treated |
|---|---|---|---|
| Neo-dermal depth | ++ | + | + |
| Numbers of proliferating basal Keratinocytes | +++ | + | + |
| Numbers of proliferating neodermal Fibroblasts | +++ | ++ | +/− |
| Macrophage influx into the wound bed | +++ | + | + |
| Increases rate of reepithelialization | +++ | 0 | + |

The present invention provides methods for using calreticulin for therapeutic and cosmetic applications comprising administering a therapeutically effective amount of calreticulin to a patient in need of such treatment. The invention provides methods for accelerating or improving the quality of wound repair, preventing scarring or keloid formation, prevent surgical adhesions, treat burn wounds, repair corneal wounds, treat wounds as a result of a patient having sickle cell anemia, treat wounds of a patient having epidermylosis bullosa, promote hair follicle regeneration within a wound or in the skin, eradicate wrinkles, prevent senescence of fibroblasts, and bone and cartilage repair. The invention provides methods for treating incisional wounds that heal by first intention as well as excisional full-thickness or partial-thickness wounds that heal by second intention and also, for general tissue repair and regeneration.

In one embodiment, the wound may be an open wound, a closed wound, a cut, or a wound derived from facial plastic surgery or full-body plastic surgery. Examples of open wounds include, but are not limited to, an incision, a laceration, an abrasion, a puncture wound, a penetration wound, a gunshot wound, a stabbing wound, extensive shrapnel wound, and a burn wound. Examples of closed wounds include, but are not limited to, a contusion or a hematoma. In certain embodiments, the healing of the wound, re-epithelialization, or reduction of scarring during healing is accelerated and the quality of the process is improved. In other embodiments, the wound is covered by a scab in whole or in part, contains active fibroblasts, or is an acute or chronic wound. In yet other embodiments, the cut is an incision of the epidermis. In certain embodiments, the wound is a corneal wound.

In another embodiment, a wound may be derived from cosmetic surgery, such facial plastic surgery or full-body plastic surgery. Examples of facial plastic surgery include, but are not limited to, rhytidectomy, blepharoplasty, rhinoplasty, otoplasty, mentoplasty, face lift, fore head lift, brow lift, facial scar revision, facial scar removal, laser surgery, skin resurfacing, wrinkle treatment, plasma skin regeneration, facial fat grafting, skin tightening, tattoo removal hair replacement, and tissue reconstruction. Examples of full-body plastic surgery include, but are not limited to, abdominoplasty, breast reduction, breast enhancement, body lift procedures, spider vein treatment, stretch mark treatment, liposuction, excess skin removal surgery, cellulite reduction treatment, body contouring, body resurfacing and body implants.

Another embodiment of the present invention comprises the use of calreticulin as a cosmecutical, for the reduction or eradication of wrinkles. In another embodiment, calreticulin is administered for bone and cartilage repair immediately following a surgical procedure before the wound is closed or by injection into the repaired site.

In certain embodiments of the invention, the wound is a chronic wound such as but not limited to a chronic diabetic wound, a venous or arterial stasis ulcer or pressure ulcer (bed sores). In a further embodiment, the calreticulin is administered topically to a chronic diabetic wound of the patient. A specific type of chronic diabetic wound according to the present invention may be a diabetic foot ulcer.

The methods of the present invention include topically, or by injection, administering calreticulin to a patient in need thereof in an amount between about 0.001 milligram and about 1 gram, preferably between about 0.01 milligram and about 50 milligrams, and most preferably between 0.01 milligram and 10 milligrams.

According to the present invention, calreticulin can be administered in combination with a cytokine, a growth factor, any agonist of wound healing (or effective wound healing agent), including but not limited to small molecule agonists, peptide agonists, chemical agonists, or mixtures thereof. A growth factor according to the present invention can be, for example, platelet-derived growth factor, vascular endothelial growth factor, fibroblast growth factor, epidermal growth factor, TGF-β, and mixtures thereof. Calreticulin may also be administered in combination with other wound healing agents or anti-scarring agents or anti-wrinkle or bone and cartilage repair agents. Examples of such agents include but are not limited to bone morphogenetic proteins, TGF-βs, and other growth factors and cytokines. This treatment will activate these cells to migrate, proliferate, and produce extracellular matrix proteins including, but not limited to, collagens, fibronectin, and TGF-β3 to resurfact and fill in the wound defect. Calreticulin may also be used to treat “wound healing cells” such as keratinocytes and fibroblasts that will be added to cell based therapies or skin equivalents for the treatment of wounds. Calreticulin can be embedded or complexed chemically or ionically (electrostatically) to any chemical, polymer or natural matrix or scaffold for that can be applied to a cutaneous wound or tissue such as bone and cartilage.

According to the present invention, a therapeutically effective amount of a functional fragment of calreticulin is administered to the patient in order to treat the wound of a patient. In a preferred embodiment, the wound is an acute wound injury or chronic wound.

In an embodiment of the invention, a therapeutically effective amount of calreticulin is administered to the wound of a patient, such that the rate of wound healing is increased and/or the quality of the wound is improved relative to the rate of wound healing prior to the administration of calreticulin. In a preferred embodiment, the wound is an acute wound injury or a chronic wound.

The present invention provides a method for inducing re-epithelialization of a wound of a patient, which comprises topically administering a therapeutically effective amount of calreticulin to the wound of the patient. In a preferred embodiment, the wound is an acute wound injury or a chronic wound.

According to the methods of the present invention, macrophage migration into a wound of a patient is induced by topically administering a therapeutically effective amount of calreticulin to the wound of the patient. The present invention further provides a method for inducing keratinocyte migration (for wound re-epithelialzation, as described above) into a wound of a patient by topically administering a therapeutically effective amount of calreticulin to the wound of the patient. In an embodiment of the invention, a method for inducing endothelial cell migration into a wound of a patient is provided, which comprises topically administering a therapeutically effective amount of calreticulin to the wound of the patient. In an embodiment of the invention, a method for inducing monocyte migration into a wound of a patient is provided, which comprises topically administering a therapeutically effective amount of calreticulin to the wound of the patient. According to the present invention, fibroblast migration into a wound of a patient is induced by topically administering a therapeutically effective amount of calreticulin to the wound of the patient. In an embodiment of the invention, a method for inducing human mesenchymal stem cell migration into the wound is provided, which comprises topically administering a therapeutically effective amount of calreticulin to the wound of the patient. In a preferred embodiment, the wound is an acute wound injury or a chronic wound.

A method for inducing TGF-β expression (for induction of extracellular matrix proteins required) for granulation tissue formation and wound remodeling, and for wound healing without a scar) in a wound of a patient is provided by the present invention, which method comprises topically administering a therapeutically effective amount of calreticulin to the wound of the patient. In a preferred embodiment, the wound is an acute wound injury or a chronic wound.

The present invention provides a method for increasing extracellular matrix formation (to fill in and heal the wound defect) by inducing fibroblasts to produce fibronectin and collagens, which comprises topically administering or injecting a therapeutically effective amount of calreticulin into a wound of a patient. In a preferred embodiment, the wound is an acute wound injury or chronic wound. According to the present invention, calreticulin can be administered to a patient for cosmetic purposes for the reduction of wrinkles and scarring. Calreticulin can be administered with or without hyaluronic acid for the reduction of wrinkles.

The present invention provides a method for increasing alpha smooth muscle actin expression by fibroblasts for wound contraction in the wound of a patient by topically administering a therapeutically effective amount of calreticulin into a wound of a patient. In a preferred embodiment, the wound is an acute wound injury or a chronic wound.

According to the methods of the present invention, alpha5 and beta1 integrins are induced to be expressed by keratinocytes and fibroblasts by administering a therapeutically effective amount of calreticulin to the wound of a patient. The presence of calreticulin in this context will mediate their migration of these cells into a wound. In a preferred embodiment, the wound is an acute wound injury or chronic wound.

The present invention provides a method for enhancing phagocytosis of bacteria by phagocytes for reduction of bacterial burden (and biofilm) within the wound of a patient by administering a therapeutically effective amount of calreticulin to the wound. In a preferred embodiment, the wound is an acute wound injury or chronic wound.

In an embodiment of the invention, cell proliferation is induced in a wound of a patient by topically administering a therapeutically effective amount of calreticulin to the wound of the patient. The cell which is induced to proliferate can be, for example, a keratinocyte, a fibroblast, a dermal cell, and an endothelial cell. In a preferred embodiment, the wound is an acute wound injury or a chronic wound.

The present invention provides methods for increasing granulation tissue formation in a wound of a patient, which comprise topically administering a therapeutically effective amount of calreticulin to the patient, wherein the amount of granulation tissue is increased relative to the amount of granulation tissue present in the wound prior to calreticulin administration. In a preferred embodiment, the wound is an acute wound injury or a chronic wound.

According to the present invention, a method for increasing the rate and/or quality of wound healing in a wound of a patient is provided, which method comprises administering a therapeutically effective amount of calreticulin to the patient, wherein the rate and/or quality of wound healing is increased relative to the rate and/or quality of wound healing prior to administration of calreticulin.

According to the present invention, a method of attracting a patient's own cells for producing extracellular matrix proteins such as collagen is provided for the reduction or elimination of wrinkles, which comprises administering a therapeutically effective amount of calreticulin to the site of the patient.

Old CRT=rabbit calreticulin from M. Michalak laboratory, University of Alberta, made in pBad plasmid in an *E. coli* host. This material was 1.5 yrs old and was stored at 4 C.

Marek=rabbit calreticulin from M. Michalak laboratory, University of Alberta made in pBAD plasmid in an *E. coli* host. This material was 1-3 months old when used.

GenWay=human calreticulin purchased from GenWay Biotech, San Diego Calif.

Figure 27:
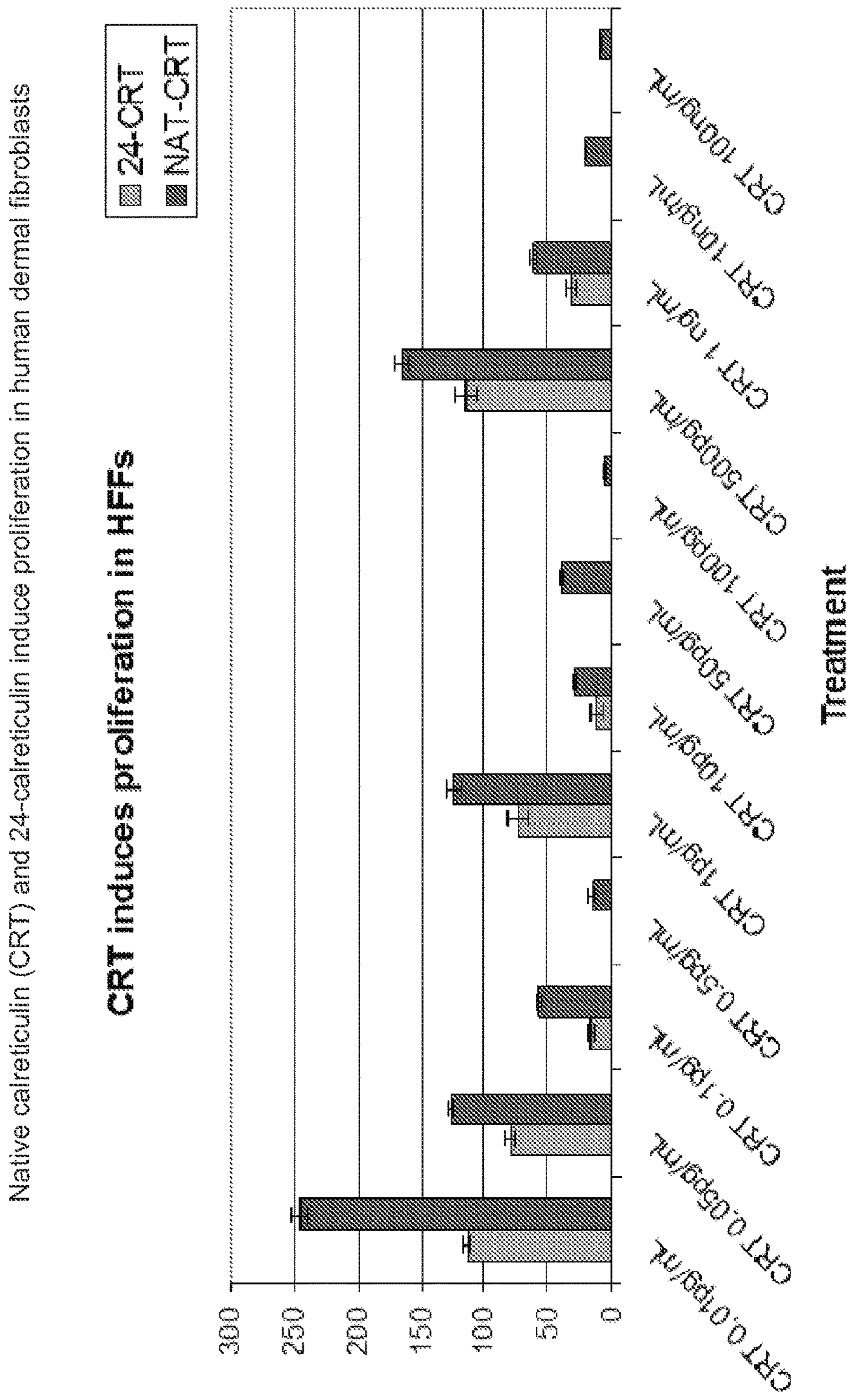

FIG. 27 is a bar graph showing that native calreticulin isolated and purified from dog pancreas (NAT-CRT) and calreticulin with an N-terminal histidine tag plus 23 additional amino acid residues (23-CRT) stimulate proliferation of human dermal fibroblasts (HDF) using a colorimetric MTS assay (Cell-titer96; Promega, Madison, Wis.).

Figure 28:
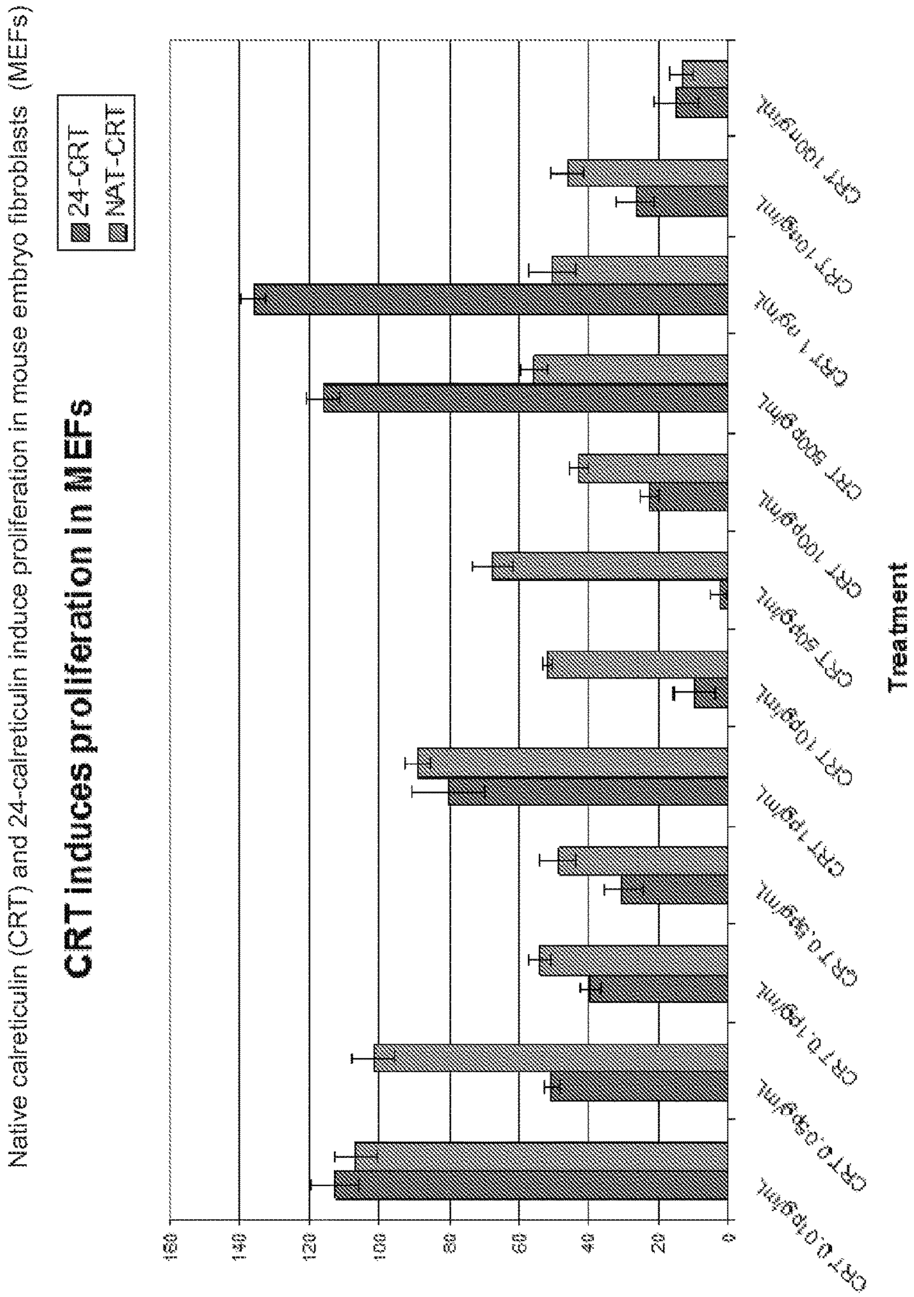

FIG. 28 is a bar graph showing that NAT-CRT and Michalak 23-CRT at increasing concentrations stimulated proliferation of mouse embryo fibroblasts (MEF s).

Figure 29:
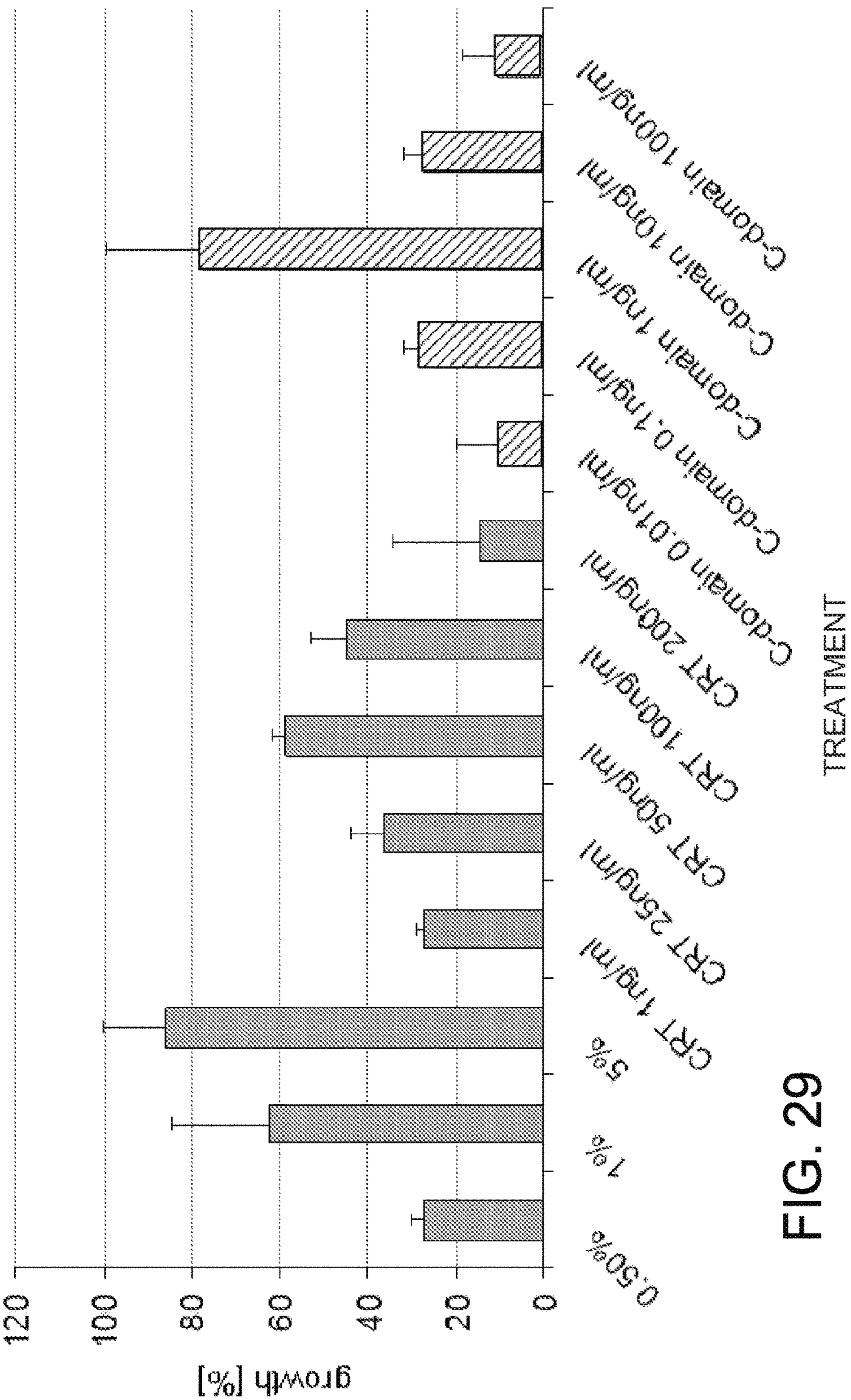

FIG. 29 is a bar graph comparing the C-domain (amino acid residues 285-400 (115 amino acids) of rabbit calreticulin to human calreticulin from GenWay Biotech in the stimulation of proliferation of human dermal fibroblasts (HDFs).

Figure 30:
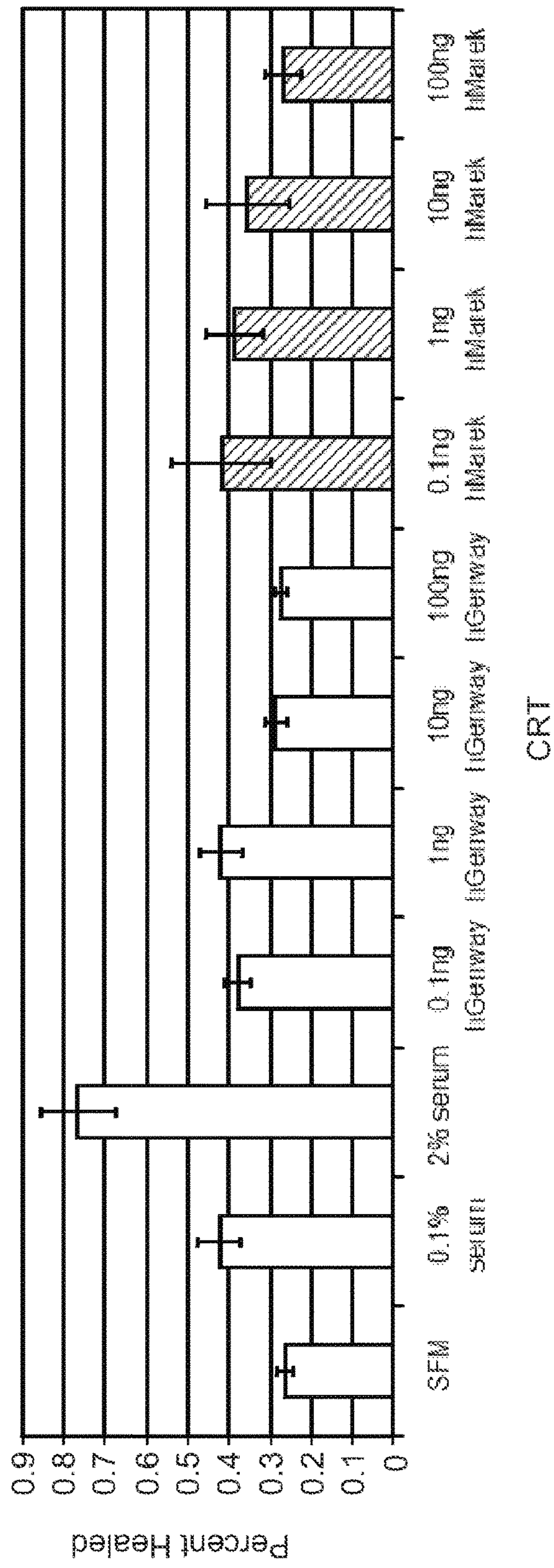

FIG. 30 is a bar graph showing that increasing concentrations of GenWay human calreticulin and human calreticulin containing a mixture of 5 amino acids at its N-terminus (5-CRT) and calreticulin containing 23 amino acids at its N-terminus (23-CRT) from the Michalak's laboratory stimulated the migration of human dermal fibroblasts.

Figure 31:
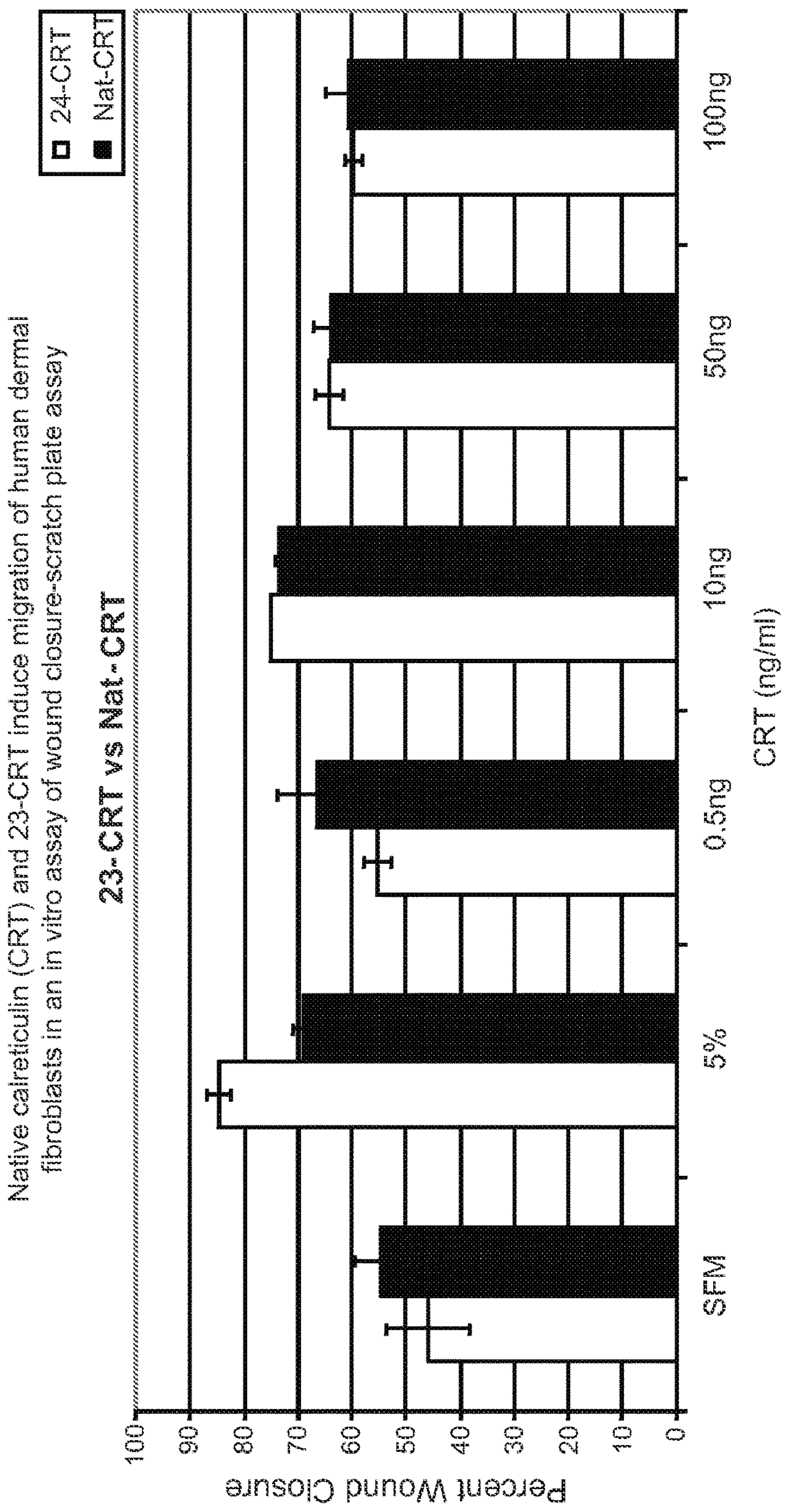

FIG. 31 is a bar graph showing that native calreticulin [from dog pancreas] and 23-CRT induced migration of human dermal fibroblasts using a scratch plate assay as an in vitro assay of wound closure due to induction of cell migration.

Figure 32:
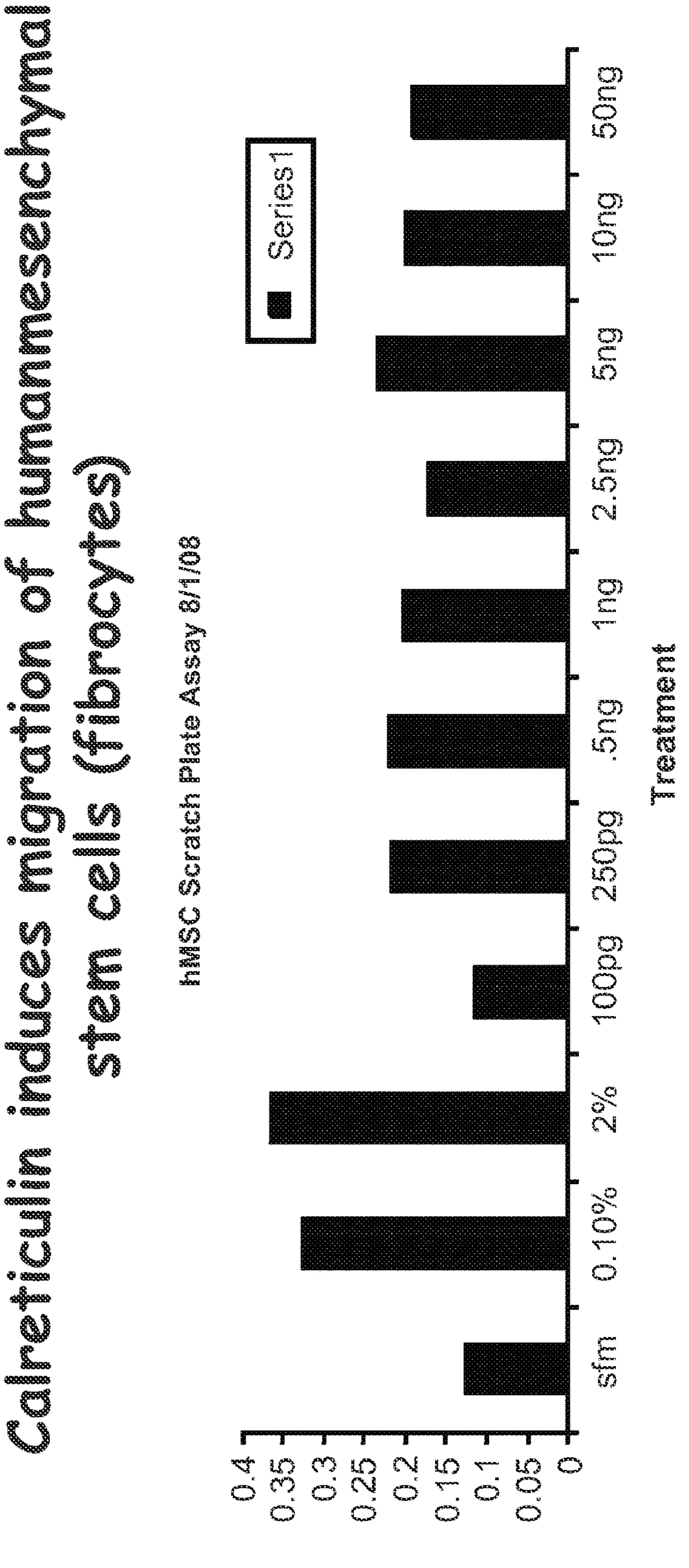

FIG. 32 is a bar graph showing that human calreticulin from GenWay induced migration of human mesenchymal stem cells using a scratch plate assay.

Figures 33A, 33B:
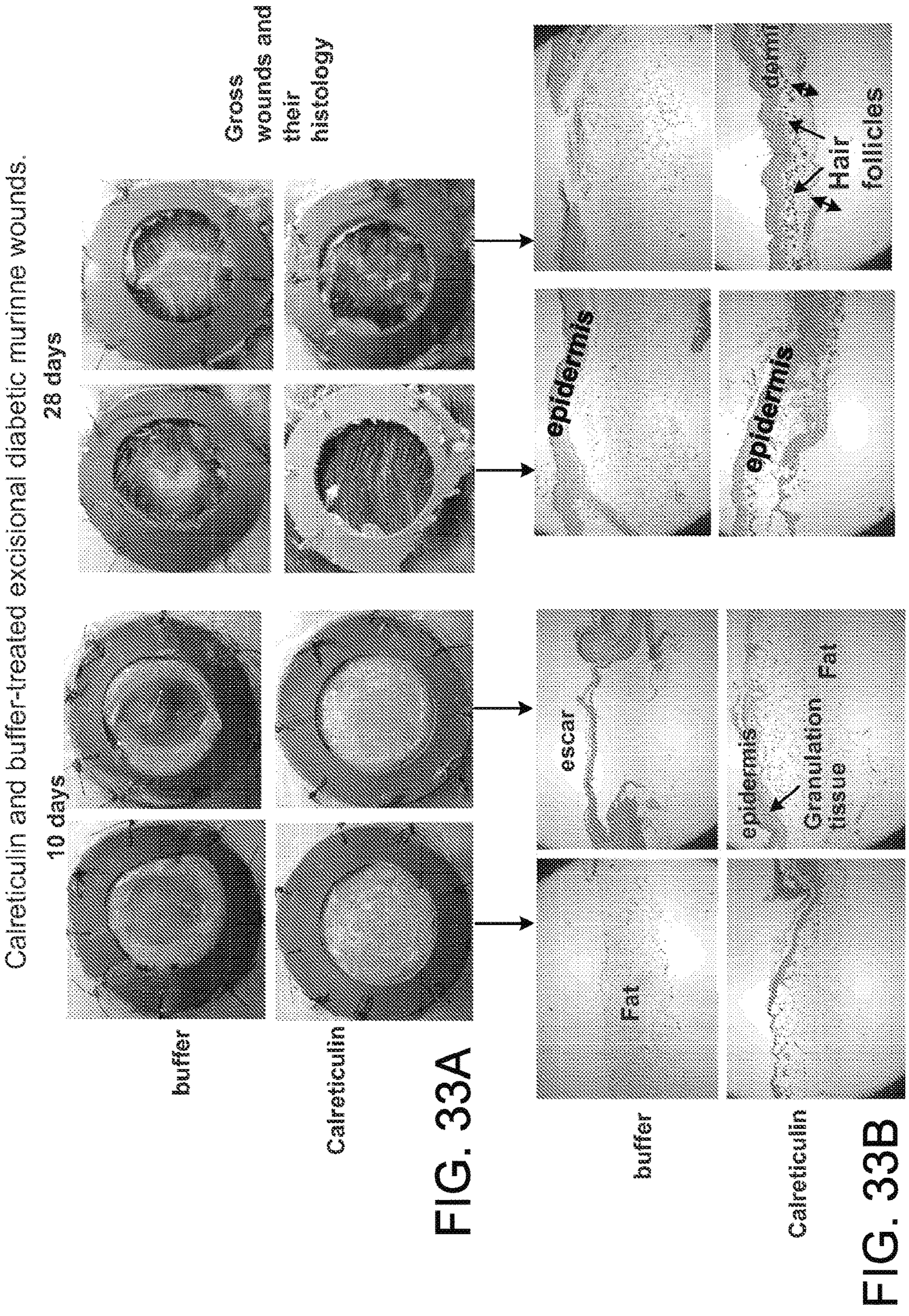

FIG. 33A shows gross murine wounds (db/db) treated with calreticulin or buffer (saline) at 10 and 28 days post-wounding and their histology. FIG. 33B shows the histology of the wounds corresponding to the gross wounds shown above in FIG. 33A.

Figure 34:
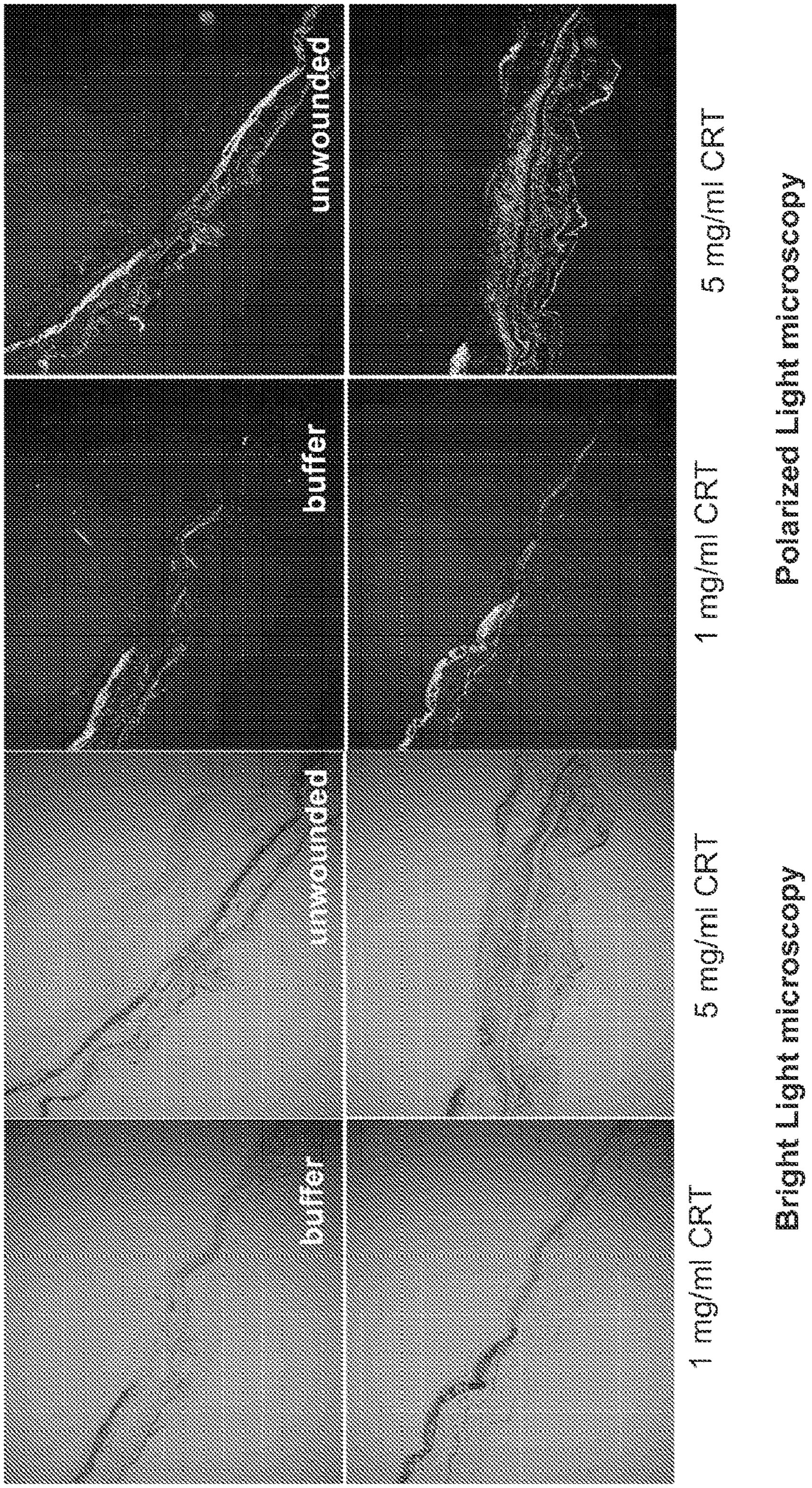

FIG. 34 shows that calreticulin induces a dose-dependent increase in collagen deposition in calreticulin-treated compared to buffer-treated wounds at 10 days post-wounding. The method used is picrosirius red staining for collagen organization.

Figure 35:
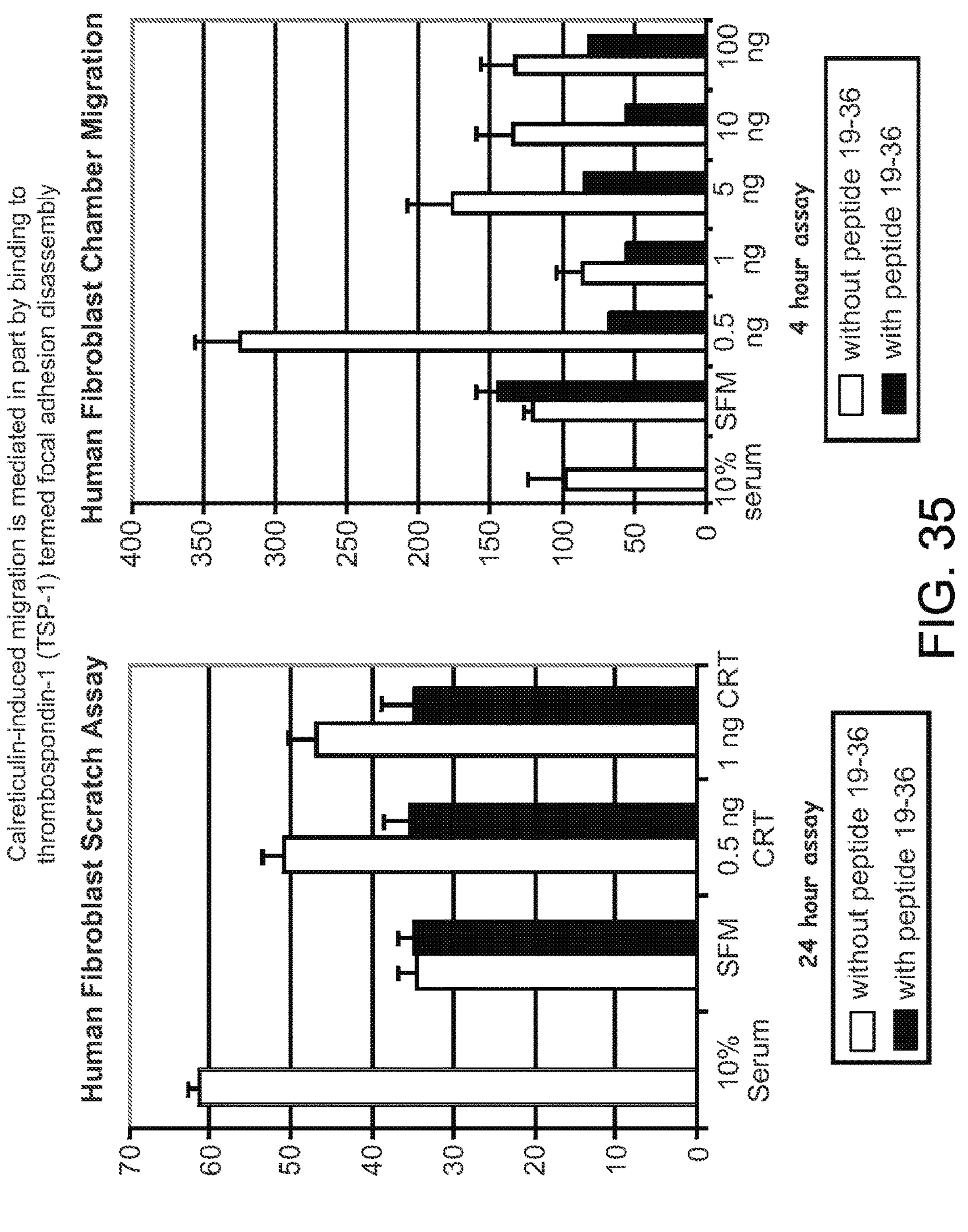

FIG. 35 shows that migration of fibroblasts in response to calreticulin involves focal adhesion disassembly (the binding of surface calreticulin to thrombspondin-1 (TSP-1) with signaling through the lipoprotein receptor-related protein 1 (LRP1), as a signaling complex). The peptide is amino acid residues 17-36 of TSP-1, which is the binding site on TSP-1 that binds to amino acid residues 19-36 in the N-Domain of calreticulin.

Figure 36:
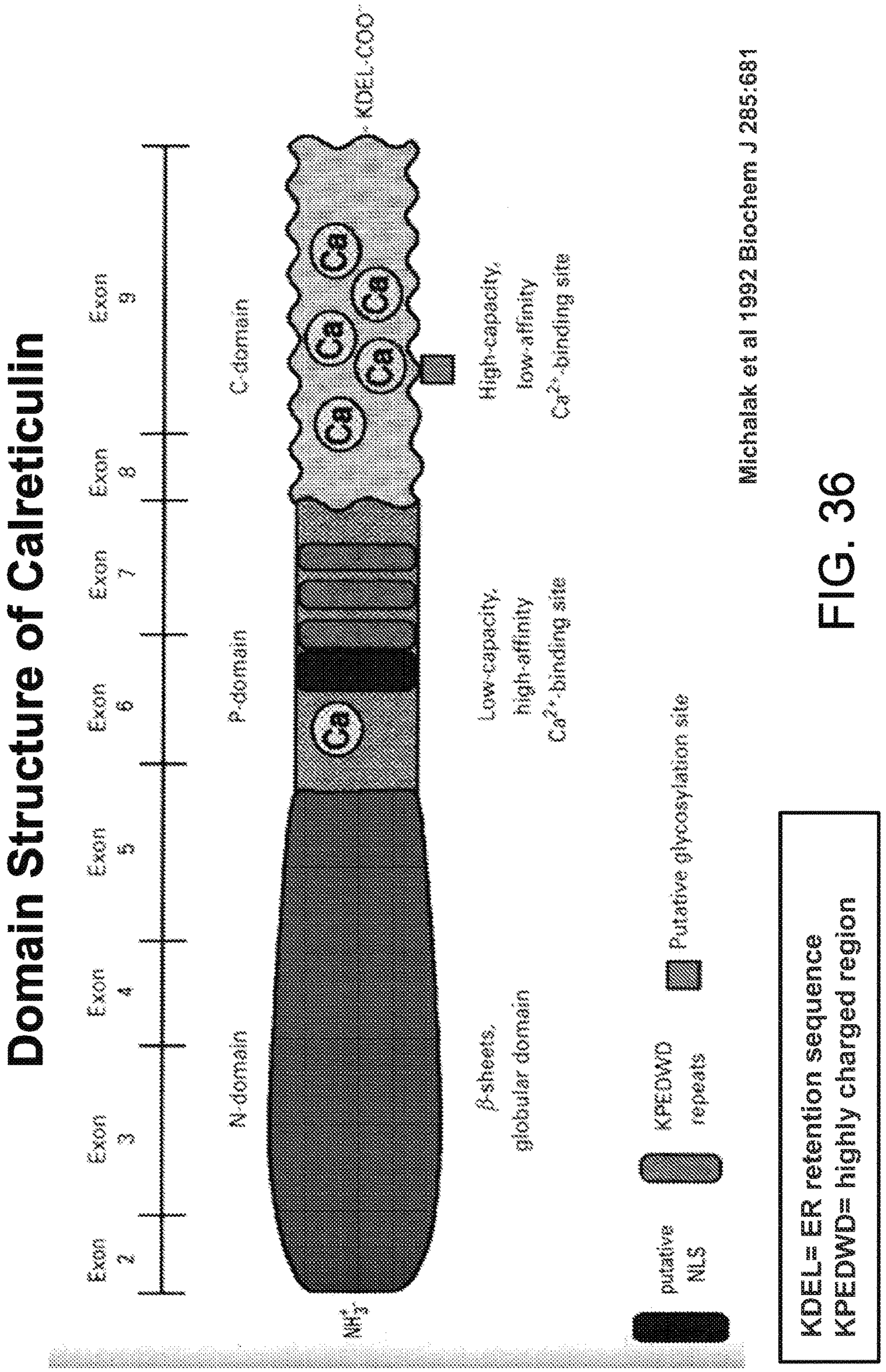

FIG. 36 shows the domain structure of calreticulin.

Figure 37:
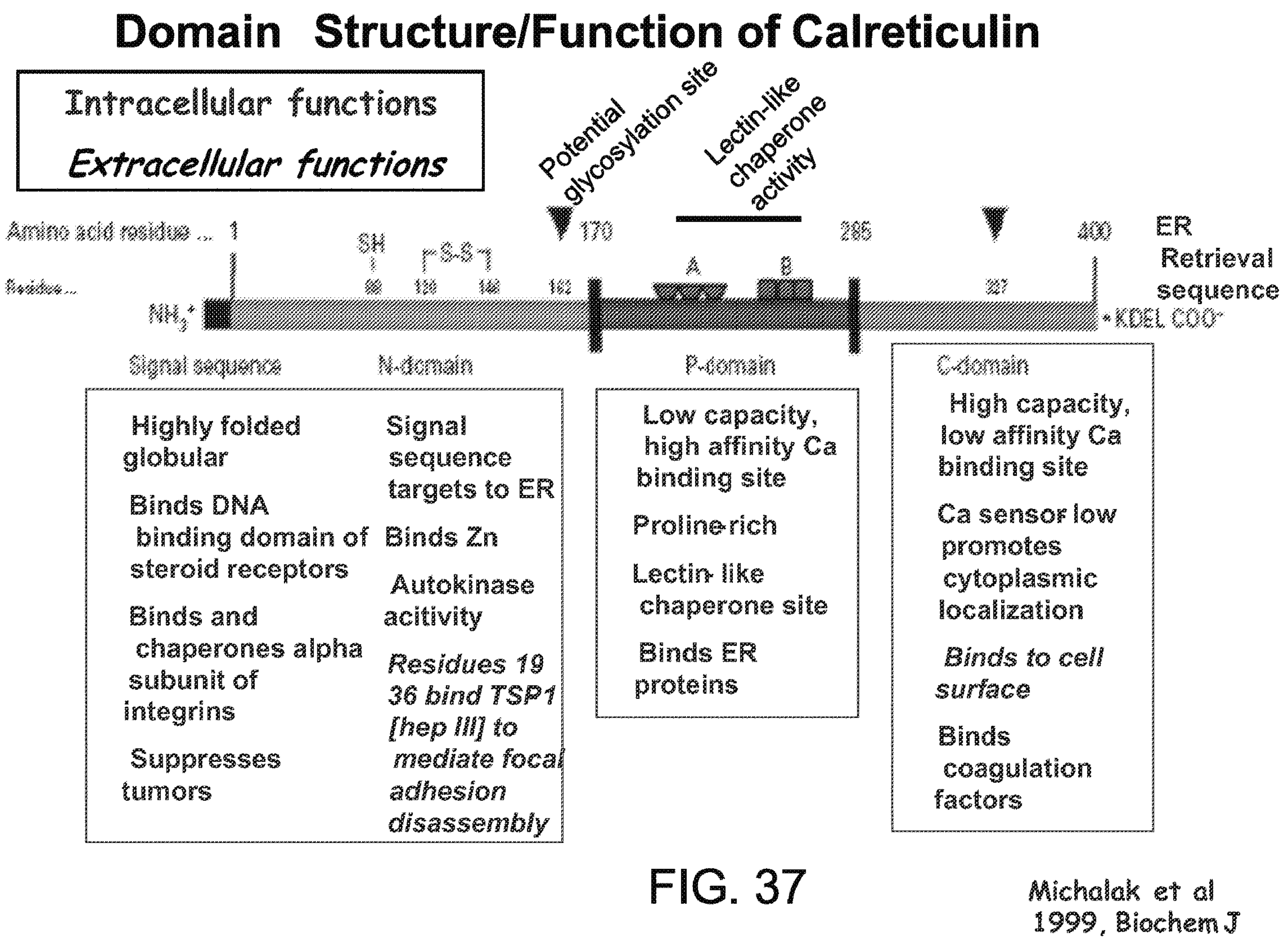

FIG. 37 shows the domain structure of calreticulin with designations of intracellular (normal type face) and the extracellular functions (italics).

Figure 38:
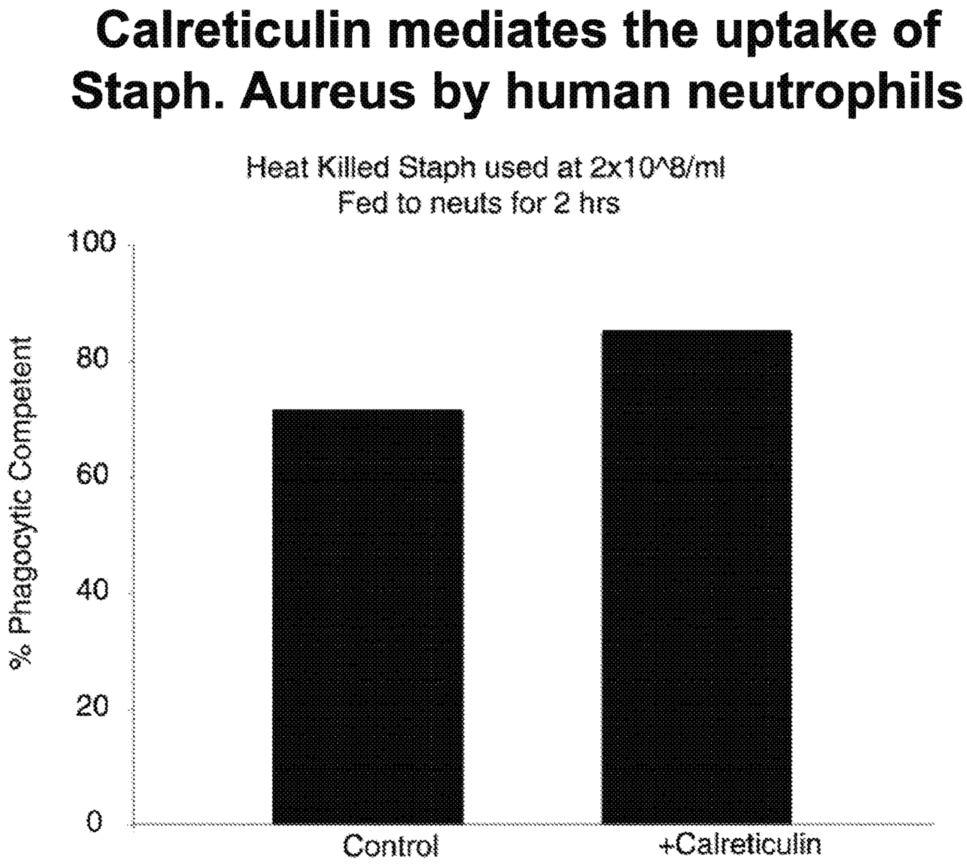

FIG. 38 shows a graph indicating that calreticulin enhances the phagocytosis of Staph Aureus by human polymorphonucleated neutrophils (PMNs).

DETAILED DESCRIPTION

Many factors contribute to wound healing deficiencies in individuals having impaired wound healing, including but not limited to chronic wounds or skin ulcers, such as decreased or impaired growth factor production, macrophage and immune cell infiltration and function (e.g., clearance of apoptotic cells, bacteria, and dead tissue), collagen accumulation, quantity of granulation tissue, keratinocyte and fibroblast migration and proliferation, and re-epithelization of the wound. See, e.g., Brem et al. (2007) J. Clin. Invest.; 117:1219-1222. Decreased macrophage infiltration explains the lack of cytokines and growth factors, wound remodeling, removal of dead cells, and vulnerability to infection. Histologically, chronic wounds, particularly diabetic wounds exhibit impairments in the remodeling of the dermis and are hypocellular, hypovascular, and show impaired ability to form granulation tissue. Because of these underlying problems, including inability to cope with bacterial infection, the wounds do not re-epithelialize properly and experience delayed or lack of closure. Further, diabetic fibroblasts show an inherently impaired ability to migrate and produce less VEGF (needed for neovascularization) than normal fibroblasts. Lerman et al., Am J Pathol 2003, 162:303-312).

According to the present invention, the inventors have surprisingly discovered that calreticulin improves several of the healing defects that prevent healing of a chronic wound including but not limited to a diabetic wound. In fact, calreticulin affects the most important functions required for general wound healing and tissue repair. According to the present invention, calreticulin induces matrix proteins including fibronectin and collagen and the factor, TGF-β3, which itself induces these matrix proteins and also elastin, proteoglycans, glycosaminoglycans, and perlecan and others. These qualities make calreticulin suitable and important for treating wrinkles and other cosmetic indications and also, for the treatment of deep tissue injury in which substantial removal of tissue or extensive tissue injury requires filling-in the wound defect or extensive tissue remodeling. In addition, calreticulin treatment facilitates the progression of chronic diabetic wound healing beyond the inflammatory phase, when these wounds are generally halted. Specifically, the present inventors have discovered that calreticulin induces monocyte, macrophage, fibroblast, and keratinocyte migration both in vitro and in vivo in a wound, induces cellular proliferation in the wound both in vitro and in vivo in a wound, and induces TGF-β3 both in vitro and in vivo in a wound. The TGF-β3 mammalian isoform is known for its anti-scarring effects (Ferguson, M. W. et al (2009) Lancet 373:1264-1274). Treatment of mouse excisional wounds in which all epidermal appendages were removed throughout the dermis indicated that calreticulin induced re-growth of hair follicles showing its potential fostering the regrowth of epidermal appendages following extensive and deep tissue injury when the entire depth of the dermis is removed. These previously unknown, multi-prong effects of calreticulin are unique among wound-healing agents and demonstrate that calreticulin is a new agent for the treatment of both acute wound injury and chronic wounds. Unexpectedly, the present inventors discovered that calreticulin improves healing of acute wound injury and chronic wounds even more efficiently than an FDA-approved healing agent, PDGF-BB (Regranex® gel).

The present invention also provides the use of calreticulin for treating wrinkles (including reducing the noticeability and/or improving the appearance and/or decreasing the depth of and/or decreasing the number of fine lines and/or wrinkles [including, e.g., facial lines and/or wrinkles, facial wrinkles on the cheeks, forehead, perpendicular wrinkles between the eyes, horizontal wrinkles above the eyes, and around the mouth, marionette lines, deep wrinkles or creases, expression lines, suborbital lines, periorbital lines, crow's feet, etc.] as well as preventing fibroblast senescence (aging) and more generally for tissue reconstruction including filling in and remodeling of defects or deformities in skin, vaginal reconstruction or other areas of the body in need of restoring normal anatomy, cartilage, bone as well as other uses of calreticulin disclosed herein. This ability of calreticulin is based, at least in part, on its ability to induce collagen, fibronectin and TGF-β3 (which, in turn, induces elastin and laminin and other matrix proteins). Calreticulin can be beneficially used in combination with hyaluronic acid as it occurs naturally in the body with hyaluronic acid with application to any needs or body parts described above.

In a related aspect, the present invention provides the use of calreticulin for prevention or treatment of cellular senescence and aging as in the treatment of wrinkles as well as other used of calreticuli disclosed herein.

As also disclosed herein, calreticulin can be used for treating corneal wounds (e.g., abrasions). This is based at least in part on calreticulin's unique ability to enhance healing without inducing angiogenesis. Angiogenesis in the cornea causes blindness.

As further provided herein, calreticulin can be used to treat epidermolysis bullosa. Calreticulin's ability to treat epidermolysis bullosa can be attributed at least in part to its ability to induce keratinocyte migration and proliferation which helps to resurface these broad pediatric wounds in which large areas of the epidermis are separated from the dermis appearing as large blisters.

In another aspect, this invention provides the use of clareticulin to treat surgical adhesions. Calreticulin's ability to treat surgical adhesions can be attributed at least in part to its ability to induce TGF-β3 which prevents scaring by mediating collagen organization. Calreticulin also decreases TGF-β1 and 2, which are known to cause scaring.

In yet another aspect, the invention provides the use of calreticulin to promote cartilage and bone repair. Calreticulin's ability to promote cartilage and bone repair can be attributed at least in part to its ability to induce chondrocytes to produce TGF-β3, collagen and other matrix proteins.

The human calreticulin protein has been previously described and cloned, and has protein accession number NP_004334 (SEQ ID NO:1) (Fliegel, L. et al. (1989) J. Biol. Chem. 264:21522-21528; Baksh, S. et al., (1991) J. Biol. Chem. 266:21458-21465; Rokeach, L. A. et al., (1991) Prot. Engineering 4:981-987; Baksh, S. et al. (1992) Prot. Express. Purific. 3:322-331; Michalak, M. et al., (1992) Biochem. J. 285:681-692; Obeid M, et al (2007) Nature Medicine 13:54-61; Tesniere A et al. (2008) Curr Opin Immunol 20:1-8; McCauliffe et al., J Clin Invest. 1990; 86:332). Calreticulin has an amino terminal signal sequence, a carboxy-terminal KDEL ER retrieval sequence, multiple calcium-binding sites, and harbors three distinct domains N, P, and C within its 46,000 dalton molecular mass (401 amino acids) (Michalak, M. et al. (1999) Biochem. J. 344: Pt 2:281-292). Novel extracellular functions of calreticulin continue to be unraveled, portraying a protein with strong impact on developmental, physiological, and pathological processes (Bedard, K. et al. supra; Sezestakowska, D. et al. supra.; Michalak (2009) et al. supra) Calreticulin is localized to the surface of a variety of cells including platelets, fibroblasts, apoptotic cells, endothelial cells, and cancer cells and is required for the phagocytosis of apoptotic cells by all phagocytes (Gardai, S. J. et al (2005) Cell 123:321-334). Therefore, calreticulin functions in the removal of dead cells and tissue from wounds (debridement). The presence of dead tissue in a wound is a significant deterrent to the wound healing process. The presence of bacterial infection is also a critical deterrent to the healing of an acute wound injury or a chronic wound. Calreticulin enhances the uptake and ingestion of Staph. Aureus by human neutrophils. This quality implicates a role for calreticulin as a bacteriacidal agent to fight infections in the wound bed. Calreticulin is also dynamically expressed during wound healing indicating its inherent importance in this process.

Definitions

"Treat" or "treatment" as used herein in connection with wound healing means improving the rate of wound healing or completely healing a wound. Methods for measuring the rate of wound healing are known in the art and include, for example, observing increased epithelialization and/or granulation tissue formation, or lessening of the wound diameter and/or depth. Increased epithelialization can be measured by methods known in the art such as by, for example, the appearance of new epithelium at the wound edges and/or new epithelial islands migrating upward from hair follicles and sweat glands. Granulation tissue is necessary for proper healing and for providing a scaffold for the migration of keratinocytes over the wound for resurfacing and for tissue remodeling including filling in the wound defect. The amount of area of granulation tissue formation can be measured by morphometric analysis by measuring the area of the granulation tissue or neodermis.

As used in connection with cosmetic applications to wrinkles, the terms "treat" or "treatment" mean reducing the noticeability and/or improving the appearance and/or decreasing the depth of and/or decreasing the number of facial lines and/or wrinkles, facial wrinkles on the cheeks, forehead, perpendicular wrinkles between the eyes, horizontal wrinkles above the eyes, and around the mouth, marionette lines, deep wrinkles or creases, expression lines, suborbital lines, periorbital lines, crow's feet, etc. as well as preventing fibroblast senescence (aging). Because of the ability of calreticulin to induce extracellular matrix proteins and stimulate cells such as fibroblasts and macrophages to migrate into the area of treatment such as in tissue reconstruction, these cells produce cytokines, growth factors, and other proteins that aid in filling in or replenishing the tissue in need of restoring, such as in tissue reconstruction.

"Chronic wound" as used herein means a wound that has not completely closed in eight weeks since the occurrence of the wound in a patient having a condition, disease or therapy associated with defective healing. Conditions, diseases or therapies associated with defective healing include, for example, diabetes, arterial insufficiency, venous insufficiency, chronic steroid use, cancer chemotherapy, radiotherapy, radiation exposure, and malnutrition. A chronic wound includes defects resulting in inflammatory excess (e.g., excessive production of Interleukin-6 (IL-6), tumor necrosis factor-alpha (TNF-$\alpha$), and MMPs), a deficiency of important growth factors needed for proper healing, bacterial overgrowth and senescence of fibroblasts. A chronic wound has an epithelial layer that fails to cover the entire surface of the wound and is subject to bacterial colonization, which can result in biofilm formation, which is resistant to treatment with anti-bacterial agents.

"Chronic diabetic wound" means a chronic wound in a patient with diabetes. A chronic diabetic wound may be associated with peripheral neuropathy and/or macro- and micro-vascular insufficiency. A diabetic foot ulcer is one type of chronic diabetic wound.

The term "hyaluronic acid" (HA) as used in the present application refers to hyaluronic acid or salts of hyaluronic acid, such as the sodium, potassium, magnesium and calcium salts, among others. The term "hyaluronic acid" is also intended to include not only elemental hyaluronic acid, but hyaluronic acid with other trace of elements or in various compositions with other elements, as long as the chemical and physical properties of hyaluronic acid remain unchanged. In addition, the term "hyaluronic acid" as used in the present application is intended to include natural formulas, synthetic formulas or combination of these natural and synthetic formulas. Non-limiting examples of useful hyaluronic acid preparations which can be used in the methods of the present invention include, for example, Juvederm® (a highly-crosslinked hyaluronic acid product sold by Allergan, Inc.) and RESTYLANE®, Perlane® (a non-animal stabilized hyaluronic acid product sold by Q-Med AB).

"Patient" or "subject" refers to mammals and includes human and veterinary subjects.

A "therapeutically effective amount" means the amount of a compound that, when administered to a mammal for treating a chronic diabetic wound, is sufficient to effect such treatment. The "therapeutically effective amount" may vary depending on the size of the wound, and the age, weight, physical condition and responsiveness of the mammal to be treated.

As used herein, the term "promote wound healing" is used to describe an agent that increases the rate at which a wound heals and the quality of wound repair.

The term "growth factor" can be a naturally occurring, endogenous or exogenous protein, or recombinant protein, capable of stimulating cellular proliferation and/or cellular differentiation and cellular migration.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

The term "calreticulin" and "CRT" are used interchangeably herein.

In accordance with the present invention there may be numerous tools and techniques within the skill of the art, such as those commonly used in molecular immunology, cellular immunology, pharmacology, microbiology, molecular biology, biochemistry, protein chemistry, and cell biology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

Preparation of Calreticulin

Methods for the preparation and analysis of calreticulin, such as tissue extraction, recombinant protein technology in bacteria or yeast, anion and cation exchange and hydrophobic interaction chromatography, alcohol precipitation, cellulose acetate electrophoresis, polyacrylamide gel electrophoresis (PAGE), measurement of protein concentration, and microanalysis of SDS-PAGE electroblotted protein reverse phase HPLC, mass spectrometry, are well known in the art and are described in detail in U.S. Pat. No. 5,591,716.

As a consequence of the process of producing proteins in bacteria, recombinant calreticulin is produced with amino acid residues at the N-terminus that are not present in natural calreticulin. As shown in the Examples below, the additional N-terminal residues do not interfere with the beneficial effects of calreticulin on chronic wound healing. Calreticulin molecules used in the experiments described in the Examples included the following:

(a) Recombinant human calreticulin having an N-terminus with an added histadine tag and two additional amino acids (GenWay Biotech, Inc., San Diego Calif.) ("GenWay CRT"). The histadine tag aids in the purification of the calreticulin on a nickel-Sepharose affinity column. The two additional amino acid residues between the N-terminal start methionine of calreticulin are glutamate and phenylalanine. The N-terminus of this "calreticulin+2 amino acids" has the amino acid sequence MHHHHHHHHEF (SEQ ID NO:3).

(b) Recombinant rabbit and human calreticulin having a histadine tag and five additional amino acids at the N-terminus of the natural rabbit and human CRT amino acid sequence (from M. Michalak, University of Alberta). Thus, one such recombinant calreticulin has a histadine tag and five additional amino acids at the N-terminus of the natural rabbit CRT, and another such recombinant calreticulin has a histadine tag and five additional amino acids at the N-terminus of natural human CRT. The additional amino acids are of the gene III sequence in the pBAD plasmid, which is used to direct calreticulin protein to the periplasmic space of *E. coli* for ease of isolation. The gene III sequence is 23 amino acids. The gene III sequence is cleaved by the *E. coli* to produce a CRT with 5 amino acids at the N-terminus. This CRT+his tag+5 amino acids molecule is referred to herein as "Michalak 5 CRT+ tag." The Michalak 5 CRT N-terminus has the amino acid sequence MHHHHHHHHTMELE (SEQ ID NO:4). Natural (non-recombinant) human calreticulin has the amino acid sequence represented in SEQ ID NO:1. The amino acid sequence for natural rabbit calreticulin is represented by SEQ ID NO:7.

(c) Recombinant rabbit and human calreticulin having a histadine tag and 23 additional amino acids at the N-terminus of the natural rabbit (SEQ ID NO:7) and human (SEQ ID NO:1) CRT amino acid sequence (from M. Michalak, University of Alberta). Thus, one such recombinant calreticulin has a histadine tag and 23 additional amino acids at the N-terminus of the natural rabbit CRT, and another such recombinant calreticulin has a histadine tag and 23 additional amino acids at the N-terminus of natural human CRT. This CRT+his tag+23 amino acids molecule is referred to herein as "Michalak 23 CRT+ tag." The Michalak 23 CRT N-terminus has the amino acid sequence MHHHHHHHH-MKKLLFAIPLVVPFYSHSTMELE (SEQ ID NO:5), (d) Recombinant rabbit and human calreticulin having five additional amino acids at the N-terminus of the natural rabbit and human CRT amino acid sequence (from M. Michalak, University of Alberta). Thus, one such recombinant calreticulin has a five additional amino acids at the N-terminus of the natural rabbit CRT, and another such recombinant calreticulin has five additional amino acids at the N-terminus of natural human CRT. The additional amino acids are of the gene III sequence in the pBAD plasmid, which is used to direct calreticulin protein to the periplasmic space of *E. coli* for ease of isolation. This CRT+his tag+5 amino acids molecule is referred to herein as "Michalak 5 CRT." The Michalak 5 CRT N-terminus has the amino acid sequence TMELE (SEQ ID NO:8). Natural (non-recombinant) human calreticulin has the amino acid sequence represented in SEQ ID NO:1. The amino acid sequence for natural rabbit calreticulin is represented by SEQ ID NO:7.

(e) Recombinant rabbit and human calreticulin having 23 additional amino acids at the N-terminus of the natural rabbit (SEQ ID NO:7) and human (SEQ ID NO:1) CRT amino acid sequence (from M. Michalak, University of Alberta). Thus, one such recombinant calreticulin has 23 additional amino acids at the N-terminus of the natural rabbit CRT, and another such recombinant calreticulin has 23 additional amino acids at the N-terminus of natural human CRT. This CRT+23 amino acids molecule is referred to herein as "Michalak 23 CRT." The Michalak 23 CRT N-terminus has the amino acid sequence MKKLLFAIPLV-VPFYSHSTMELE (SEQ ID NO:9), and (f) Natural dog pancreas calreticulin ("NAT-CRT"). The amino acid sequence of NAT-CRT is represented by SEQ ID NO:6.

The present invention encompasses calreticulin peptide fragments and other functional derivatives of calreticulin which have the functional activity of promoting healing of a chronic wound or the function of affecting a process associated with enhancing acute wound healing and chronic or impaired wound healing or tissue repair.

In an embodiment, the invention provides "functional derivatives" of calreticulin. By "functional derivative" is meant a "fragment," "variant," "analog," or "chemical derivative" of calreticulin. A functional derivative retains at least a portion of the function of calreticulin, such as the activity of promoting chronic wound healing, upregulating TGF-β3 expression in skin, inducing cell migration, stimulating cell proliferation, or binding to a specific anti-calreticulin antibody, which permits its utility in accordance with the present invention. A "fragment" of calreticulin refers to any subset of the molecule, that is, a shorter peptide. A "variant" of calreticulin refers to a molecule substantially similar to either the entire protein or a fragment thereof. Variant peptides may be conveniently prepared by direct chemical synthesis of the variant peptide or producing the peptide by genetic recombinant technology, using methods well-known in the art.

It will be understood that the protein useful in the methods and compositions of the present invention can be biochemically purified from a cell or tissue source. For preparation of naturally occurring calreticulin, any of a number of tissues of adult or of fetal origin can be used. Because the gene encoding human calreticulin is known (GenBank Accession No. NC_000019.8, (SEQ ID NO: 2); Fliegel et al., supra; Baksh et al., (1991) supra; Rokeach et al., supra; Baksh et al. (1992) supra; Michalak et al., (1992), supra); McCauliffe et al., J Clin Invest. 1990; 86:332) and can be isolated or synthesized, the polypeptide can be synthesized substantially free of other proteins or glycoproteins of mammalian origin in a prokaryotic organism, in a non-mammalian eukaryotic organism, by a yeast, or by a baculovirus system, if desired. Alternatively, methods are well known for the synthesis of polypeptides of desired sequence on solid phase supports and their subsequent separation from the support.

Alternatively, amino acid sequence variants of the protein or peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired functional activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., DNA 2:183 (1983)) of nucleotides in the DNA encoding the calreticulin protein or a peptide fragment thereof, thereby producing DNA encoding the variant, and thereafter expressing the DNA (cDNA, RNA, and protein) in recombinant cell culture (see below). The variants typically exhibit the same qualitative biological activity as the nonvariant peptide.

A preferred group of variants of calreticulin are those in which at least one amino acid residue in the protein or in a peptide fragment thereof, and preferably, only one, has been removed and a different residue inserted in its place. For a detailed description of protein chemistry and structure, see Schulz, G. E. et al., PRINCIPLES OF PROTEIN STRUCTURE, Springer-Verlag, New York, 1978, and Creighton, T. E., PROTEINS: STRUCTURE AND MOLECULAR PROPERTIES, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1-2 of Schulz et al. (supra) and FIGS. 3-9 of Creighton (supra). Based on such an analysis, conservative substitutions are defined herein as exchanges within one of the following five groups:

1. Small aliphatic, nonpolar or slightly polar residues: Ala, Ser, Thr (Pro, Gly);

2. Polar, negatively charged residues and their amides: Asp, Asn, Glu, Gln;

3. Polar, positively charged residues: His, Arg, Lys;

4. Large aliphatic, nonpolar residues: Met, Leu, Ile, Val (Cys); and

5. Large aromatic residues: Phe, Tyr, Trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note the Schulz et al. would merge Groups 1 and 2, above. Note also that Tyr, because of its hydrogen bonding potential, has some kinship with Ser, Thr, etc.

Preferred deletions and insertions, and substitutions, according to the present invention, are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays which are described in more detail below. For example, a change in the immunological character of the protein peptide molecule, such as binding to a given antibody, is measured by a competitive type immunoassay. Biological activity is screened in an appropriate bioassay, as described below.

Modifications of such peptide properties as redox or thermal stability, hydrophobicity, susceptibility to proteolytic degradation or the tendency to aggregate with carriers or into multimers are assayed by methods well known to the ordinarily skilled artisan.

An "analog" of calreticulin refers to a non-natural molecule substantially similar to either the entire molecule or a fragment thereof.

A "chemical derivative" of calreticulin contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Additionally, modified amino acids or chemical derivatives of amino acids of calreticulin or fragments thereof, according to the present invention may be provided, which polypeptides contain additional chemical moieties or modified amino acids not normally a part of the protein. Covalent modifications of the peptide are thus included within the scope of the present invention. The following examples of chemical derivatives are provided by way of illustration and not by way of limitation.

Aromatic amino acids may be replaced with D- or L-naphthylalanine, D- or L-phenylglycine, D- or L-2-thienylalanine, D- or L-1-, 2-, 3- or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl) alanine, and D- or L-alkylalanine where alkyl may be substituted or unsubstituted methyl, ethyl, propyl, hexyl, butyl, pentyl, isopropyl, isobutyl, sec-isotyl, isopentyl, non-acidic amino acids, of chain lengths of C1-C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (for example, $—SO_3H$) threonine, serine, tyrosine.

Other substitutions may include unnatural hydroxylated amino acids may made by combining "alkyl" with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (for example, containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage the polypeptides can be replaced by a ketomethylene moiety. Such derivatives are expected to have the property of increased stability to degradation by enzymes, and therefore possess advantages for the formulation of compounds which may have increased in vivo half lives, as administered by various routes as described herein.

In addition, any amino acid representing a component of the peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by various routes.

Additional amino acid modifications in calreticulin or in a peptide thereof may include the following.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-13-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides, which reverses the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; 0-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine c-amino group.

The specific modification of tyrosyl residues has been studied extensively with particular interest in introducing spectral labels into tyrosyl residues by reaction with aromatic diazonium compounds or tetranitromethane. Most commonly, N-acetylimidizol and tetranitromethane are used to form 0-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidyl-propionate), and bifunctional maleimides such as bis-N-maleimido-1,8-octane. Derivatizing agents such as methyl-3-[(p-azidophenyl)dithic]propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the α-amino groups of lysine, arginine, and histadine side chains (Creighton, supra), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in Remington's Pharmaceutical Sciences, 16th ed., Mack Publishing Co., Easton, Pa. (1980).

Production of Calreticulin and Fusion Proteins that Promote Wound Healing

Calreticulin may be purified from a tissue source using conventional biochemical techniques, or produced recombinantly in either prokaryotic or eukaryotic cells using methods well-known in the art. See, Sambrook, J. et al., MOLECULAR CLONING: A LABORATORY MANUAL, 2nd Edition, Cold Spring Harbor Press, Cold Spring Harbor, N.Y., 1989, which reference is hereby incorporated by reference in its entirety. Various references describing the cloning and expression of calreticulin have been noted above.

Fusion proteins representing different polypeptide regions in calreticulin may be used to identify regions of the protein that have the desired functional activity (binding, stimulating wound healing, specific functions associated with wound healing, etc.). When combined with the polymerase chain reaction (PCR) method, it is possible to express in bacteria nearly any selected region of the protein.

Calreticulin, a fragment peptide thereof, or a fusion protein thereof may also be expressed in insect cells using baculovirus expression system. Production of calreticulin or functional derivatives thereof, including fusion proteins, in insects can be achieved, for example, by infecting the insect host with a baculovirus engineered to express calreticulin by methods known to those of skill. Thus, in one embodiment, sequences encoding calreticulin may be operably linked to the regulatory regions of the viral polyhedrin protein. See, Jasny, 1987, Science 238:1653. Infected with the recombinant baculovirus, cultured insect cells, or the live insects themselves, can produce the calreticulin or functional derivative protein in amounts as great as 20 to 50% of total protein production. When live insects are to be used, caterpillars are presently preferred hosts for large scale production according to the invention.

Fragments of calreticulin are purified by conventional affinity chromatography using antibodies, preferably monoclonal antibodies (mAbs) that recognize the appropriate regions of calreticulin. The mAbs specific for the most highly conserved regions in calreticulin can be used to purify calreticulin protein from mixtures.

Routes of Administration and Dosages

The preferred animal subject of the present invention is a mammal. By the term "mammal" is meant an individual belonging to the class Mammalia. The invention is particularly useful in the treatment of human subjects.

The present invention provides for methods of treatment of wounds, and cosmetic applications of calreticulin, which methods comprise administering to a subject in need of such treatment a therapeutically effective amount of calreticulin, or a functional derivative thereof. The disorders that may be treated according to this invention include, but are not limited to acute wounds, chronic wounds, corneal wounds, bone and cartilage repair, injury due to surgical procedures, wrinkles, and alopecia as well as other uses of calreticulin disclosed herein.

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

For the topical applications, it is preferred to administer an effective amount of a composition according to the present invention to an affected wound area, in particular the skin surface and/or wound bed surface. This amount will generally range from about 0.001 mg to about 1 g per application, depending upon the area to be treated, the severity of the symptoms, and the nature of the topical vehicle employed. In one embodiment, the topical preparation is an ointment wherein about 0.01 to about 50 mg of active ingredient is used per cc of ointment base. The dosage of the therapeutic formulation may vary widely, depending upon the size of the wound, the patient's medical history, the frequency of administration, the manner of administration, the clearance of the agent from the host, and the like. The dose may be administered with each wound dressing change. The dose may be administered once daily, more than once daily, or as infrequently as weekly or biweekly.

Calreticulin may be administered in any pharmaceutically acceptable carrier or excipient. The term "carrier" refers to a diluent, adjuvant, excipient, or vehicle with which the compound is administered. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. Pharmaceutically acceptable carriers can be sterile liquids, such as water and oils, including those of petroleum, animal, vegetable or synthetic origin, such as peanut oil, soybean oil, mineral oil, sesame oil and the like. Others are gels, such as hydrogels, hyaluronic acid (HA), collagen, materials consisting of naturally occurring or synthetic substances, or any other matrix protein such as perlecan, proteoglycans, glycoaminoglycans, fibrin gels, and polymers. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

In an embodiment of the invention, peptide sequences from calreticulin are inserted into or replace sequences within "scaffold" proteins. Accordingly, a "scaffold protein" of the present invention is a protein which includes a functional calreticulin sequence, either as an inserted sequence or as a replacement sequence for a homologous (corresponding) sequence of the scaffold protein. The scaffold protein adopts a native conformation. The calreticulin and scaffold can alternate positions; these terms are used to indicate the source of sequences introduced into the "scaffold." In other embodiments of the invention, functional peptide sequences from calreticulin can be inserted into a chemical or natural matrix.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol. 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

The administration route may be any mode of administration known in the art, including but not limited to topically, subcutaneously (e.g., by injection), intradermally, transdermally (e.g., by transdermal patch), via intracorporal application during surgery, parenterally, intramuscularly, intraperitoneally, buccally, intravenously, intrathecally, intracranially, by injection into involved tissue, intraarterially, orally, or via an implanted device. The present invention also provides pharmaceutical and cosmetic compositions comprising an amount of calreticulin, or a functional derivative or fragment thereof, effective to promote the healing of a wound or exert any other therapeutic or cosmetic effect relevant for the present invention, in a pharmaceutically or cosmetically acceptable carrier.

The pharmaceutical composition of the present invention is preferably applied to site of action (e.g., topically, subcutaneously [e.g., by injection], intradermally, transdermally [e.g., by transdermal patch], or via intracorporal application during surgery).

For topical application, the compositions of the present invention may be incorporated into topically applied vehicles such as salves or ointments, which have both a soothing effect on the skin as well as a means for administering the active ingredient directly to the affected area.

The carrier for the active ingredient in a topical formulation may be either in sprayable or non-sprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like. A preferred vehicle is a petroleum/lanolin vehicle.

Also suitable for topic application are sprayable aerosol preparations wherein the active ingredient, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

The dosage administered will be dependent upon the age, health, and weight of the recipient, kind of concurrent treatment, if any, frequency of treatment, and the nature of the effect desired.

Effective doses of calreticulin for therapeutic uses discussed above may be determined using methods known to one skilled in the art. Effective doses may be determined, preferably in vitro, in order to identify the optimal dose range using any of the various methods described herein. In one embodiment, an aqueous solution of a calreticulin protein or peptide is administered by intravenous injection. Each dose may range from about 0.001 μg/kg body weight to about 100 mg/kg body weight, or more preferably, from about 0.1 μg/kg to 10 mg/kg body weight. The dosing schedule may vary from one time only to once a week to daily or twice (or more) daily depending on a number of clinical factors, including the type of wound, its severity, and the subject's sensitivity to the protein. Non-limiting examples of dosing schedules are 3 μg/kg administered twice a week, three times a week or daily; a dose of 7 μg/kg twice a week, three times a week or daily; a dose of 10 μg/kg twice a week, three times a week or daily; or a dose of 30 μg/kg twice a week, three times a week or daily. In the case of a more severe chronic wound, it may be preferable to administer doses such as those described above by alternate routes, including intravenously, intramuscularly, intraperitoneally or intrathecally. Continuous infusion may also be appropriate.

Calreticulin or a functional derivative may also be administered in combination with an effective amount of at least one other agent that is, itself, capable of promoting the healing of wounds or treating accompanying symptoms. Such agents include growth factors, anti-infectives, including anti-bacterial, anti-viral and anti-fungal agents, local anesthetics, and analgesics, collagens, fibrin gels, glycosaminoglycans (e.g., hyaluronic acid), proteoglycans (e.g., perlecan, heparin sulfate), syndecan, suitable chemical or natural polymers, or a combination thereof. Other agents that can be applied to a wound include but, are not limited to, calreticulin as part of a living skin substitute (skin device) or a synthetic, chemical or natural scaffold or matrix or polymer thereof.

Combination treatment according to the present invention includes administering the calreticulin and one or more additional agent in the same or separate dosage forms. Such additional agents include, among others, agents which are known to promote wound healing or to treat problems or symptoms associated with chronic wounds. Examples of such agents include hyaluronic acid, disinfectants such as antibacterial agents or antiviral agents, anti-fungal agents, anti-inflammatory agents, agents which induce relief from pain or itching, and the like. Also included are growth factors which promote wound healing, including, but not limited to, transforming growth factor-α, transforming growth factor-β, fibroblast growth factor-a, fibroblast growth factor-β, FGFs in general, epidermal growth factor, platelet-derived growth factor, endothelial cell-derived growth factor, insulin-like growth factors, VEGF, and granulocyte colony-stimulating factor. In accordance with the methods of the present invention, calreticulin administered in combination with an additional agent includes any overlapping or sequential administration of the calreticulin and the additional agent. Thus, for example, methods according to the present invention encompass administering calreticulin and an additional agent simultaneously or non-simultaneously.

Further, according to the present invention, calreticulin and an additional agent can be administered by the same route (e.g., both are administered topically) or by different routes (e.g., calreticulin is administered topically and an additional agent is administered orally).

The pharmaceutical compositions of the present invention may be administered by any means that achieve their intended purpose. Amounts and regimens for the administration of calreticulin, or a derivative thereof, can be determined readily by those with ordinary skill in the clinical art of treating wounds.

EXAMPLES

The following Examples illustrate the present invention, but are not limiting. Throughout the specification, the positive control reagent may be interchangeably referred to as either Regranex® gel or PDGF-BB. These two terms are understood to be the same reagent used in the porcine wound healing studies. VEGF was used as a positive control in the murine wound healing studies.

Materials and Methods

Recombinant rabbit calreticulin (from M. Michalak, University of Alberta) was expressed in *E. coli* as a his-tagged protein that was purified to homogeneity by Nickel-Sepharose chromatography. The rabbit calreticulin was shown to be properly folded and migrated as a single band at approximately Mr 50,000 by SDS-PAGE, as described in Guo et al., J Biol Chem. 2003; 278:50645-50653. This protein was prepared in pBAD and *E. coli*, and his tagged with five amino acids at the N-terminus (composed of SEQ iD NO:5 and SEQ ID NO:7). Subsequent to these experiments, human calreticulin was produced from the human gene sequence inserted into the pBAD plasmid and expressed in *E. coli*. The recombinant human calreticulin was found to be a mixture of Michalak 5-CRT+ tag and Michalak 23-CRT+ tag (later experiments were performed using Michalak 5-CRT and Michalak 23-CRT). In addition, human calreticulin was obtained from GenWay Biotech (#10-288-22432F; San Diego, Calif.). The calreticulin was stored at minus 80 C in 10 mM Tris containing 3.0 mM calcium, pH 7.0 ("buffer"), to maintain proper conformation of this calcium-binding molecule. Anti-peptide antibodies (purified IgG) specific for each isoform of TGF-β (TGF-β1, TGF-β2, AND TGF-β3) have been described by Levine et al., Amer J Pathol. 1993; 143:368-380; Pelton et al. J Cell Biol. 1991; 115:1091-1105. Isoform-specific cytokeratin 14 antibody was obtained from Accurate Scientific (Westbury, N.Y.). Goat anti-calreticulin (pantropic; BIOCAN/Jackson Immunochemicals) was a gift from M. Michalak (University of Alberta). Rabbit anti-human Ki-67 was obtained from Nova Castra Laboratories Ltd. (Newcastle, UK) and a monoclonal mouse anti-human antibody specific for macrophages (MAC387) was obtained from Serotec, Ltd. (UK).

Collagen type I antibody was purchased from Santa Cruz Biotech, catalogue no. sc-28657 (Santa Cruz, Calif.). Integrin α-5 antibody was purchased from Santa Cruz Biotech, catalogue no. sc-10729 (Santa Cruz, Calif.). Integrin β-1 antibody was purchased from Santa Cruz Biotech, catalogue no. sc-8978 (Santa Cruz, Calif.). Alpha smooth muscle actin antibody was purchased from Sigma-Aldrich, catalogue no. A5228 (St. Loius, Mo.).

Porcine Model of Diabetic Wound Healing

The following porcine wound models and treatments were used in the experiments described in the examples. Porcine wound healing is a well-known and accepted model for studying human wound healing because the pig heals similarly to humans. For example, porcine and human skin share similar epidermal and dermal-epidermal thickness ratios, mosaic hair growth, and have similar hair and blood vessel distribution. In addition, like humans, pigs lack the muscular layer (panniculous carnosus) found in loose skin animals (e.g., rodents), which contracts the wound. Adolescent Yorkshire pigs weighing about 50-60 lbs. were housed, fed and treated in accordance with protocols approved by the IACUC at Vanderbilt University Medical Center. Prior to surgery, the pigs were anesthetized with a mixture of Ketamine anesthetic (2.2 mg/kg), Telazol® anesthetic/tranquilizer (4.4 mg/kg) and Xylazine anesthetic (2.2 mg/kg) by intramuscular injection, intubated and maintained on an inhalation of oxygen and isofluorene. Cefazolin antibiotic was administered intramuscularly immediately before surgery and on subsequent post-operative days. Using sterile technique, four longitudinal partial thickness wounds were created along the paravertebral region to a depth of 1560 μm using a Zimmer dermatome (Warsaw, Ind.). A series of 1.5 inch×1.5 inch non-meshed skin graft bridges secured by staples separated the area into individual excisional partial thickness wounds. Calreticulin at 1.0 mg/ml and 5.0 mg/ml was topically applied to the wounds. The treated wound tissue was harvested at 5 and 10 days after wounding. The wounds were made in reverse order so that the harvesting would occur at the same time. Thus, one-half of the wounds were created at the onset of the experiment and the remaining wounds were created 5 days later so that each animal was euthanized on the 10th day following wounding (n=6 wounds per parameter studied).

The gel formulation Regranex (0.01% PDGF-BB; Ethicon, Inc., Sommerville, N.J.), a commercially available wound healing agent, was used as a positive control. Two wounds per treatment group per pig were used. In order to prevent the liquid from rolling off, 0.05 ml of calreticulin or buffer was applied to the pig lying on its side and allowed to dry for one minute prior to application of a KY gel formulation, which maintained moist wound healing conditions. The wounds were covered with OpSite™ (Smith & Nephew, Mt Waverly, Victoria, Australia) semi-occlusive bandages. The wounds were cleansed daily; and the bandages were replaced. Buprenex analgesic was administered intramuscularly for pain control in the initial post-operative period. Duragesic® patches 25 μg/hr (transdermal fentanyl) were placed for 3 days for sustained analgesia. Topical treatments of calreticulin and buffer controls were repeated daily for the first 4 days; PDGF-BB was applied once at the time of wounding. To control for possible effects of wound location on the rate of healing, wound placement patterns from the various treatment groups were randomized.

As a model for diabetes-impaired wound healing, pigs were administered 1 mg/kg of methylprednisolone acetate (DepoMedrol, Henry-Schein, Melville, N.Y.) intramuscularly 48 hours before wound creation. The wounds were prepared and treated as described above. Treatment groups were the same for both the normal and impaired healing models. Animals were euthanized and tissues collected for study after 6 days or 7 days of healing.

Murine Model of a Chronic Diabetic Wound

In these experiments, animal studies of impaired diabetic wound healing were performed in mice, using a marine model described by Galiano et al. Galiano, R. D., et al. (2004) Am. J. Pathol. 2004, 164:1935-1947; Galiano, R. D. et al. (2004) Wound Repair and Regeneration; 12:485-492. This model allowed for minimal contraction of the wound, requiring it to heal via granulation tissue formation and re-epithelialization as in human wounds. Mice heal via contraction of the wounds, specifically through the effects of their panniculous carnosus. The panniculus carnosus is the muscle layer under the skin on loose-skinned hairy animals that allows for contraction of dermal wounds. This model eliminated this effect by stenting open the wound to prevent this contraction, thus facilitating observations of re-epithelialization and enabling measurement of the area of wound resurfacing over time during wound healing (reduction in epithelial gap between the edges of the wound) this model mimics human cutaneous wound healing more closely. Therefore, all healing in this murine model was mediated by granulation tissue formation and epithelial migration, more closely mimicking human skin wound healing.

Eight- to 12-week old C57BL/6J mice (Jackson Laboratories stock #000664, Bar Harbor, Me.) were used as a control of unimpaired healing; db/db mice (BKS.Cg-m+/+ Leprdb, Jackson Laboratories stock #000642) were used in the model of impaired wound healing. The db/db mice are leptin receptor deficient and are a model of type II diabetes mellitus characterized by hyperglycemia, obesity, hypoinsulinemia, and impaired wound healing. The animals were housed five animals per cage prior to surgery and alone post-procedure in a temperature-controlled animal facility with a 12-hour light/dark cycle. The mice were acclimated to their environment for at least 1 week prior to the procedure and were given food and water ad libitum. This experimental protocol was approved by the Institutional Animal Care and Use Committee (IACUC) of New York University School of Medicine. The animals utilized in this experiment all received humane care.

Wound Model:

Mice were individually anesthetized using an intraperitoneal injection of ketamine (75 mg/kg), xylazine (15 mg/kg), and acepromazine (2.5 mg/kg). The dorsal surface was shaved with an electric clipper followed by a depilatory agent to remove any remaining hair. The mice were rinsed with an alcohol swab and sterilely prepped with betadine and draped. A sterile 6 mm punch biopsy tool was used to outline a pattern for the wounds on the dorsum of the C57/BL6J and db/db mice. A 6 mm wound was chosen for the db/db mice because of their large dorsal surface. Two wounds were patterned, one on each side of midline. Full-thickness wounds extending through the panniculus carnosus and entire dermis were made using an Iris scissor. A donut-shaped splint (as shown in FIG. 33A) with a diameter twice the size of the wound was cut from a 0.5 mm-thick silicone sheet (Grace Bio-Laboratories, Bend, Oreg.). The splint was placed so that the wound was centered within the splint. An immediate-bonding adhesive (Krazy Glue®; Elmer's Inc., Columbus, Ohio) was used to fix the splint to the skin followed by interrupted 6-0 nylon sutures (Ethicon, Inc., Somerville, N.J.) to ensure positioning.

After wounding, 10 μL calreticulin (5.0 mg/mL) in 10 mM Tris containing 3 mM calcium was applied to each wound for the first four days of the experiment. The buffer alone was used on the control animals. After treatment, the wounds were covered in an occlusive dressing (Tegaderm™, 3M, St. Paul, Minn.) to protect them from infection and trauma. The animals were placed in individual cages under a warming lamp and allowed to recover fully from anesthesia. The dressing was changed daily after each calreticulin or buffer application.

Wound Analysis:

Time to Closure:

Digital photographs were taken on the day of surgery and every day thereafter. Time to closure was defined as the time at which the wound bed was completely filled in with new tissue and fully closed. The wound area was analyzed by tracing the wound margin with a fine-resolution computer mouse and calculating pixel area using SigmaScan® Pro Image Analysis Version 5.0.0 digital analysis software (Aspire Software International, Leesburg, Va.). The wound area was calculated as a percent of the original wound area. A completely closed wound was considered equal to its area measured zero (grossly). Because the splint has a constant area, it was used to normalize the wound sizes.

Epithelial Gap and Granulation Tissue by Histological Observation:

The mice were euthanized on days 2, 7, 10, 14, and 28 (n=6 for each group). The wounds were excised, bisected, and fixed in 10% neutral formalin for 24 hours. The sections were embedded in paraffin and sectioned transversely through the wound bed, allowing for analysis of the epithelial gap remaining and wound depth to be calculated. The samples underwent routine histological processing with hematoxylin and eosin. Under light microscopy, the sections were photographed using a mounted digital camera (Olympus, Melville, N.Y.). The images were analyzed for epithelial gap (EG) and total area of granulation tissue (GT) using digital analysis software. For EG and GT formation, the data was measured in pixels and presented as a mean +/− standard error with units of pixels (distance), pixels$^2$ (area) as units, respectively. EG was defined as the distance in area of non-epithelialized wound between the advancing edges of keratinocyte (epithelial cell) migration to close the wound. Three serial sections were averaged to determine EG at each time point. An EG of zero represents a completely re-epithelialized wound. Area of GT was calculated by tracing regions of GT and calculating pixel area. (Note: A wound is re-epithelialized by light microscopy whereas wound closure indicates that the skin has completely closed.)

Histological Preparation of the Porcine Wounds

The methods for histological preparation and morphometric analysis used in the Examples are as follows. At the termination of each experiment, wounds with an adjacent margin of normal skin were excised, divided vertically into three full-thickness tissue sections per wound, fixed in 10% neutral buffered formalin for 24 hours, embedded in paraffin, and mounted in 5.0 μm thick tissue sections on glass slides for histological analysis and immunohistochemistry (IHC). The tissue sections were stained (described below) and the extent of re-epithelialization and dermal depth (granulation tissue formation) of the wounds was determined by morphometric analysis. Serial images of the wounds were captured under a light microscope and displayed on a videoscreen using an Olympus model AHBT camera. Quantitative measurements were performed using Image-Pro Plus scientific image analysis software (Media Cybernetic, Inc., Silver Spring, Md.).

Morphometric Analysis

Re-epithelialization was assessed using the wounds of normal pigs. Antibodies to cytokeratin 14 were used to selectively highlight the newly resurfaced epithelial islands and epidermal margins. The extent of re-epithelialization was determined after 5 days of healing in normal pigs by measuring a composite of newly resurfaced epidermis that migrated over the wounds from the wound edges and epithelial islands derived from surviving epithelium that migrated upward from hair follicles and sweat ducts, compared to total wound length. The data are expressed as a percent of resurfacing as described in Okwueze et al., J Invest Dermatol. 2007; 127:1030-1041.

Granulation tissue thickness was measured in trichrome stained tissue slides extending from the non-re-epithelialized surface of the granulating wound down to its intersection with the underlying unwounded dermis. The granulation tissue becomes converted into a neodermis as re-eptithelialization is nearly complete, which is measured as dermal depth. Dermal depth measurements extend from the dermo-epidermal junction down to the intersection of the newly formed granulation tissue with the adjacent underlying unwounded dermis of these partial thickness wound beds. To determine the average thickness of the granulation tissue at 5 days of healing or dermal depth at 10 days of healing in the normal pigs, and 6-7 days in the steroid-challenged pigs (diabetic model), five or greater random areas were measured in micron units as described in Okwueze et al., J Invest Dermatol. 2007; 127:1030-1041. The data are expressed as means +/− SEM.

Assay for Wound-Breaking (Tensile) Strength:

The effect of calreticulin on wound breaking strength was performed using a rat incisional model as described in Ballas et al., Wound Repair Regen. 2001; 9:223-237. Four full-thickness linear incisional wounds (3 cm in length) were created in the dorsal skin of each rat. After achieving hemostasis, the edges of the wounds were approximated with EX clips (Braintree Scientific, Braintree, Mass.) and the wound incisions on each rat were treated with calreticulin at 5.0 mg/ml and 10 mg/ml, buffer alone, or Regranex®. The rats were sacrificed at 7, 14, 21 and 28 days (n=10 rats per parameter per time point). Strips of skin, 1.0 cm×5.0 cm in length, perpendicular to the incision line were clamped into an Instron Tensiometer (Canton, Mass.) and tensile strength (breaking strength/cross-sectional area) was determined.

Immunohistochemical Analysis of Porcine and Murine Wounds:

Calreticulin Expression:

The temporal and spatial expression of calreticulin during wound healing was determined at 5 and 10 days of healing by immunohistochemical localization using a polyclonal goat anti-calreticulin. Slides were baked overnight at 56° C. and passed through graded alcohol with the final concentration being 30% ethanol. The slides were placed in Tris-buffered saline (TBS) containing 0.3% Triton X-100 for 15 minutes, followed by 100% methanol for one minute and then, peroxidase activity was quenched with 0.6% $H_2O_2$ for 30 minutes followed by 100% methanol for one minute. The tissues were blocked with normal rabbit serum (Vector Labs, #S5000; Burlingame, Calif.) in TBS containing 0.5% BSA (blocking buffer) for 20 minutes at room temperature. The calreticulin antibody, diluted at 1:1000 buffer, was incubated with the slides overnight at 4° C., in humido. After washes with TBS containing 0.1% BSA, biotinylated rabbit anti-goat IgG secondary antibody (Vector #BA5000) was applied to the slides for one hour at room temperature. The slides were washed and then incubated with ABC Reagent (Vectastain kit #PK6200, Vector Laboratories, Burlingame, Calif.) for one hour. After rinsing, the slides were dipped in the substrate 0.05 3,3-diaminobenzidine HCL (DAB; Sigma Chemical #D5637) solution until a brown color appeared, counterstained with hematoxylin (Fisher #CS401-1D), dehydrated through increasing concentrations of alcohol, and mounted with Permount (Fisher #SP15-100).

TGF-β Isoform Expression:

To determine whether TGF-β isoform expression was induced in calreticulin-treated porcine and murine wounds, tissue slides were incubated separately with antibodies to TGF-β1, TGF-β2, and TGF-β3. The antisera was produced in rabbits to individual peptides of each isoform and the IgG purified by peptide affinity chromatography as described in Felton et al., J Cell Biol. 1991; 115:1091-1105. Slides were treated as described above, except that prior to blocking with goat serum (Vector Labs, #S-1000) the tissue sections were treated with hyaluronidase (1.0 mg/ml; Sigma Chemical) in sodium acetate pH 5.0 containing 0.85% NaCl for one hour at 37° C. Sections were then incubated overnight with 2.5 μg/ml anti-TG-β isoform antibodies, incubated with biotinylated goat anti-rabbit secondary antibody (Vectastain kit, Vector Laboratories), and staining was continued as described above.

Ki67 Immunoreactivity:

In the porcine model, the following protocol was used: actively proliferating cells in the epidermis and neodermis were immunostained for Ki67 antigen. The tissue slides were subjected to antigen retrieval. Endogenous peroxidase activity was neutralized with 6% $H_2O_2$ for 20 minutes followed by blocking non-specific reactivity with a casein-based protein block (DAKO, Carpintera, Calif.) for 10 minutes. The slides were incubated with rabbit anti-human Ki-67 (NovaCastra Laboratories Ltd., Newcastle, UK) diluted at 1:1400 for 60 minutes in TBS. The rabbit Envision HRP System (DAKO) was used with DAB as substrate and the slides were counterstained with hematoxylin.

In the murine model, the following protocol was used: Slides were incubated at 55° C. overnight and deparaffinized in zylene and graded ethanols. The pressure cooker method (1 min at maximum pressure/temperature) in 10 mM citrate buffer with Tween-20 (Sigma-Aldrich) was used for antigen retrieval. Primary antibody was rabbit-anti-mouse Ki-67 1:250 (Novus). Secondary antibodies were peroxidase labeled and detected using avidin biotin complex followed by DAB substrate, all provided in a Rabbit Vectastain kit (Vector Laboratories). Sections were counterstained with hematoxylin (DAKO). Alternatively, mice were injected i.p. with bromodeoxyuridine (BrDU) 4 hours prior to harvesting the wounds and BrDU was thus incorporated into DNA as a marker of proliferation. The tissues were fixed in 10% formalin, embedded in paraffin, and tissues slices placed on slides for immunohistochemistry using antibodies to BrDU to detect proliferating cells.

Macrophage Detection:

Macrophage infiltration into the porcine wounds was assessed by immunostaining using a specific antisera for tissue monocytes/macrophages (MAC387AbD; Serotec, Raleigh, N.C.). The tissue sections underwent antigen retrieval by boiling the slides in 0.01 M Tris/HCL pH 10. Both quenching peroxidase activity and blocking non-specific immunoreactivity were performed as described above. A monoclonal mouse anti-human antibody to a macrophage epitope (MAC387) was used at 1:1000 for one hour. The mouse Envision system HRP kit (DAKO) was used for detection as described above.

H&E and Trichrome:

H&E and Trichrome stains of the murine and porcine wounds were performed by the department of pathology at NYU. Trichrome staining was used to visualize collagen content staining as cyano blue fibrils and cell nuclei stain red.

Picrosirius Red:

To evaluate the amount and quality of collagen deposition into the murine and porcine wounds, sections were treated with picrosirius red. Briefly, sections were deparaffinized and then incubated in 0.1% picrosirius red for 1 hour. Sections were then washed in PBS and dehydrated. Images were viewed under polarized light and qualitatively analyzed for collagen maturation. Yellow-green staining suggested better organization and less cross-linking of collagen fibrils. Red-yellow staining suggested higher levels of collagen cross-linking, and has been implicated in potential scarring.

In vitro Effects of Calreticulin

Cell cultures:

Keratinocytes: Primary Adult Human Epidermal Keratinocytes (#CC-2501;

Cambrex-Lonza, Inc., Walkersville, Md.) were cultured in Keratinocyte Growth Media (KGM) containing additives from the BulletKit [Singlequots] (Cat #CC-4131; Cambrex-Lonza, Walkersville, Md.), including Gentamycin-1000 (Lonza). The cells were subcultured at 50% confluency by washing with 30 mM HEPES buffered saline, treating with trypsin-EDTA (0.025% trypsin—0.02% EDTA; Lonza) and neutralizing the trypsin with neutralizing solution (TNS; Lonza). Following slow centrifugation, the cells were resuspended in fresh media and seeded at different cell densities depending on the experiments described below.

Fibroblasts: Primary human low passage foreskin fibroblasts (CCD 1070SK; ATCC, Manassas, Va.) were grown in complete Eagles Minimal Essential Media (MEM, Gibco/Invitrogen, Carlsbad, Calif.) containing 10% fetal bovine serum (FBS; HyClone, Logan, Utah), 2 mM Glutamine (Mediatech, Manassas, Va.), and antibiotic-antimycotic (ABAM; Mediatech). At 60-70% confluency, the cells were washed with PBS, removed for re-plating with 0.25% trypsin-2.21 mM EDTA (Mediatech), the trypsin neutralized with 10% FBS in MEM, and the cells centrifuged and resuspended in complete MEM at the cell densities described in the assays below.

HMVECs: Human dermal microvascular endothelial cells (HMVECs; Cambrex-Lonza) were cultured in complete Endothelial Cell Medium (EGM; Lonza) supplemented with the EGM-MV BulletKit (CC-3125; Lonza). The cells were subcultured when approximately 70% confluent by washing with HEPES Buffered Saline solution, treating with 0.025% trypsin-0.01% EDTA, followed by neutralization with TNS, and the cells were centrifuged and resuspended in complete media.

Monocytes and macrophages: The human monocyte cell line, THP-1 (ATCC-#TIB-202, Manassas, Va.), was cultured in suspension in RPMI 1640 media (GIBCO/Invitrogen, Carlsbad, Calif.) supplemented with 10% FBS, 1% L-Glutamine, 1% Penicillin-Streptomycin. The cells were grown by removing media from the cells and replenishing with fresh media every 3-4 days. The THP-1 monocytes at a concentration of $5\times10^5$/ml in 10 ml of complete media were differentiated into macrophages by the addition of phorbol myristyl acetate (PMA) at 10 ng/ml for 48 hours.

Human mesenchymal stem cells: were derived from bone marrow and maintained in culture in alpha minimal essential media containing 20% fetal bovine serum exactly as described by Sekitya, I. et. al., (2002) Stem Cells. 20:530-541. The cells were only grown to 50% confluency prior to harvesting for experimental use to avoid differentiation.

Murine diabetic and normal fibroblasts, human primary fibroblasts isolated from Human Skin: Dorsal skin from diabetic mice (lep-/lep-), genetically identical to those used in the in vivo studies, was harvested, and fibroblasts isolated. Fibroblasts from human skin were isolated as follows: macerated foreskin tissue samples were pressed through a cell dissociation sieve from a tissue grinder kit and washed with PBS. For mouse skin, dorsal depiliated skin from the dorsum was chopped finely with scissors in MEM media and pressed through a cell dissociation sieve from a tissue grinder kit and washed in PBS. The cell suspension was then incubated with 1.0 ml of Liberase 3 (Roche) in DMEM media for one hour at 37° C. Following incubation, the suspension was passed through a disposable strainer (100 μm nylon; Falcon), and then applied to CD-31 labeled magnetic beads (Dynatech), to remove contaminating endothelial cells. The remaining cell suspension was plated onto 0.5% bovine gelatin (Sigma)-coated plates in Dulbeccos Modified Eagles Media (DMEM; Gibco) containing 10% fetal bovine serum (FBS; Gibco) and 1% Penstrep antibiotics (Mediatech). Cultures of primary human fibroblasts were grown in high (4.5 g/L glucose[Hi]) and normal (1.0 g/L [Normo]) levels of glucose media to stimulate both the normal and diabetic microenvironments [Lerman, O. Z. et al. (2003) Am. J. Pathol.; 162:303-312; Deveci, M. et al.; (2005) British J. of Dermatology; 152:217-224; Loots, M. A. M., et al. (1999) Archives of Dermatological Research; V291:93-99]. The cells were tyrpsinized for use as described above for the normal human fibroblasts.

Cellular Proliferation:

Calreticulins used in the various experiments described herein were rabbit Michalak 5-CRT+/− tag, human Michalak 5-CRT+/− tag and Michalak 23-CRT +/− tag, human GenWay CRT, and NAT-CRT. The CRT source used in each experiment is identified below in the Examples.

Keratinocytes: The primary human keratinocytes were seeded in 96-well tissue culture plates at a density of $2.0\times10^3$ in Keratinocyte Growth Media (KGM) and incubated for 48 hours or until the cells reached 50-60% confluency. The cells were washed with Keratinocyte Basal Media (KBM, Lonza) and treated with increasing concentrations of calreticulin (0-200 pg/ml) in KBM in triplicate. In certain experiments, keratinocytes were synchronized by growing in KBM for 24 hours prior to treating. Human EGF (10 ng/ml; Invitrogen, Carlsbad, Calif.) was used as a positive control and KBM served as a negative control. After 72 hours, metabolic activity as a reflection of cell growth was determined using the CellTiter 96® AQueous One Solution Cell Proliferation Assay (#G3580, Promega, Madison, Wis.). The absorbance of the soluble formazan chromophore was quantitated after 2 hours using a microplate reader (BioRad 680) at a wavelength of 490 nm.

Fibroblasts: The primary human dermal fibroblasts in complete MEM were seeded in 96-well tissue culture plate at a cell density of $2.0\times10^3$ cells per well. At between 50-60% confluency (approximately 48 hours), the cells were switched to serum-free MEM for 24 hours, treated with increasing concentrations of rabbit or human calreticulin (0-200 ng/ml) in triplicate for 72 hours, and cellular proliferation assessed by the MTS assay. Human FGF (5.0 ng/ml; R & D Systems, Minneapolis, Minn.) and serum-free media were positive and negative controls, respectively.

HMVECs: Primary human microvascular endothelial cells (HMVECs) were seeded in 96-well plates at a cell density of $2\times10^3$/well in complete EGM. Upon reaching approximately 60% confluency, the cells were switched to basal EGF containing 0.5% serum overnight and then, increasing concentrations of calreticulin (0-50 pg/ml) were added, and cellular proliferation assessed by the MTS assay after 24 hours. VEGF (10 ng/ml; Genway Biotech, San Diego, Calif.), and basal EGM were positive and negative controls, respectively. The concentrations of calreticulin described for each of the three cell types were predetermined by initially using a wider range of doses.

In Vitro Wound Healing Scratch Plate Assay:

The primary human keratinocytes, dermal fibroblasts, and human mesenchymal stem cells were seeded in 24-well tissue culture plates at $2.0\times10^4$/well for the keratinoctes and at,$1.0\times10^4$/well, for the fibroblasts and stem cells, in their respective complete media and the cells grown to approximately 70-80% confluency for the keratinocytes and fibroblasts and 50% confluency for the stem cells. The keratinocytes were washed with KBM and incubated in ketatinocyte basal media (KBM) for 18 hours prior to wounding. Wounds were created in each well by drawing a line down the center of the well with a 200 μl plastic pipette and the plate washed with KBM or serum-free MEM to remove the displaced cells. To denote the edges of the original wound, a dot was marked with a black pen on the underside of the plate. Following washing with media, increasing concentrations of calreticulin in KBM or MEM were added to keratinocytes (0-100 pg/ml) and to fibroblasts (0-10 ng/ml), respectively, and 0.1 to 50 ng/ml added to the stems cells, in duplicate wells. As positive controls, human EGF (10 ng/ml) and 5% FBS were added to the keratinocytes and fibroblasts, respectively, and 0.1 and 2% FBS were added to the stem cells. Negative controls were KBM for keratinocytes and MEM for fibroblasts and stem cells. After 48 incubation for the keratinocytes and 24 hours incubation for the fibroblasts and stem cells, the cells were washed and stained with 0.025% Coomassie blue in 10% acetic acid:45% methanol for 10 minutes and washed twice with PBS or water. The wells were viewed with an inverted light microscope (Axiovert S-100; Zeiss, Thornwood, N.Y.) and images captured using Metamorph® software (Molecular Probes, Eugene, Oreg.). Wound closure (cellular migration) was determined using NIH Image J version 1.37 software, by outlining the front of cell migration into the wounds, calculating the area of the scratch remaining unoccupied by the cells and comparing this area to area in the original scratch at time zero. Alternatively, percent wound closure (migration) of the wound was determined by counting the number of cells in 16 rectangles of set dimensions that had migrated over the line of the original wound at time zero, using Image J software.

Thin Membrane Chamber Cellular Migration Assays:

A thin membrane ChemoTx® system (Neuroprobe Inc, Gaithersburg, Md.) in a 96-well plate format and two different cell-labeling methods were used to determine whether calreticulin mediates directed migration of the keratinocytes, fibroblasts, monocytes, and macrophages. The assay was performed according to the manufacturer's instructions. Fibroblasts and adherent macrophages were washed with PBS and removed from the plate with 0.25% trypsin/2.21 mM EDTA in Hanks Balanced Salt Solution (HBSS; Cellgro, Herndon, Va.), the trypsin activity neutralized with serum-containing media, and the cells centrifuged at 235×g for 5 minutes. Keratinocytes were washed with HEPES-BSS (Lonza, Walkersville, Md.) and trypsinized, suspended in TNS, and centrifuged as described above. All cell pellets were suspended in their respective serum-free media. The migration wells in the bottom chamber were loaded with 330 μm of increasing dilutions of calreticulin in serum-free media for keratinocytes, fibroblasts, monocytes, and macrophages. Treatments were performed in triplicate. Serum-free media was used as a negative control and EGF (10 ng/ml; keratinocytes), FGF (5.0 ng/ml; fibroblasts) the phlogistic agent N-formyl-Met-Leu-Phe (fMLP 1-100 nM, monocytes; Sigma Chemical Co, St Louis, Mo.), and VEGF (100 ng/ml; Fisher Scientific) or fMLP (100 nM macrophages) were used as positive controls, as shown in individual experiments. The frame of the apparatus containing the membrane was carefully placed on top of the wells, 50 μl of cell suspension was loaded onto the membrane above each well bordered by a rubber gasket, the lid replaced, and the cells incubated at 37° C., 5% CO2. The number of cells per well, pore size of the polycarbonate Neuroprobe membrane, and migration time period varied for each cell type as follows: keratinocytes at $2.5\times10^4$/well, 8 μm pore size, 4 hours; fibroblasts at $5.0\times10^4$/well, 8.0 μm, 4 hours; THP-1 monocytes at $5\times10^4$/well, 5 μm pore size, one hour; THP-1 macrophages at $2.5\times10^4$/well, 5.0 μm pore size, 2 hours. Following the respective incubation periods, the chambers were dismantled, the membranes washed with PBS, the cells fixed with 4% paraformaldehyde for 5 minutes, and the membranes applied to a cover slips, which were sealed and stained using Vectashield® and DAPI (Vector Labs, Burlingame, Calif.). Each membrane was photographed at 200× magnification in at least 6 fields and an average of three high power fields (hpf) calculated for the number of cells per well using Kodak ID software. In certain experiments, the THP-1 monocytes and PMA-induced differentiated adherent macrophages were labeled with 2-4 μM Calcein AM (Molecular Probes, Eugene, Oreg.) prior to applying the cells to the membrane. The concentration of the fluorochrome and incubation times varied for each cell type as follows: macrophages, 4 μM Calcein for 30 minutes and monocytes, 2 μM Calcein for 40 minutes. Following the incubation times, the remaining cell suspension was aspirated, the membrane carefully wiped with a cotton swap dipped in PBS, treated with 201 μM EDTA in PBS for 20 minutes at 4° C., and the plate centrifuged at 1,500 RPM (Beckman Model J-6M, Fullerton, Calif.) for 10 minutes at 4° C. to detach the cells in the membrane into the lower chamber. The membrane was removed and fluorescence reflecting the number of cells that migrated in and through the membrane into to the bottom chamber was determined in a fluorimeter, Victor3 V™ Multilabel Counter (Perkin Elmer, Waltham, Mass.) using excitation and emission wavelengths of 485 nm and 535 nm, respectively. The calreticulin sources used for individual experiments and compared for biological activity are described in each experiment and identified in the Examples below.

Western Blot Analysis:

Keratinocytes and fibroblasts were treated separately with increasing concentrations of calreticulin for 24 to 48 hours and cell lysates prepared with RIPA lysis buffer. Protein concentrations of cellular supernatants were determined by the DC Protein Assay kit (Bio-Rad Laboratories) and equal concentrations of protein (5-40 μgs) in Laemmli were applied to SDS-PAGE gradient gel (5-20% acrylamide) for separation by molecular weight by electrophoresis. The proteins were transferred to Hybond polyvinylidene difluoride (PVDF) membranes. The procedures for immunoblotting were according to the individual antibodies used as directed by each manufacturer. The blots were exposed to BioMax X-ray film for protein detection and densitometry performed for quantitation of the protein bands using an EDAS 290 scanner and Kodak 1D image analysis software. By densitometric scanning, the amount of protein in each well was normalized to an actin control.

Statistical Analyses:

For the morphometric analyses of the wounds in the porcine model, the values obtained were subjected to the Kruskall-Wallis Test for non-parametric samples. A Mann-Witney U-test was used for comparison between individual samples. Statistical analyses for all experiments were performed using SPSS® version 12 software (Chicago, Ill.).

Immunohistochemical staining was analyzed both qualitatively and quantitatively for Ki-67 and macrophages, with quantitative data expressed as cells per high powered field (hpf=200×).

An unpaired Student's t-test was used to analyze the data of the murine wounds. Statistical significance was considered at $p<0.05$. Statistical analyses were performed using SigmaStat Statistical Software Version 2.03 (Aspire Software International, Leesburg, Va.).

Example 1: Calreticulin Enhances Porcine Wound Healing in Normal Pigs and a Porcine Diabetic Model Wound Re-Epithelialization An accelerated rate of re-epithelialization of wounds is one of the indicators of enhanced wound repair. After 5 days of healing, epithelial islands derived from keratinocytes migrating upward from hair follicles and sweat glands, and epithelial wound edges in calreticulin-treated wounds, displayed a higher degree of resurfacing and epidermal stratification compared to either the wounds treated with buffer or Regranex®, PDGF-BB. Regranex® (PDGF-BB), the first and only FDA approved cytokine treatment for cutaneous wound repair, was used as a positive control in the porcine wound healing experiments. See, Clark et al., J Invest Dermatol. 2007; 127:1018-1029; Embil et al., Wound Repair Regen. 2000; 8:162-168; Meier K, Nanney L B, Expert Opin Emerg Drugs 2006; 11:23-37.

Figure 1:
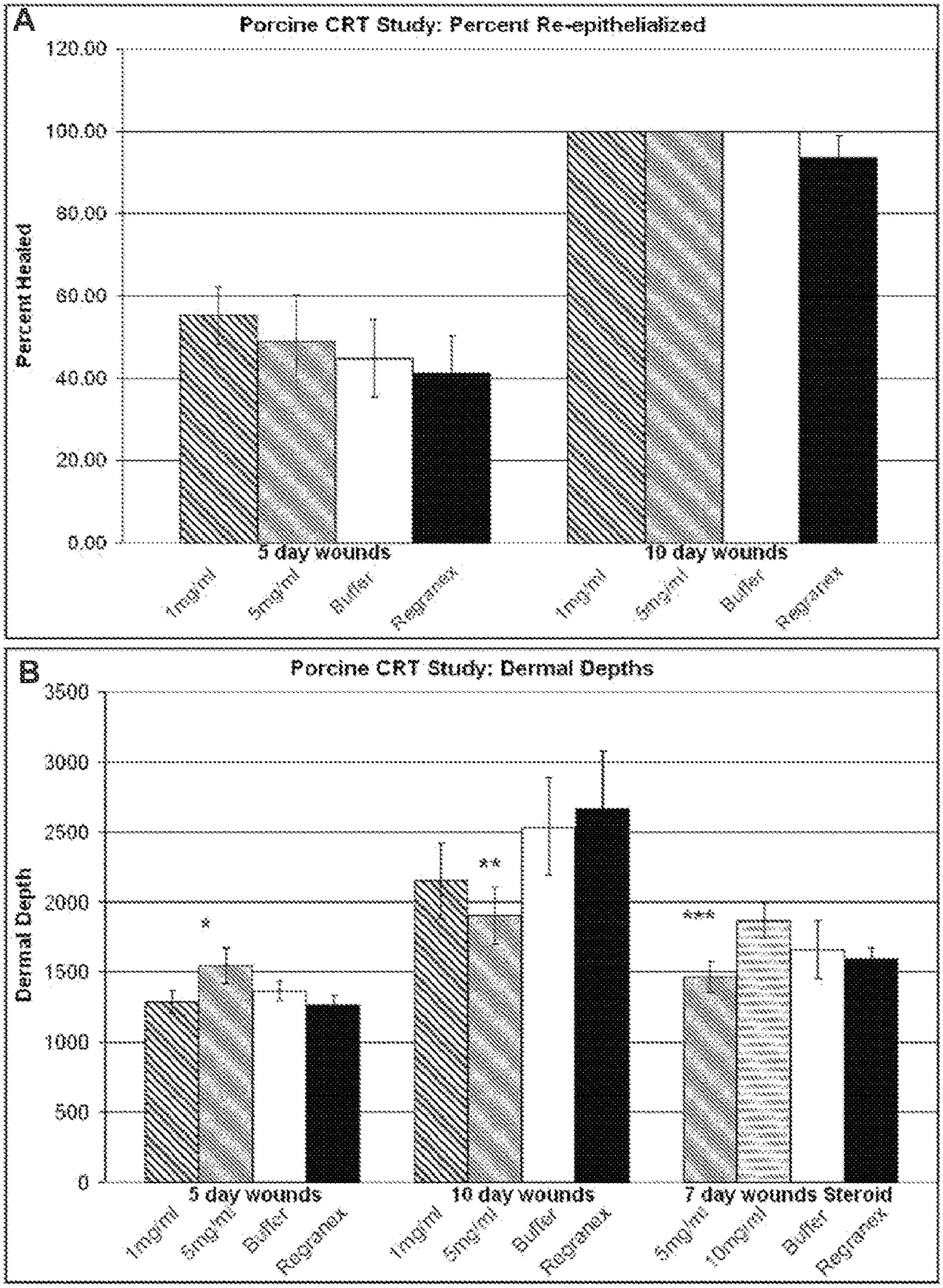
FIG. 1A is a graph of quantitative morphometric analysis of percent re-epithelialization (percent healed) of calreticulin-treated (topical) porcine partial thickness wounds at 5 and 10 days after injury.
FIG. 1B is a graph of quantitative morphometric analysis of dermal depths of the wound after calreticulin-treated (topical) porcine wounds at 5 and 10 days after injury and at 7 days after injury in pigs that have been treated with methylprednisolone to induce impaired wound healing as in a diabetic wound.

FIG. 1 shows graphs of quantitative morphometric analysis of calreticulin-treated (mixture of rabbit 5-CRT+ tag and 23-CRT+ tag) porcine wounds at 5 and 10 days after injury. As shown in FIG. 1A, re-epithelialization, expressed as percent healed, of wounds in normal pigs after 5 days and 10 days of healing was analyzed. The exogenously applied treatments were: 1.0 mg/ml or 5.0 mg/ml calreticulin, buffer or PDGF-BB. After 5 days post-wounding, calreticulin induced a trend toward enhancing re-epithelialization (resurfacing) of the wounds ($p=0.05$ 8; n=6 wounds per parameter). The percent of epithelial resurfacing (percent re-epithelialized) with 1.0 mg/ml calreticulin (200 μg/wound) was 58% compared to 41% and 44% for the PDGF-BB-treated and buffer-treated wounds, respectively, at 5 days after injury (FIG. 1A). By 10 days after wounding, only the PDGF-BB-treated wounds were not 100% re-epithelialized. The percent healed is presented as the mean±SEM. In contrast, at 10 days after wounding, the calreticulin-treated and control wounds were 100% re-epithelilialized. Both the increase in re-epithelialization and epithelial stratification of the calreticulin-reated wounds at 5 days and the higher degree of stratification and cornification at 10 days suggest that calreticulin increased the rate of epidermal maturity. Cells were stained red and collagen was stained cyano-blue; e=epidermis, nd=neodermis. Scale bars for panels A-C=850 μm; D-I=88 μm. Quantitative analysis of epithelial resurfacing, based on six wounds per treatment group, revealed a trend but fell short of reaching statistical significance ($p \leq 0.058$). From the histological observations and the trend from the quantitative data set, it appears that statistical significance might have been achieved with a larger number of wounds per group that was not feasible in this study due to lack of sufficient supply of calreticulin for the large animal wounds.

Granulation Tissue Formation/Neodermal Depth

Restoration of dermal tissue is a dynamic process essential for remodeling the wound bed. The accrual of neodermal connective tissue is largely mediated by fibroblasts recruited into the wound, the continued migration, proliferation, and production of extracellular matrix proteins by these cells, capillary ingrowth, and an influx of inflammatory cells and progenitor cells from outside the confines of the wound. See, Gailit J, Clark R A, Curr Opin Cell Biol. 1994; 6:717-725; Singer A J, Clark R A, N Engl J Med. 1999; 341:738-746. The extent of matrix formation is a composite assessment reflecting the quality of the dermal response. Early in the reparative process, before the epidermis heals across the wound surface, the wound bed is filled with a loose granulation tissue sparsely populated with cells, which progressively forms a mature, comparatively dense, irregular connective tissue containing increasing amounts of collagen.

In FIG. 1B, granulation tissue/neodermal depths measurements of treated (as in A) wounds in normal and steroid-impaired pigs were analyzed after 5 and 10 days of healing. As shown in FIG. 1B, calreticulin induced a dose-dependent increase in dermal thickness (*$p \leq 0.058$; n=4). At 10 days of healing, the dermal depths of the 5.0 mg/ml calreticulin-treated wounds were significantly smaller than the buffer ($p \leq 0.05$; n=6) and PDGF-BB-Regranex® ($p \leq 0.04$; n=6)-treated wounds ($p \leq 0.04$; n=6), reflecting the more advanced healing observed by the histologyical observation of the calreticulin-treated wounds (compare in FIG. 2, panels A,D with C,F). In the steroid-impaired wounds, a dose-dependent response was obtained with 5.0 mg/ml and 10 mg/ml calreticulin at 7 days post-wounding (*$p \leq 0.034$; n=6). The dermal depths are presented as the mean±SEM.

Figure 2:
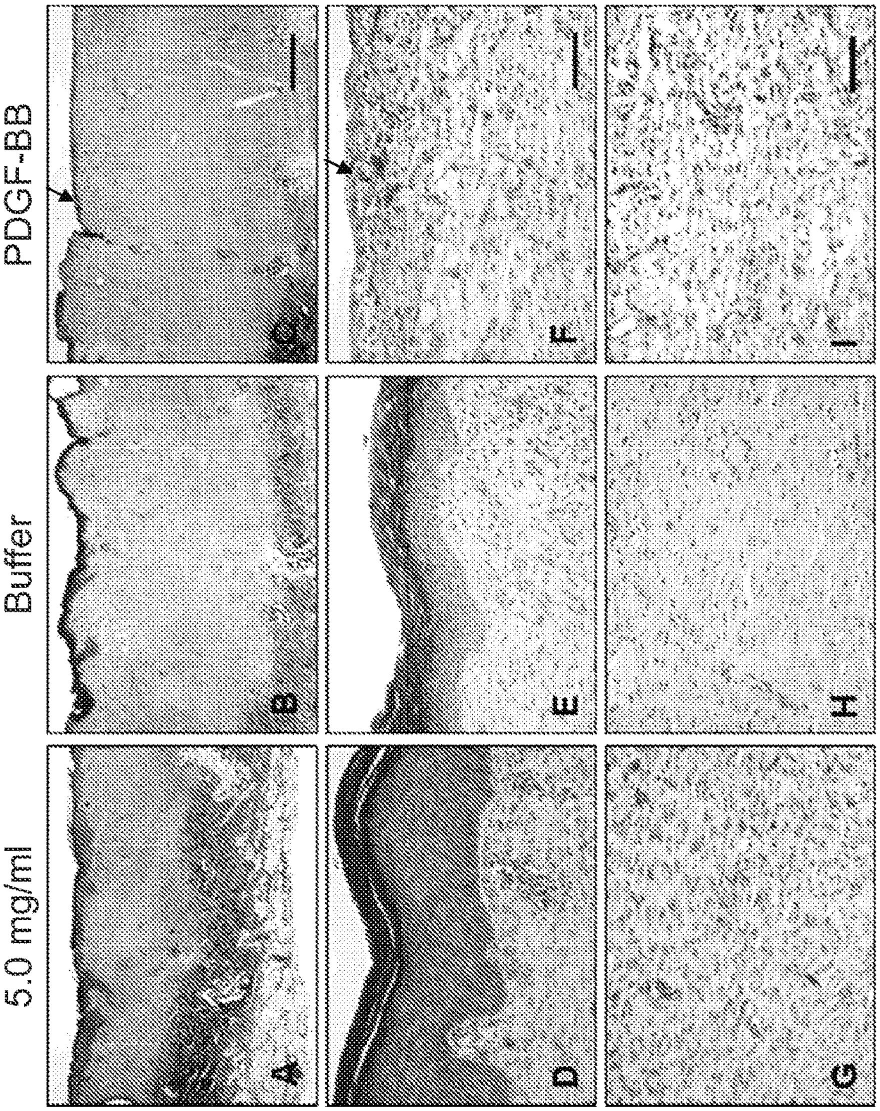
FIGS. 2A-2I represents micrographs of trichrome stained calreticulin-treated porcine wounds compared to Regranex and buffer-treated partial thickness wounds after 10 days of healing.

FIG. 2 shows photomicrographs of trichrome stained calreticulin-treated porcine wounds after 10 days of healing. Treatments were as follows: 5.0 mg/ml calreticulin (mixture of rabbit 5-CRT+ tag and 23-CRT+ tag) (FIG. 2A,D,G); buffer (FIG. 2B,E,H); PDGF-BB (Regranex®) (FIG. 2C,F, I). Treatment with calreticulin resulted in a more mature, stratified epidermis (FIG. 2A,D) as compared to buffer (FIGS. 2B,E) and PDGF-BB (FIGS. 2C,F) treated wounds, showing incomplete re-epithelialization (arrows).

In wounds examined 5 days after wounding, the neodermal depth (granulation tissue) was thicker in the 5 mg/ml compared to 1.0 mg/ml calreticulin-treated wounds (FIG. 1B; $p \leq 0.058$). The higher dose of calreticulin induced a statistically significant greater neodermal depth than PDGF-BB (FIG. 1B; *$p \leq 0.04$). By 10 days of healing, there was a dose-dependent compaction of neodermal depth in the 1.0 mg/ml and 5.0 mg/ml calreticulin-treated wounds, which was statistically significant compared with the buffer and PDGF-BB-treated wounds (FIG. 1B; $p \leq 0.05$ and $p \leq 0.04$, respectively). Similar to the greater degree of epidermal maturity, marked by epidermal stratification of the calreticulin-treated wounds (FIG. 2A,D) compared to the buffer (FIGS. 2B,E) and PDGF-BB-treated wounds (FIGS. 2**C,F), the decrease in dermal depth in the calreticulin-treated wounds represents a neodermis that is found later in the wound repair process. These more mature wounds show a characteristic notable uniform distribution of collagen fibers throughout the neodermis. The less mature PDGF-BB-treated wounds have equally dense collagen in the deepest regions of the dermis but less collagen density near the top of the wound bed where the epidermis has not quite resurfaced the wound.

Steroid-treatment (methylprednisolone in these studies) of pigs is a well-established model for simulating diabetic impaired wound healing. This model is useful for detecting effects in the dermis and thus, is applicable to events that frequently impair human healing. See, Leibovich S J, Ross R, Am J Pathol. 1975; 78:71-100. In steroid-challenged pigs, the wounds were harvested after 7 days of healing. Upon histological examination, re-epithelialization of the wounds was 100% complete, thereby obviating the ability to determine the effect of the treatments on rate of wound resurfacing. However, measurement of neodermal depths show that the 5.0 mg/ml calreticulin and PDGF-BB-treated wounds were nearly equal (FIG. 1B) and a dose-dependent effect in dermal depth was achieved with 5.0 mg/ml and 10.0 mg/ml calreticulin (FIG. 1B; ***$p \leq 0.034$). Although calreticulin at 10 mg/ml induced a greater dermal depth than the buffer and PDGF-BB controls, this apparent trend representing a small number of wounds, was not statistically significant.

Example 2: Calreticulin Increases Wound Tensile Strength

Figure 3:
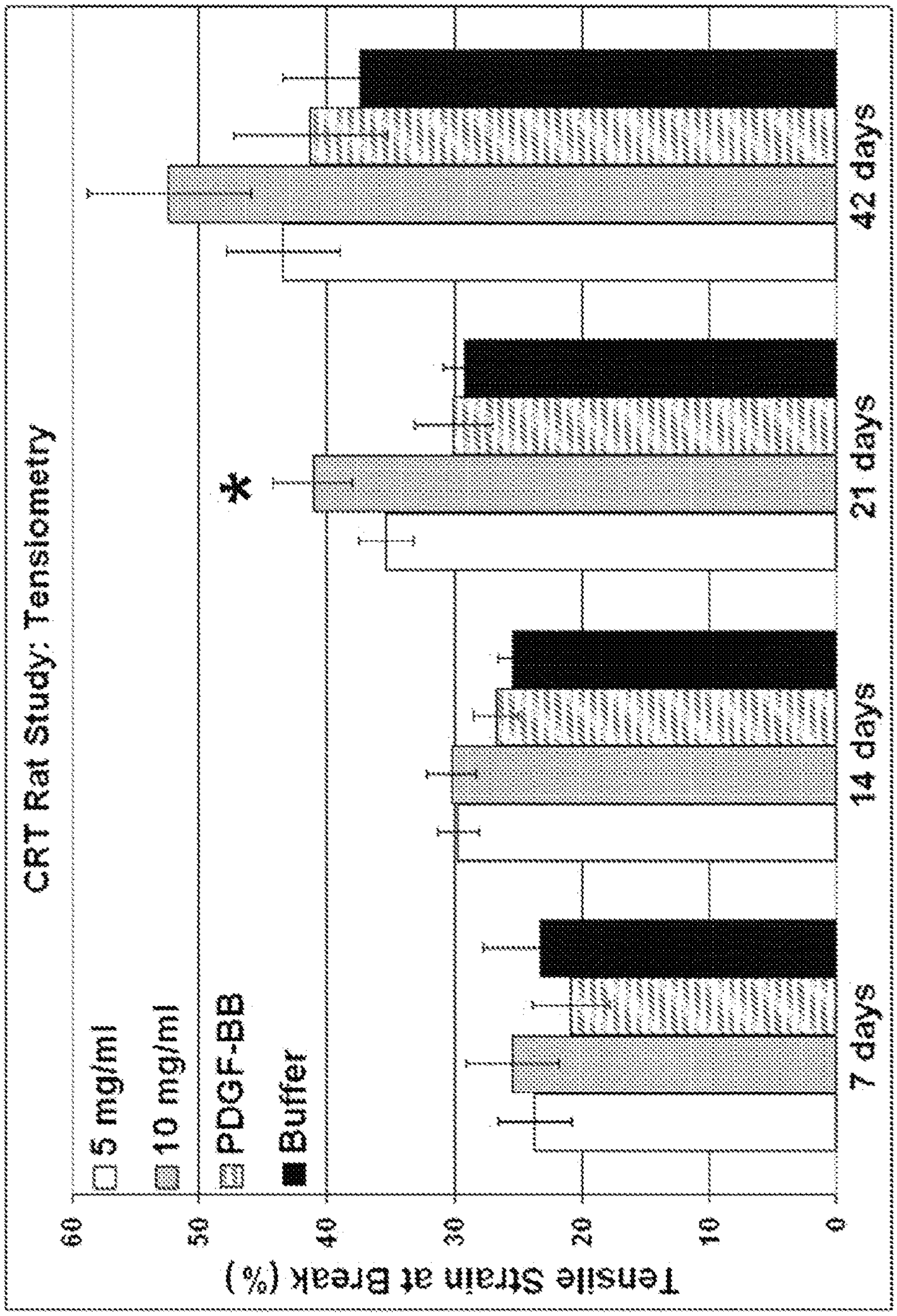
FIG. 3 is a graph showing the effect of calreticulin on wound tensile strength (breaking strength) in a rat incisional model at 7, 14, 21, and 42 days after wounding.

The quantitative (FIG. 1) and qualitative effects of calreticulin on the granulation tissue/neodermis suggested that the calreticulin-treated wounds might have greater integrity of wound strength compared to the buffer and PDGF-BB-treated wounds. Thus, the impact of calreticulin on the wound tensile strength was analyzed using a well-established rat incisional model for wound breaking tensile strength. See, Ballas C B, Davidson J M, Wound Repair Regen. 2001; 9:223-237. In this assay, four incisional wounds were created on each rat, which were approximated with clips, and four different treatments were applied: 5.0 mg/ml, 10 mg/ml calreticulin (mixture of rabbit 5-CRT+ tag and 23-CRT+ tag), buffer, and PDGF-BB; n=10 rats/treatment/time point. After the 7, 14, 21, and 42 days, wound breaking strength was measured with a tensiometer. Calreticulin at 5.0 mg/ml after 21 days induced a statistically significant increase in the breaking strength of the wounds compared to the buffer or the PDGF-BB-treated wounds (FIG. 3; $p \leq 0.019$). The specificity of this biological response was substantiated by an even greater breaking strength of wounds treated with 10 mg/ml calreticulin compared to both the buffer (*$p \leq 0.001$) and PDGF-BB-treated wounds ($p \leq 0.027$). Wounds harvested at 7, 14, or 42 days of healing did not show statistically significant differences in breaking strength among the various treatment groups (FIG. 3**).

Example 3: Calreticulin is Dynamically Expressed During Wound Repair

Figure 4:
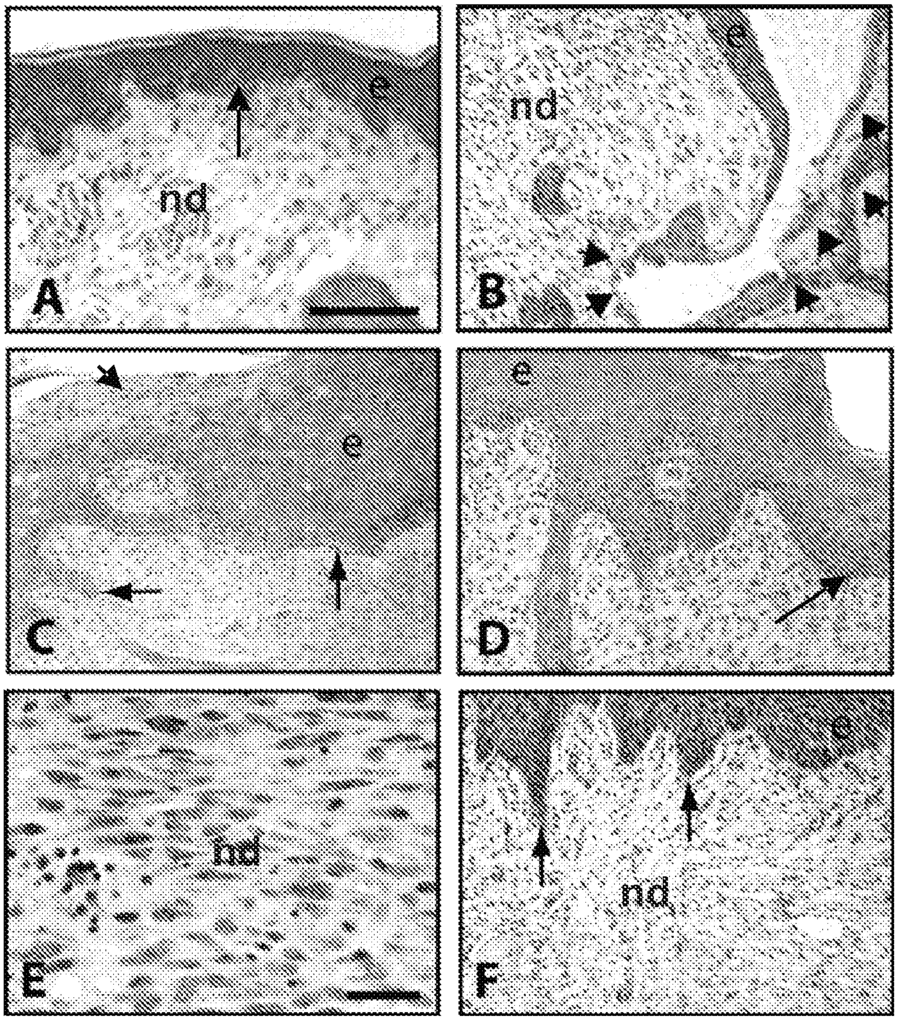
FIGS. 4A-4F shows immunostaining for endogenous calreticulin in buffer-treated and Regranex-treated porcine wounds evaluated at 5 and 10 days after injury of normal (4A-4E) and steroid-impaired pigs (4F).

A dynamic expression of calreticulin during wound repair would suggest a physiological role for this protein in tissue repair. Moreover, the fact that exogenously applied calreticulin exerted apparent effects on both the epidermal and dermal components of the porcine partial thickness wounds supports this hypothesis. To test the hypothesis, the spatial and temporal distribution of endogenous calreticulin in the wound repair models 5 and 10 days after injury were evaluated by immunohistochemistry (IHC) in Regranex® gel-treated (PDGF-BB) (FIG. 4 D,E) or buffer-treated wounds (FIG. 4 A-C, F). In unwounded (adjacent) skin (FIG. 4A), basal and suprabasal keratinocyte layers of normal skin showed slight to no immunoreactivity in contrast to the more differentiated stratum corneum, granulosum, and spinosum upper layers of epidermis, which demonstrated intense immunoreactivity. At 5 days following wounding (FIG. 4B), in the buffer-treated control wounds, there was a notable absence of calreticulin in the migrating keratinocytes both, emanating from the wound margins and those migrating upward from the hair follicles and sweat ducts; these are the keratinocytes responsible for the formation of the epithelial islands within a partial thickness skin injury. In areas of mature stratified epidermis, calreticulin immunoreactivity was moderate, and still less than in unwounded epidermis. In the granulation tissue, there was a marked increase in the number of cells showing strong immunoreactivity for calreticulin. Morphologically, these cells appeared to be mainly fibroblasts and other connective tissue cells including immune cells. At 10 days post-wounding (FIG. 4C-E) in both Regranex® (PDGF-BB)-treated (FIGS. 4 D,E) and buffer-treated (FIG. 4 C) wounds, the keratinocytes composing the hypertrophic epidermis, particularly in the more differentiated stratum spinosum layer, still expressed ample amounts of calreticulin, whereas the expression of calreticulin by the cells of the neo-dermis has greatly waned. As shown in FIG. 4C at 10 days post-wounding, the migrating epithelium is devoid of calreticulin (top arrow). In the steroid-impaired animals (FIG. 4F), at 7 days post-wounding, the wounds appeared similar to the unimpaired wounds with respect to the distribution of calreticulin immunoreactivity in the epidermis. The intensity and number of cells expressing calreticulin in the neodermis appeared to be at intermediate levels between the 10 day post-injury wounds of the normal untreated non-impaired pigs, which was low and the higher immunoreactivity observed in the PDGF-BB-treated wounds (FIG. 4D,E). Interestingly, cells of the dermis of the Regranex-treated wounds (FIG. 4 D) expressed higher amounts of calreticulin than the buffer control wounds at both 5 days and 10 days after injury (FIG. 4B,C). The upregulation of calreticulin in the healing dermis of the PDGF-BB-treated wounds suggests that calreticulin is increased in wounds in which wound healing is stimulated. In FIG. 3, e=epidermis; nd=neodermis; arrows indicate basal epidermal cells with weak immunoreactivity for calreticulin; arrowheads indicate migrating epithelium; and brown represents DAB positive immunoreactivity. The scale bars in panels A-D, F=500 μm, and Panel E=30 μm.

Example 4: Topical Application of Calreticulin to Wounds Induces the Expression of TGF-β3

TGF-β isoforms are important regulators of many aspects of wound healing including induction of extracellular matrix proteins, such as collagens and fibronectin, and chemoattraction of cells into the wound. See, Ogawa et al., Growth Factors 1991, 5:57-68; Ksander et al., Ann N Y Acad Sci. 1990; 593:135-147; Kinbara et al., J Cell Physiol. 2002; 190:375-381; Roberts A B, Sporn M B: Transforming Growth Factor-beta. Edited by Clark R A F. New York, Plenum Press, 1996, 275-308. Moreover, TGF-β isoforms are differentially upregulated, temporally and spatially, during wound repair including in a porcine model of repair indicating specific biological effects of the individual isoforms. See, Kinbara et al., J Cell Physiol 2002, 190:375-381; Levine et al., Am J Pathol. 1993; 143:368-380; McMullen et al., Wound Repair Regen. 1995; 3:141-156.

Figure 5:
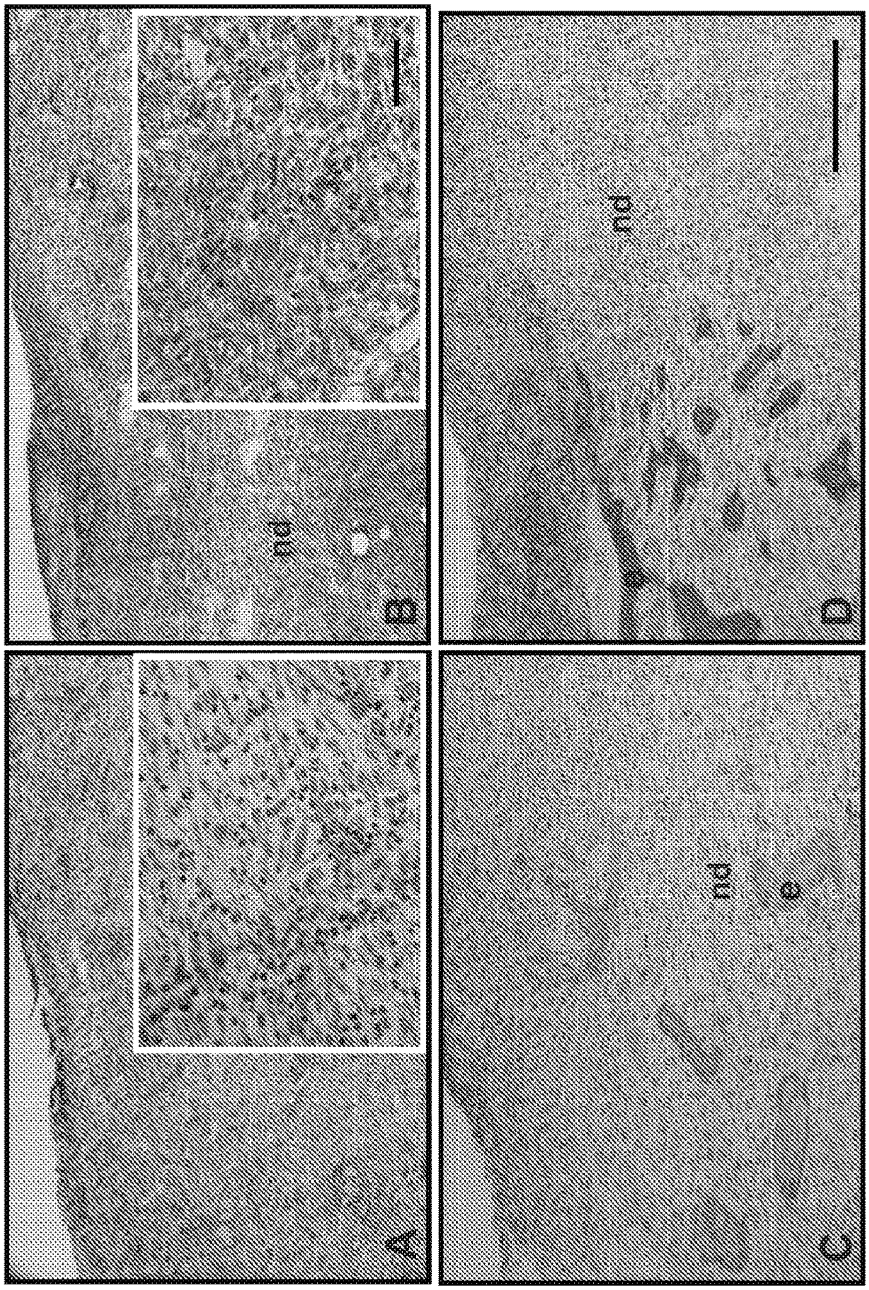
FIGS. 5A-5D represents immunostaining for TGF-β isoforms (β1, β2, β3) in calreticulin-treated normal porcine wounds.
Figure 6:
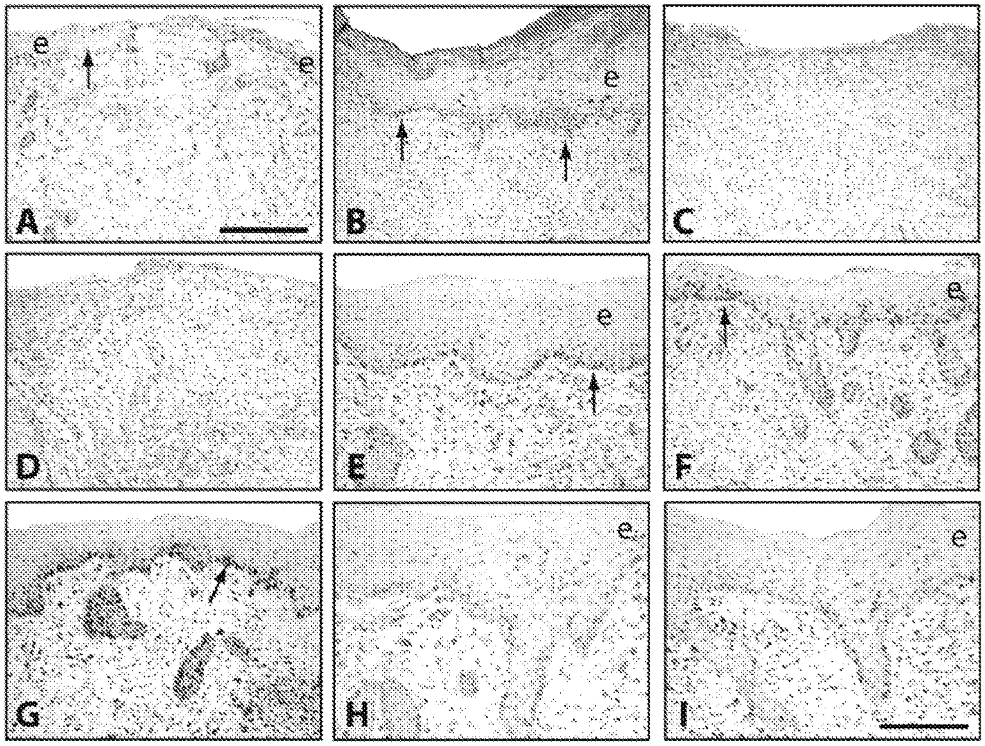
FIGS. 6A-6I shows immunostaining for proliferating cells (Ki67) in calreticulin-treated normal and steroid-impaired porcine wounds.
Figure 7:
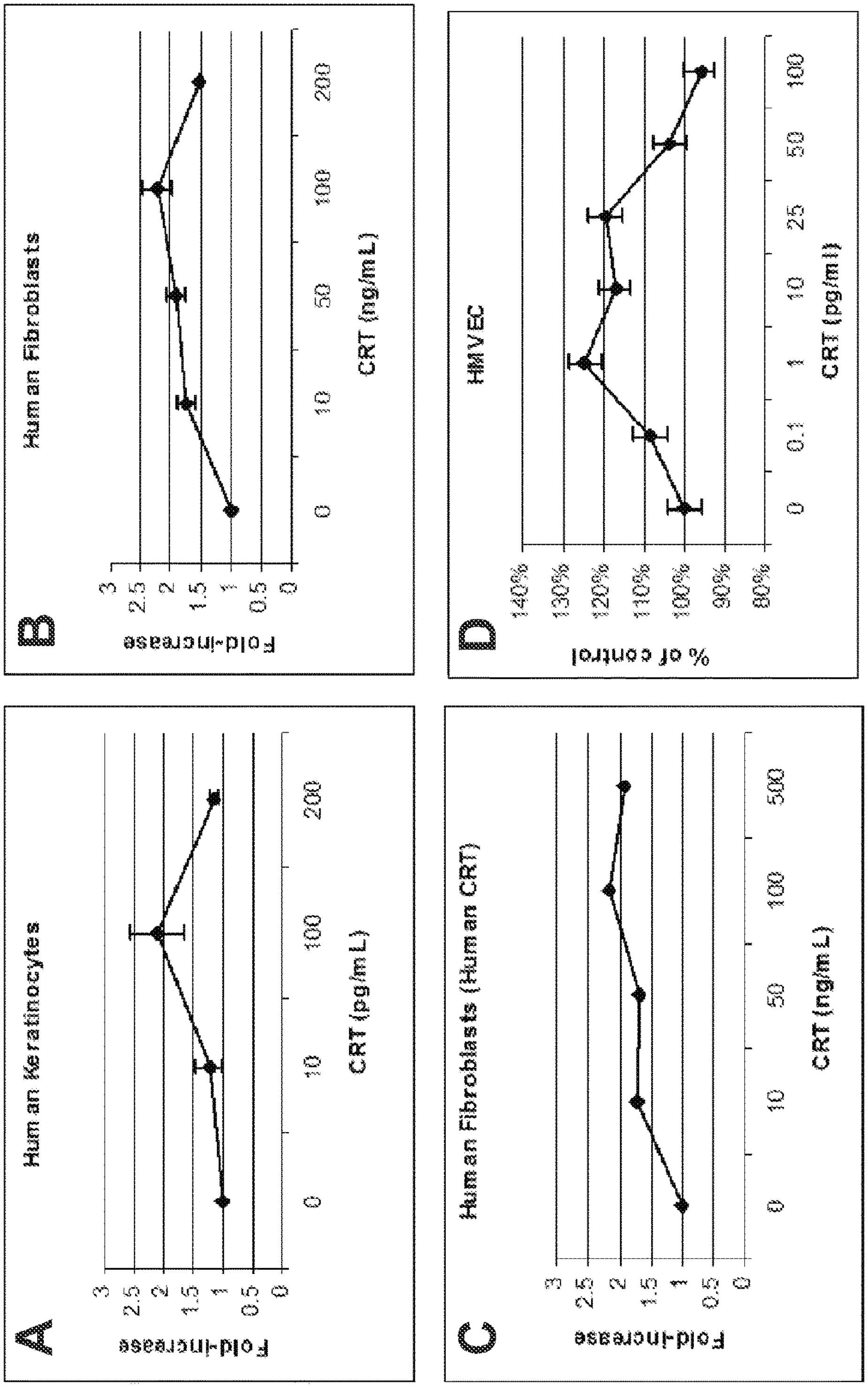
FIGS. 7A-7D shows that, in vitro, calreticulin induces cellular proliferation of primary human keratinocytes, fibroblasts, and microvascular endothelial cells.

In FIG. 5, immunostaining for TGF-β isoforms in calreticulin-treated (mixture of rabbit 5-CRT+ tag and 23-CRT+ tag) normal porcine wounds was performed. Immunoreactivity for TGF-β3 (FIG. 5A,B), TGF-β1 (FIG. 5C), and TGF-β2 (FIG. 5D) after five days of healing was determined. Buffer-treated wounds are shown in FIG. 5A and calreticulin-treated wounds are shown in FIG. 5B-D. Using this assay, a marked intensity of immunoreactivity for TGF-β3 was observed in the granulation tissue of the 5.0 mg/ml calreticulin-treated wounds at 5 days after injury (FIG. 5B) compared to the buffer-treated wounds (FIG. 5A); the magnified insets in FIGS. 5A and 5B show the intense cellular TGF-β3 immunostaining in the calreticulin-treated wounds. The newly forming epidermis was moderately immunostained for TGF-β3. In contrast, neither TGF-β1(FIG. 5C) nor TGF-β2 expression was induced by 5.0 mg/ml calreticulin in the neodermis. Whereas TGF-β2 immunoreactivity was shown in the newly forming epidermis (FIG. 5D), no further induction by calreticulin was observed. The scale bars in panels A-D=300 μm; insets=30 μm; and e=epidermis; nd=neodermis. In summary, consistent with the enhanced dermal repair in the calreticulin-treated wounds (Example 1), this experiment showed that the specific expression of the TGF-β3 isoform, but not TGF-β1 nor TGF-β2, is strongly increased in the dermal cells of the calreticulin-treated wounds compared to the buffer-treated wounds at 5 days post-wounding. PDGF-BB- and buffer-treated wounds showed equal intensity of immunostaining at this time point. Whereas a dose-dependent increase in TGF-β3 immunoreactivity was observed in wounds at 10 days post-wounding, the intensity of TGF-β3 immunoreactivity was diminished compared to the earlier 5-day post-injury wounds. The specific upregulation of the expression of the TGF-β3 isoform by calreticulin is significant in terms of the unique ability of TGF-β3 to mediate collagen gel matrix contraction (to stimulate wound contraction), motogenic behavior of cells, acceleration of wound healing with decreased scar formation, induction of hyaluronan, which is important in neodermal formation, and increasing the expression of collangenases MMP2 and MMP9 for wound extracellular matrix remodeling (O'Kane S (1997) Int J Biochem Cell Biol 29:63-78; Li W Y (2006) Wound Repair Regen. 14:516-525; Schor S L (2006) Cell Motil Cytoskeleton 63:287-300; Wu L (1997) Arch Surgery 132:753-760; Meier K (2006) Expert Opinion Emerg Drugs 11:39-47; Shah M (1995) J Cell Sci 108:985-1002; Ellis I R (1999) Cell Biol. 25:593-602; Wu M (2007) Matrix Biol 26:463-472). The TGF-β3 isoform is considered as the master regulator of migration of epidermal and dermal cells ("traffic control") during cutaneous repair (Bandyopadhyay B (2006) J Cell Biol 172:1093-1105.

Example 5: Topical Application of Calreticulin to Wounds Stimulates Cellular Proliferation of Basal Keratinocytes and Presumptive Fibroblasts of the Dermis Cellular proliferation of keratinocytes (to resurface the denuded wound) and fibroblasts (to increase the number of cells engaged in matrix production) is critical to the wound repair process. To assess the effect of calreticulin on the cellular proliferation in porcine wounds treated with calreticulin (mixture of rabbit 5-CRT+ tag and 23-CRT+ tag) in vivo, tissues from excised wounds were subjected to immunohistochemical staining using a standard proliferative cell marker, kinetochore nuclear protein 67 (Ki67). The groups were as follows: wounds from normal pigs at 5 days after healing (FIG. 6A-D); wounds from steroid-impaired pigs at 7 days after healing (FIG. 6E-I). Treatments were as follows: 1.0 mg/ml calreticulin (FIG. 6A); 5.0 mg/ml (FIG. 6B, E); 10 mg/ml calreticulin (FIG. 6F); 50 mg/ml calreticulin (FIG. 6G), buffer (FIGS. 6C,H), and Regranex® (PDGF-BB) (FIG. 6D,I). Calreticulin-treatment induced a dose-dependent increase in the number of proliferating basal and suprabasal keratinocytes (arrows indicate epidermal replenishment compartment) in the immature epidermis of the calreticulin-treated normal wounds (FIG. 6A,B) compared to the buffer (FIG. 6C) and PDGF-BB-treated (FIG. 6D) wounds, which showed no epidermal resurfacing. In the wounds of the steroid-challenged pigs, calreticulin 5.0 mg/ml (FIG. 6E), 10 mg/ml (FIG. 6F) and 50 mg/ml (FIG. 6G)], is shown to induce a dose-dependent increase in proliferating keratinocytes in the basal layers of the epidermis compared to buffer- (FIG. 6H) and PDGF-BB-treated (FIG. 6I) wounds, which show relatively fewer Ki67 positive nuclei in the hypertrophic epidermis. There were numerous proliferating cells (presumptive fibroblasts) in the neodermis of both the wounds of the calreticulin- and PDGF-BB-treated normal (FIGS. 6A,B,D) and steroid-impaired pigs (FIGS. 6E,F,G,I) compared to the buffer controls (FIGS. 6C, H). The dose-dependent response of the calreticulin-treated wounds was also evident in the neodermis of the normal wounds (FIGS. 6A,B). Arrows indicate Ki67 positive proliferating basal keratinocytes. The scale bars in panels A-D=445 μm; and in panels E-I, e=epidermis; the scale bars=225 μm.

After wounding, keratinocytes first migrate over the wound and do not show evidence of proliferation in the regenerative suprabasal and basal layers until resurfacing is complete. Wounds from normal pigs treated with calreticulin, at 5 days after injury demonstrated a dose-dependent response in epidermal resurfacing and a corresponding intense Ki67 immunoreactivity in basal and suprabasal keratinocytes. In contrast, there were markedly fewer immunoreactive basal keratinocytes in the buffer-treated and Regranex®-treated wounds that show variable and barely resurfaced wounds. Marked proliferation (i.e., Ki67 immunoreactivity) was observed in dermal cells of the calreticulin-treated and PDGF-BB-treated wounds. With higher magnification, these dermal cells appear to be largely fibroblasts. In the more mature wounds at 10 days post-wounding, proliferation in the neodermis subsided, being replaced by matrix production.

It is notable that the identical immunostaining pattern to the porcine wounds was observed in the calreticulin-treated murine wounds. The basal and suprabasal keratinocyte layers of the epidermis and numerous presumptive fibroblasts in the neodermis immunostained positively for Ki67 only in the calreticulin treated wounds (data not shown) indicating that these cells proliferated in response to topical application of calreticulin. Only minimal positive immunoreactivity was observed in the buffer-treated controls.

Furthermore, similar to the results obtained with the normal pigs, in the steroid-challenged pigs, calreticulin-treatment induced a strong dose-dependent effect on the proliferation of basal and suprabasal keratinocytes in the 7-day post-injury re-epithelialized wounds and in dermal cells (FIG. 6E-G). As these wounds had re-epithelialized, the buffer-treated and PDGF-BB-treated wounds showed equal numbers of proliferating cells in the basal layer of the epidermis, albeit notably less than the calreticulin-treated wounds. The intensity of immunoreactivity in the dermal cells was similar in the Regranex® (FIG. 6I) and 5 mg/ml calreticulin-treated (FIG. 6E) wounds. Therefore, topical application of calreticulin to porcine wounds has a marked effect on cellular proliferation of both the epidermal and dermal aspects of repair in both normal and steroid-impaired (diabetic model) wound healing. The specificity of calreticulin on cellular proliferation in the epidermis and dermis during wound healing is corroborated by the dose-response effect obtained and the in vitro studies described below.

Example 6: Calreticulin Stimulates Cellular Proliferation of Human Keratinocytes, Fibroblasts, and Microvascular Endothelial Cells In vivo, in the porcine and murine wound healing experiments, calreticulin stimulated a robust proliferative response in the basal keratinocytes and the dermal fibroblasts as shown by a high level of Ki-67 immunostaining (FIGS. 6A, B, E-G). These results suggested that calreticulin directly stimulated cellular proliferation, an important characteristic for both generating a stratified epidermal layer and for populating the dermis with ample cells to produce cytokines and extracellular matrix proteins. Cellular proliferation is crucial for the repopulation of hypocellular diabetic wounds. Following this proliferation, the large numbers of cells produce collagens and other proteins important for remodeling the wounds. However, it was unclear in vivo as to whether this proliferative effect was a direct effect of calreticulin, or a secondary effect within the wound bed of cytokines produced by macrophages and keratinocytes.

Therefore, to this question, the effect of calreticulin on proliferation of human primary keratinocytes and human dermal fibroblasts was tested in vitro. In FIG. 7A, increasing concentrations of calreticulin (mixture of 5-CRT+ tag and 23-CRT+ tag) (0-200 pg/ml) were added to subconfluent synchronized primary keratinocytes in KBM (does not contain serum) on 96-well plate for 72 hours and the MTS Proliferation assay (CellTiter96®) was performed in triplicate. EGF (10 ng/ml) was used as a positive control. The data are expressed as fold increase±SEM compared to cells treated with KBM alone. After 72 hours, a dose-dependent increase in cellular proliferation was obtained with a peak response of 2.2-fold over untreated controls with 100 pg/ml calreticulin (FIG. 7A; n=5) that returned to normal control levels at 200 pg/ml. A similar peak response was obtained in unsynchronized cultures of keratinocytes that were incubated with calreticulin in basal media for 48 hours (n=2). The response was compared to human EGF (10 ng/ml) as a positive control which gave a smaller peak response of 1.3-fold in both assays.

Calreticulin (mixture of rabbit 5-CRT+ tag and 23-CRT+ tag, 0-200 ng/ml) stimulated synchronized subconfluent human primary dermal fibroblasts in a dose-dependent manner after 72 hours incubation yielding a peak response with 100 ng/ml calreticulin that was 2.4-fold higher than the untreated controls (FIG. 7B; n=7). This response was similar to FGF (5.0 ng/ml) as a positive control. It is notable that keratinocytes were more sensitive to calreticulin, with a peak response 1,000-fold less than the fibroblasts (100 pg/ml versus 100 ng/ml). In one experiment, the effect of recombinant human calreticulin (mixture of human 5-CRT+ tag and 23-CRT+ tag) on fibroblast proliferation was tested and the results showed identical specific activity as the recombinant rabbit calreticulin used for all the in vivo and in vitro experiments (FIG. 7C).

Calreticulin dose-dependently stimulated proliferation of human microvascular endothelial cells (HMVECs), after 24 hours incubation of the cells with 0-100 pg/ml calreticulin. Although the response obtained was small, the endothelial cells were highly sensitive to calreticulin with a consistent peak response of 30% increase in proliferation over the control with 1.0-25 pg/ml calreticulin (FIG. 7D; n=5), which was equal to 10 ng/ml VEGF (not shown).

Example 7: Calreticulin Induces Migration of Human Keratinocytes, Fibroblasts, and Mesenchymal Stem Cells In the cellular context, re-epithelialization and dermal remodeling in vivo are dependent on, and thus largely reflect, both the biological processes of cellular proliferation and migration.

Figure 8A:
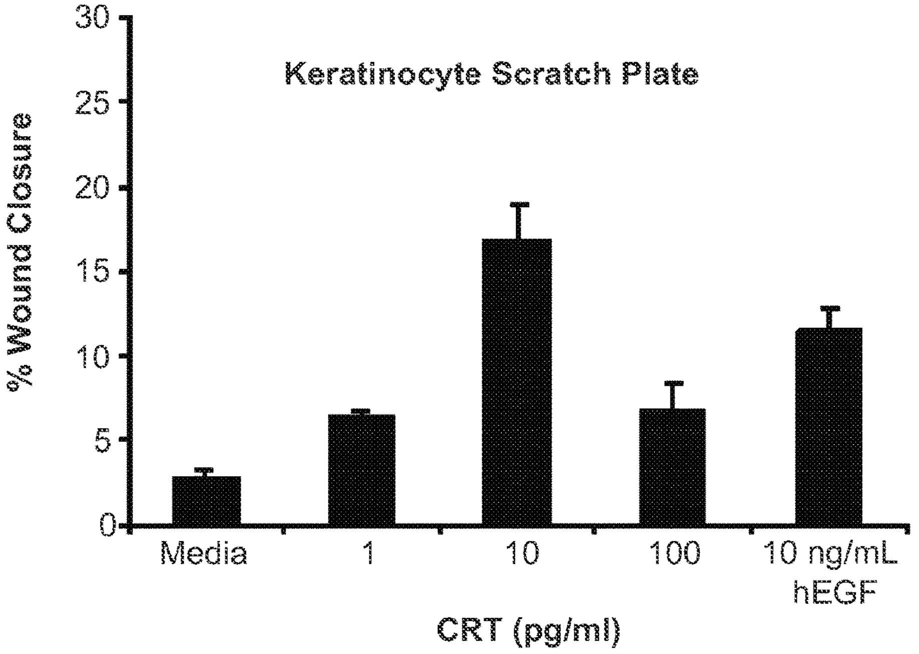
FIG. 8A shows a quantitative graph of the effect of increasing concentrations of calreticulin on primary human keratinocyte cell migration using the scratch plate assay (in vitro wound healing assay).
Figure 8B:
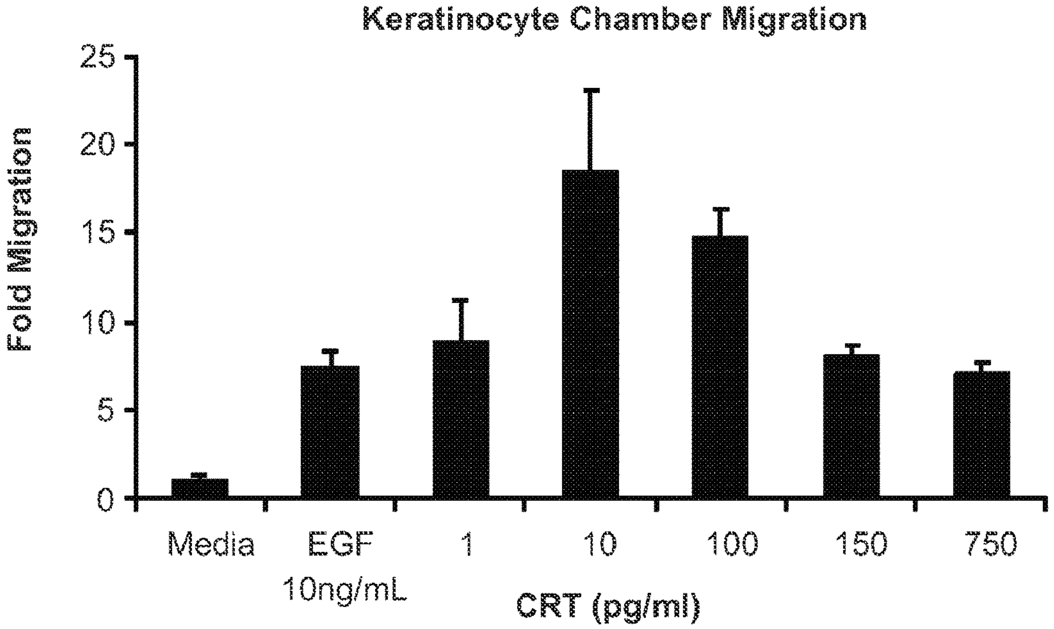
FIG. 8B shows a quantitative graph of the effect of increasing concentrations of calreticulin on concentration-dependent directed migration of primary human keratinocytes, using a thin-membrane chamber migration assay (ChemoTx® chamber system).

A standard scratch plate assay to simulate wound healing in vitro was employed to assess the effect of increasing concentrations of calreticulin on migration/motility on the human primary keratinocytes and fibroblasts. See, Lampugnani M G, Methods Mol Biol. 1999; 96:177-182; Huang et al., J Biol Chem. 1998; 273:25770-25776. The graph shown in FIG. 8A shows that calreticulin (mixture of rabbit 5-CRT+ tag and 23-CRT+ tag) (0-100 pg/ml) induced a dose-dependent increase in the number of keratinocytes (represented as percent wound closure) covering the wound at 48 hours after treatment. A peak response of 16.8%±1.53 wound closure with 10 pg/ml calreticulin was obtained compared to the EGF (10 ng/ml) positive control yielding 11.6% closure but, statistically significantly more than the media control, at 2% closure ($p \leq 0.003$; n=5). Similar results were obtained in experiments performed in the presence of 1-5 μg/ml Mitomycin C in the migration assay and thus, cellular proliferation did not appear to be a component of the migratory response to calreticulin. While the scratch plate migration assay is the gold standard for wound healing in vitro (Lampugnani M. et al. (1999) Methods Mol. Biol.; 96:177-182; Huang, C. et al. (1998) J. Biol. Chem.; 273:25770-25776), this assay only demonstrated that calreticulin induced motility. The chamber assay shows that calreticulin induces concentration-dependent directed migration. Interestingly, the same optimal dose was obtained for directed migration in chambers and the scratch plate was shown for both keratinocytes and fibroblasts. Using a thin membrane ChemoTx® chamber system, calreticulin (1-750 pg/ml) induced a concentration-dependent migration of keratinocytes through the membrane with an optimal dose of 10 pg/ml, which represents an 18.43-fold increase over the media control and a 2.5-fold increase over EGF, used as a positive control (FIG. 8B). The dose-dependent response to calreticulin was shown by the DAPI-stained nuclei of the keratinocytes on the bottom side of the membrane. It is notable that the identical peak response was obtained with both the scratch plate and directed migration assays using keratinocytes prelabeled with the fluoroprobe, Calcein, or nuclei stained with DAPI following migration of the keratinocytes through the membrane in response to calreticulin in the lower chamber.

Figure 9A:
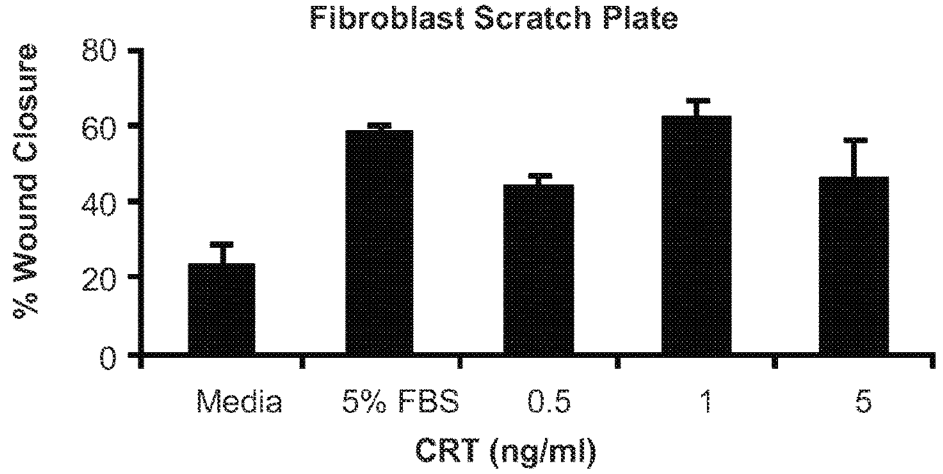
FIG. 9A shows a quantitative graph of the effect of increasing concentrations of calreticulin on human dermal foreskin fibroblasts using the scratch plate assay.
Figure 9B:
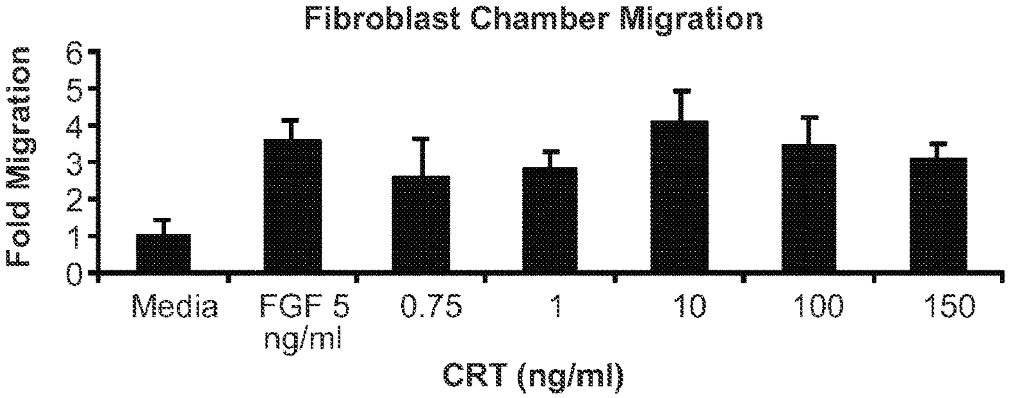
FIG. 9B shows a quantitative graph of the effect of increasing concentrations of calreticulin no a concentration-dependent directed migration of human dermal foreskin fibroblasts using a thin-membrane chamber migration assay (ChemoTx® chamber system).
Figure 9C:
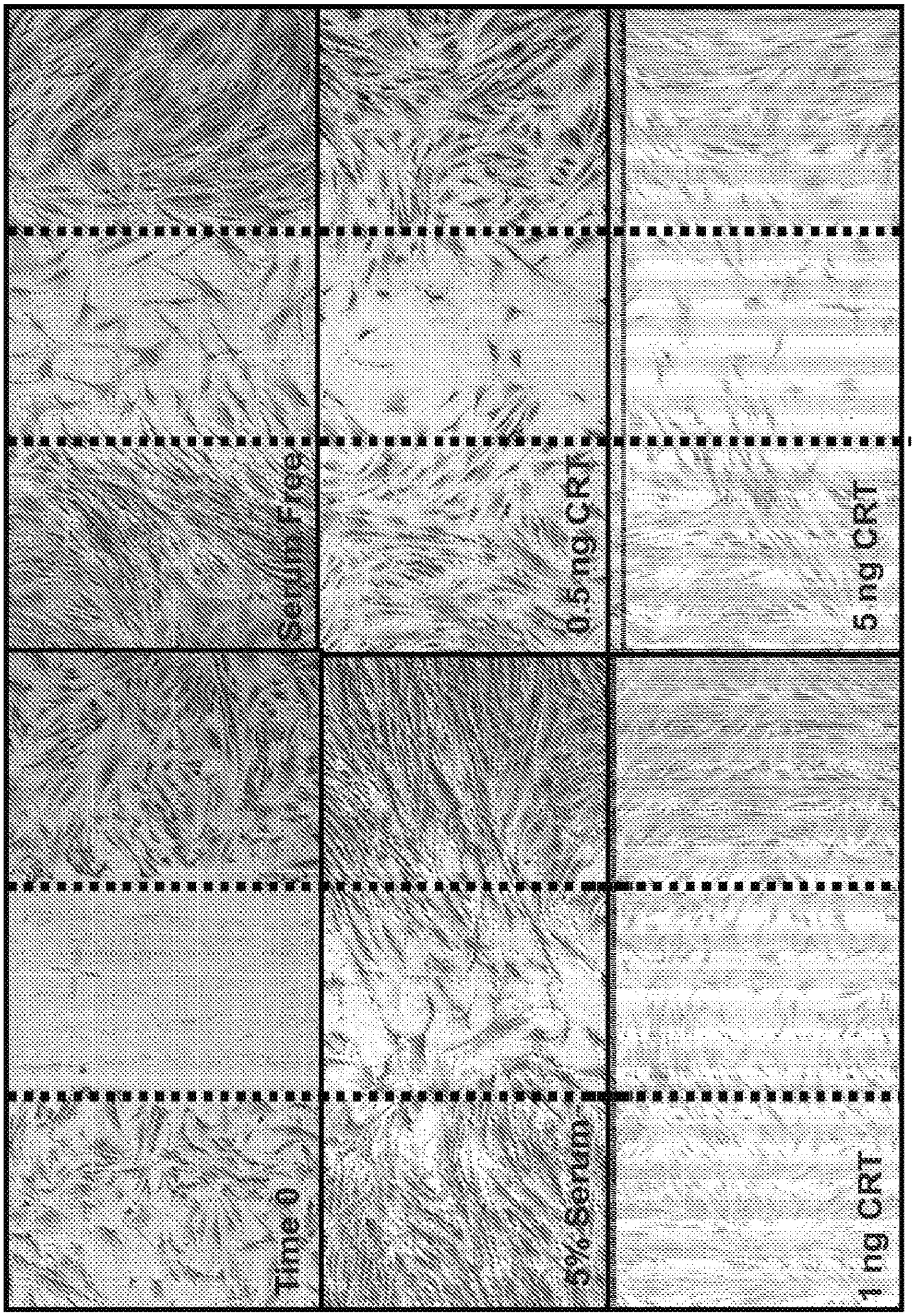
FIG. 9C shows a photomicrograph of the effect of increasing concentrations of calreticulin on the migration of human fibroblasts using the scratch plate assay (represented by FIG. 9A).

Similarly, as shown in FIG. 9, calreticulin induced a dose-dependent increase in migration of human fibroblasts in the scratch plate assay, with a maximal response of 62%±5.3 closure of the wound at 24 hours with 1 ng/ml calreticulin (FIG. 9A). The peak of the calreticulin-induced response at 1.0 ng/ml was greater than both the positive (5% FBS) and negative (MEM) controls ($p \leq 0.002$), which showed wound area closure by 58% and 24%, respectively (FIG. 9A; n=10). A photomicrograph of the scratch plate assay using fibroblast and reflected by the graph in FIG. 9A is shown in FIG. 9C. Note, one can observe the peak numbers of fibroblasts migrating into the scratch to cover the wound at 1.0 ng/ml. The affect of calreticulin on cellular migration of fibroblasts was unaffected by the addition of 8.0 [tM Mitomycin C. Using the human fibroblasts in the thin membrane ChemoTx® chamber system, either pre-labeled with Calcein or stained at the completion of the assay with DAPI, calreticulin (1.0 ng/ml to 100 ng/ml) induced directed migration of these cells in a concentration-dependent manner with a peak response at 10 ng/ml (FIG. 9B). Counting the cells per high power field, calreticulin induced a 4-fold induction of migration compared to the negative media control with a similar response elicited by the FGF positive control at 3.5 fold (n=3).

As with the proliferative response, keratinocytes demonstrated greater sensitivity to calreticulin than the fibroblasts as a 1,000 times lower dose was required for the maximal migratory response (10 pg/ml versus 1 ng/ml; compare FIGS. 8A and 9A) in the scratch plate assays. In addition, in this assay, it was shown that the migratory response was of a higher magnitude with the fibroblasts than the keratinocytes (60% versus 18%) (FIGS. 8A and 9A). This difference is likely related to the greater cell density at the time of performing the scratch on the plate as it was noted that the intensity of the response was not so disparate between these two cell types in the chamber migration assay. The proliferation and migration responses obtained in vitro provide mechanistic support for the histological effects shown in the calreticulin-treated wounds and importantly, specifically shows that calreticulin affects two important biological functions necessary for acute normal wound healing and also, the defects of chronic [diabetic] wounds. In the latter, the lack of wound cell proliferation and migration into the wounds is denoted by their hypocellularity. Furthermore, migration of keratinocytes over a wound for resurfacing (re-epithelialization) and fibroblasts into a wound to produce matrix proteins for filling in/remodeling the wound defect, are critical functions for wound healing and tissue repair, in general. These in vitro biological functions underscore the underlying mechanisms consistent with an agent that has widespread vulnerary effects to enhance healing of acute wounds with deep tissue loss and those characterized as chronic wounds.

The in vitro scratch plate assay was used to test whether human mesenchymal stem cells (CD34+/Col+)/fibrocytes were induced to migrate by calreticulin. The assay was performed as described above and percent wound closure was measured after 24 hrs. It is known that mesenchymal stem cells (MSCs) migrate from the bone marrow to sites of cutaneous injury contribute to the wound repair and regeneration process; they are involved in collagen induction and matrix formation and are required for normal wound healing—mesenchymal and endothelial stem cell migration into wounds is a known defect in diabetic healing because of lack of SDF-lalpha needed for homing to wounds. (Liu Z J, Zhuge Y, and Velazquez (2009) 5 Cell Biochem 106: 984). The cells were plated at $2\times10^4$ cells per well in a 24-well plate and a scratch/wound created in the cell monolayer with a pipette tip. Results show that calreticulin induces a dose-dependent and biphasic response in migration of MSCs/fibrocytes with peak responses at 250 pg/ml, 500 pg/ml. and 5 ng/ml, which is close to 2-fold greater than the serum-free media control (sfm). One representative graph of n=2 (FIG. 32).

Focal Adhesion Disassembly is important for cell migration. This response was shown to be mediated by the binding of N-terminal amino acids 19-36 in the N-domain of calreticulin to amino acids 17-35 of thrombospondinl (TSP1) in a co-receptor complex with lipoprotein receptor-related protein 1 (LRP1) that signals through Gi phosphoinositide-3 kinase-dependent ERK activation (Orr, A. W. et al (2003) J Cell Sci. 116:2917; On, A. W. (2002) J. Biol. Chem. 277: 20453-20460. To determine whether CRT-mediated migration involves thrombospondin-1 (TSP-1) and the LRP receptor for focal adhesion disassemble/migrationy, fibroblasts (CC-1070Sk) were tested for their response to increasing concentrations of calreticulin in the presence of 30M excess of the 19-36 peptide. Using both the scratch plate assay (left side of FIG. 35) and ChemoTx thin layer migration chambers (right side of FIG. 35), calreticulin-induced fibroblast migration induced by calreticulin was inhibited by the 19-36 peptide. This result indicates that TSP-1 mediated focal adhesion disassembly is involved in calreticulin-induced scratch plate wound closure and in calreticulin-induced concentration-dependent directed migration (FIG. 35) and that the N-Domain of calreticulin induces TSP-1-mediated migration.

Example 8: Calreticulin Induces Macrophage Influx of into the Wounds

Calreticulin is the obligate mediator of apoptotic cell clearance by both professional and non-professional phagocytes. See, Gardai et al., Cell 2005; 123:321-334. Since accumulation of dead cells and tissue are important retardants to the wound healing process, such a functional role for calreticulin in wound healing would be significant. Therefore, the effect of calreticulin on the influx of monocytes/macrophages, one of the major professional phagocytic cell types, into the porcine wounds was tested.

Immunohistochemical staining for macrophages revealed that wounds treated with both 1.0 mg/ml and 5.0 mg/ml calreticulin (mixture of rabbit 5-CRT+ tag and 23-CRT+ tag) contained numerous macrophages at 5 days post-wounding, when macrophage influx is typically at maximal levels. Quantitation of the number of macrophages in the tissues revealed an average of 48 and 51 cells per 300,000 $\mu m^2$ high power field (hpf) following treatment with 1.0 mg/ml and 5.0 mg/ml calreticulin, respectively (FIG. 10G). In contrast, an average of 19 and 15 macrophages per hpf was obtained in the buffer and PDGF-BB-treated wounds (FIG. 10G). Thus, there was approximately three times the number of macrophages per hpf in the granulation tissue of the calreticulin-treated compared to the buffer or PDGF-BB-treated wounds (FIG. 10G; $p\leq0.008$). After 10 days of repair in the normal wound model, the prevalence of macrophages was markedly diminished in all groups (data not shown) indicating that calreticulin does not prolong or sustain the influx of macrophages past the normal resolution of the inflammatory phase of repair. Following examination of the tissues from the steroid-challenged pigs at 7 days post-wounding, a similar increase in the influx of macrophages into the wounds was observed.

Figure 10A:
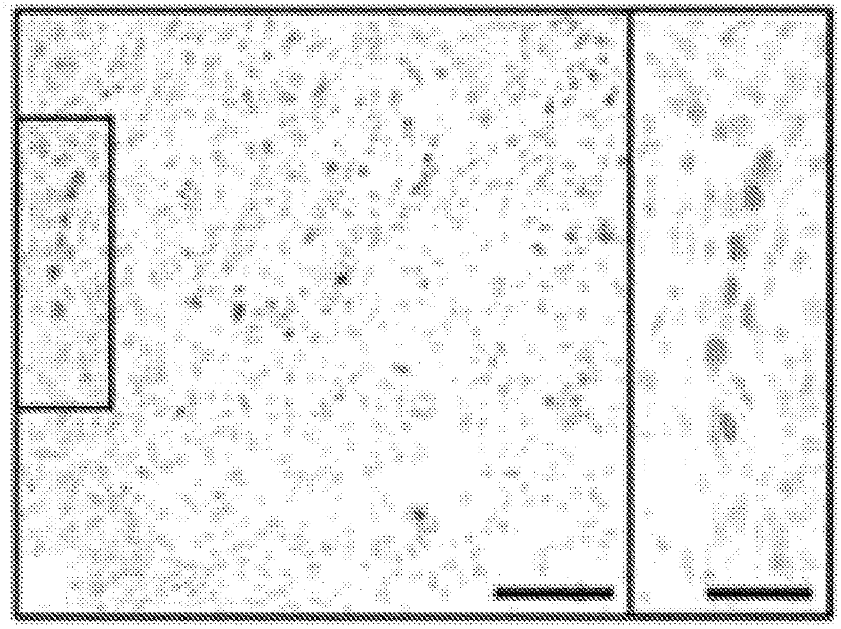
FIGS. 10A-10F are photomicrographs showing macrophage infiltration into porcine wounds (including those of cortisone-treated pigs to stimulate impaired diabetic wound healing) topically treated with calreticulin, Regranex® (PGDF-BB), and buffer, and immunostained with an antibody that detects macrophages.
Figure 10B:
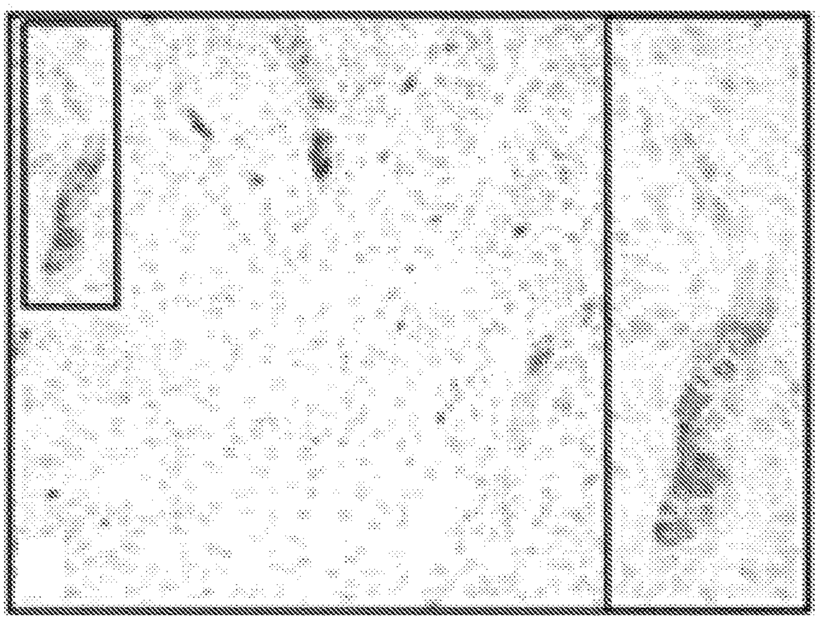
Figure 10C:
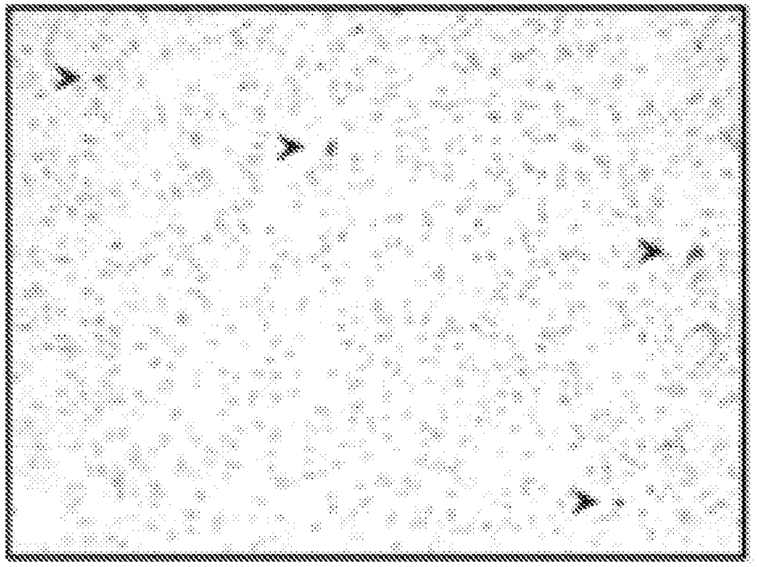
Figure 10D:
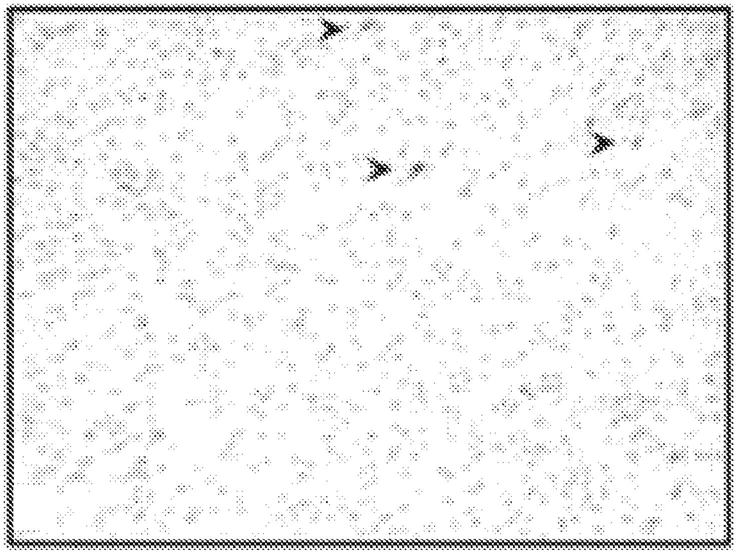
Figure 10E:
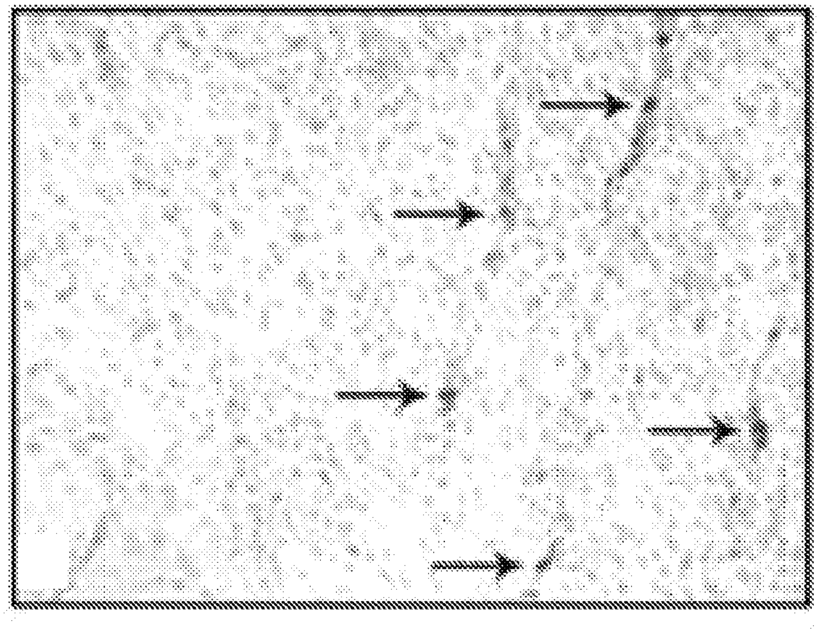
Figure 10F:
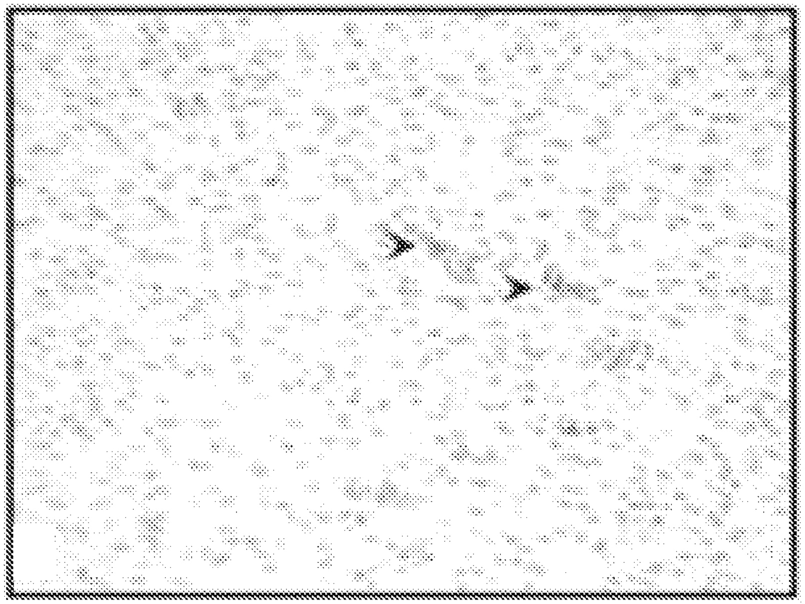
Figure 10G:
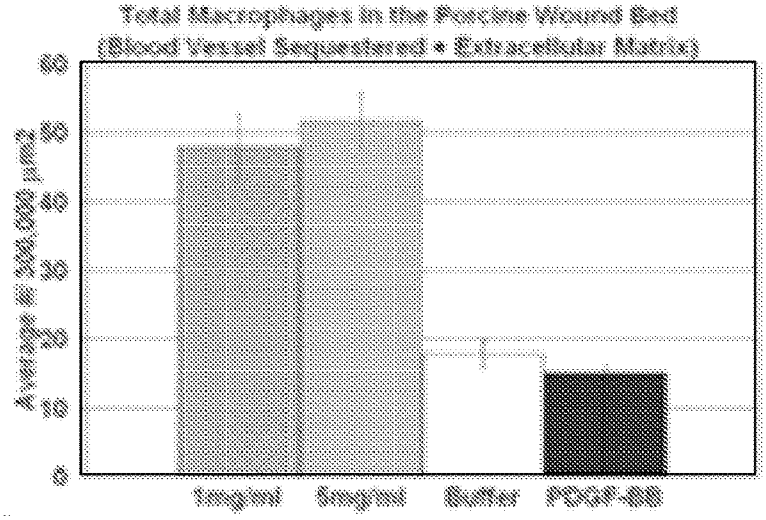
FIG. 10G is a quantitative graph showing the total number of macrophages in the porcine wound bed of calreticulin, buffer, or PDGF-BB treated wounds.
Figure 10H:
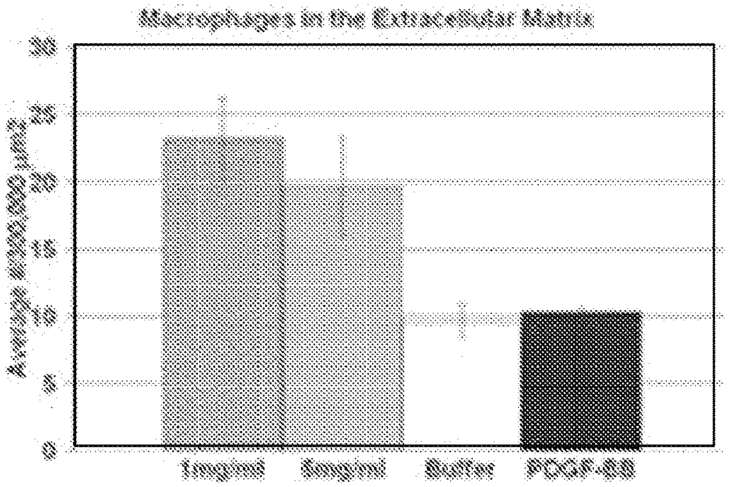
FIG. 10H is a quantitative graph showing the total number of macrophages in the extracellular matrix of the porcine wound bed of calreticulin, buffer, or PDGF-BB-treated wounds.
Figure 10I:
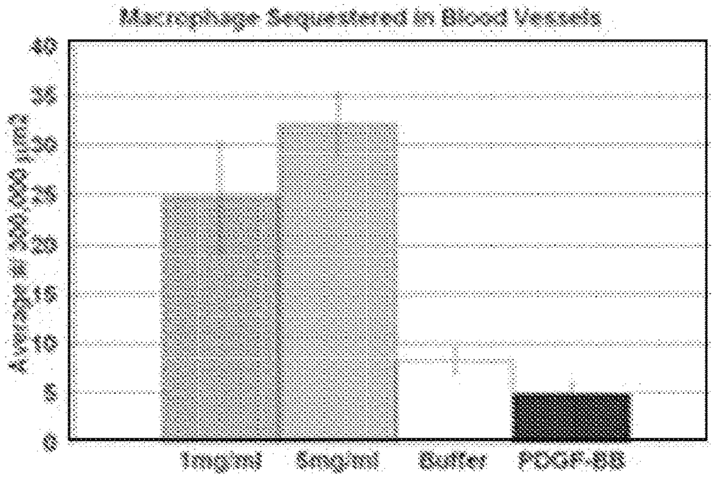
FIG. 10I is a quantitative graph showing the total number of macrophages sequestered in the blood vessels of the porcine wound bed of calreticulin, buffer, or PDGF-BB treated wounds.

Interestingly, many of the immunoreactive monocytes/macrophages were sequestered within the lumen of the capillary network of the neodermis in the healing wounds from both the normal and diabetic-model pigs (FIG. 10A, B, E). This prompted the counting of macrophages that were localized within the extracellular matrix of the neodermis (FIG. 10H; not inside capillaries) and subtracting this amount from the total (FIG. 10G) thus, providing the number of macrophages sequestered within the dermal capillary network (FIG. 10I). A statistically significant effect of both 1 mg/ml and 5 mg/ml calreticulin in recruiting macrophages within the vascular compartment ($p\leq0.001$) and extracellular matrix of the neodermis ($p\leq0.09$) was obtained compared to the PDGF-BB- and buffer-treated wounds (FIG. 10H,I). FIG. 10A,B,E show a clear example of the macrophage infiltration into the porcine wounds treated with calreticulin (1.0 mg/ml calreticulin [A]; 5.0 mg/ml calreticulin [B,E] compared to buffer [C,F] and PDGF-BB [D]. Importantly, calreticulin 5.0 mg/ml is shown to induce macrophage infiltration into the steroid-challenged pig wounds [E]. As a paucity of macrophage infiltration and other inflammatory cells is an important characteristic of the chronic wounds (wounds that do not demonstrate a normal rate of wound healing or do not heal), greatly contributing to lack of infection control and the absence of important cytokines and growth factors, these results are highly significant in terms of calreticulin as a wound healing agent specifically for chronic diabetic wounds since calreticulin specifically affects the migratory behavior of peripheral blood monocytes (precursors to differentiated macrophages) and macrophages (FIG. 10 and FIGS. 11A and 11B, below in Example 9).

Figure 11A:
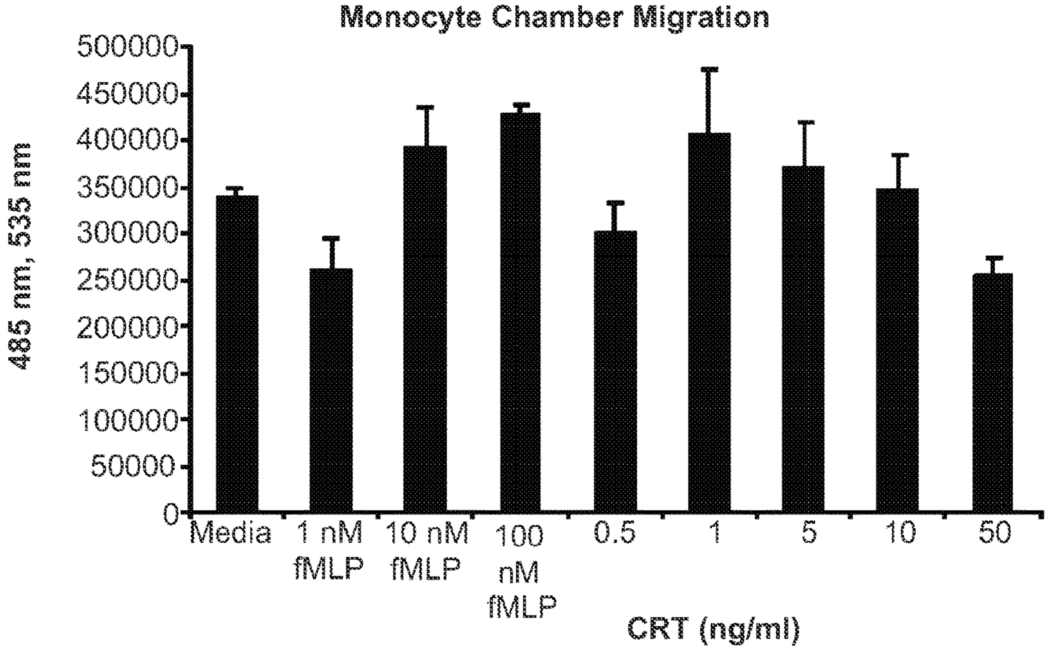
FIG. 11A is a quantitative graph showing human monocyte migration, in vitro, using the chamber migration assay and monocytes labeled with calcein, following treatment with media alone, fMLP or calreticulin.
Figure 11B:
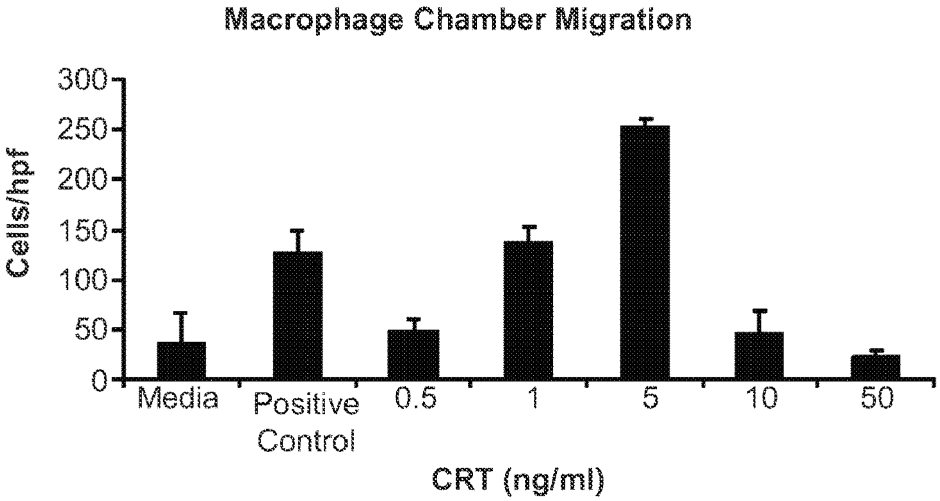
FIG. 11B is a quantitative graph showing the number of human macrophages that migrated, in vitro, following treatment with increasing concentrations of calreticulin, VEGF or fMLP (positive controls), or media using the chamber migration assay.

Example 9: Calreticulin Induces Concentration Dependent Directed Migration of Human Monocytes and Macrophages Since calreticulin treatment of both the normal and steroid-impaired wounds appeared to have a profound affect on recruiting monocytes/macrophages into the wound bed, ChemoTx® chamber migration assays were performed using both human THP-1 monocytes and their PMA-induced differentiated macrophage counterparts either prelabeled with Calcein or stained at termination of the migration assay with DAPI. Monocytes that were pre-labeled with the Calcein fluorescent probe, prior to performing the chamber migration assay, migrate in a concentration-dependent directed manner in response to calreticulin (mixture of rabbit 5-CRT+ tag and 23-CRT+ tag) (0.5-50 ng/ml with a peak response of 1.0 ng/ml which is equal to the highest dose of IMLP (100 nM) positive control (n=3) (FIG. 11A). As shown by DAPI-stained macrophages that have migrated within the membranes to 0.5-50 ng/ml of calreticulin, calreticulin induces a concentration-dependent directed migration of macrophages with a peak response between 1.0 and 5.0 ng/ml (FIG. 11B). Calreticulin at 5.0 ng/ml stimulated a 7-fold increase the number of cells that migrated through the membrane compared to the media control and a 2-fold increase over the positive controls of increasing doses of fMLP and VEGF, which were equal (FIG. 11B). Similarly, these in vitro results strongly support the findings in vivo (FIG. 10) and show an important role for calreticulin in the recruitment of monocytes from the circulation into the wound bed for the critical functions of cytokine production and wound debridement. Therefore, calreticulin affects monocytes/macrophages in two ways critical to wound healing: (1) CRT attracts monocytes into the wound from the circulation and adjacent tissues by inducing migration and (2) CRT mediates the uptake and clearance of dead cells and debris. See, Gardai et al., Cell 2005; 123:321-334, which is important for tissue debridement and healing.

Figure 12:
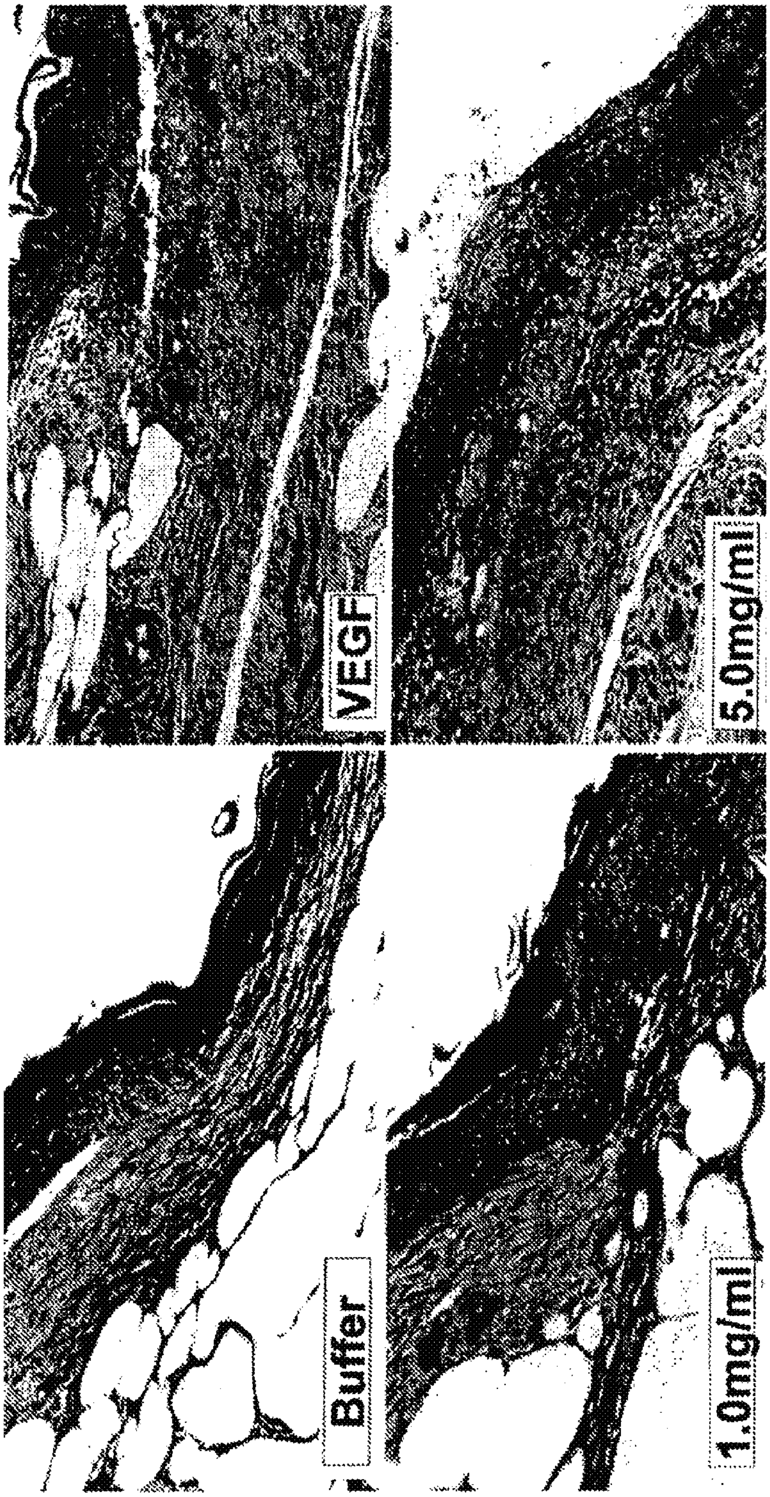
FIG. 12 shows a dose-response of topically applied calreticulin on granulation tissue formation in wounded mouse (db/db) tissue.

Example 10: Calreticulin Accelerates and Improves Wound Healing and Induces Hair Follicle Formation in an In Vivo Diabetic Mouse Model Initial murine experiments to determine the effective dosage of calreticulin (mixture of rabbit 5-CRT+ tag and 23-CRT+ tag) showed a peak effect at 5.0 mg/mL (0.5% CRT) which was significantly better than VEGF treated controls (FIG. 12). VEGF was chosen as a positive control after Galiano et al. reported that topical VEGF treatment improved diabetic wound healing and increased granulation tissue formation. Galiano et al. (2004) Am. J. Pathol.; supra. The 5.0 mg/mL dose was used for all subsequent experiments. Because calreticulin is a calcium binding proteins and the calcium present maintains the appropriate conformation of the molecule, it was surmised that calcium was most likely required for calreticulin biological functions. Therefore, the wounds were treated with calreticulin in buffers with (3 mM) and without (0 mM) calcium. However, initial experiments showed no difference in time to closure in vivo with the presence or lack of calcium, presumably because of sufficient levels of calcium found within the wounds. Thus, for all experiments, 3 mM calcium was present in the buffer of the calreticulin added to the diabetic wounds in vivo.

Figure 13:
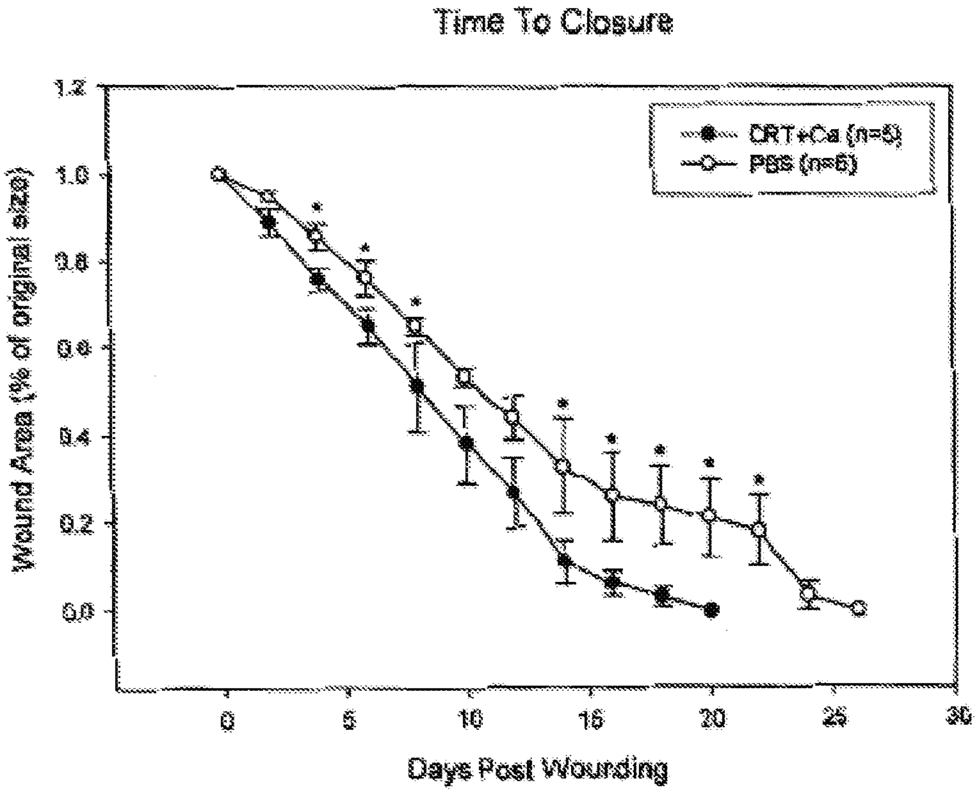
FIG. 13 is a quantitative graph of a time course of complete wound closure in calreticulin and buffer-treated excisional, full-thickness wounds of diabetic mice.

FIG. 33 A shows examples of gross wounds treated with calreticulin or buffer, for the first 4 days following experimentally-induced injury, at 10 and 28 days post-wounding. The method is described in Michaels et al (2007) Wound repair and Regeneration 15:665. The calreticulin-treated wounds (lower panels) healed more rapidly and appeared more mature than the buffer-treated controls (upper panels) (shown are two examples of a total of 12 wounds). The histology of the calreticulin-treated wounds shown in FIG. 33B demonstrates granulation tissue formation and far better wound closure in the calreticulin-treated wounds at 10 days following injury (Hematoxylin and Eosin staining) By 28 days, all calreticulin-treated wounds were completely healed (FIG. 33A) with normal histology, surface cornification, and long normally thick black hair was observed within the interior of the splint. In FIG. 33B showing the hisotology of the wounds, most buffer-treated wounds showed complete closure. However, the calreticulin-treated wounds showed regeneration of hair follicles and epidermal appendages (lower right panel marked by arrows), which was not observed in the buffer-treated wounds (FIG. 33 B). The interrupted panniculus carnosus (muscle layer under the dermis in loose skin hairy animals such as rodents) is shown by black diamonds indicating where the excisional wound was originally made. De novo hair follicle regeneration has been shown to be a Wnt-dependent process due to epidermal cells in the tissue adjacent to the wound adopting a stem cell phenotype and migrating into the wound (Ito, M. et al (2007) Nature 447:316-320). However, different from the calreticulin wound size at 6 mm, a 0.25 cm wound was required to provide a microenvironment that could induce hair re-growth. Moreover, the mouse hair that re-grew was white, lacking melanocytes where as the calreticulin-treated wounds showed black hair regrowth in the C57 Black mice. Therefore, as shown herein, calreticulin induces marine hair re-growth after full-thickness excisional wound injury. A time course experiment was performed to evaluate the rate of closure for the calreticulin-treated versus untreated wounds. Time to closure of the calreticulin treated wounds was significantly improved over the untreated wounds (17.6 days vs. 23.2 days, $p \leq 0.045$, n=6 for each time point) (FIG. 13). There was a marked difference in improvement of closure of the calreticulin treated wounds. Statistically significant differences were obtained by day 14 and thereafter. This difference was also observed by gross analysis of the wounds at day 3, 5,7, 10, 14, 21, and 28 after injury.

Figure 14:
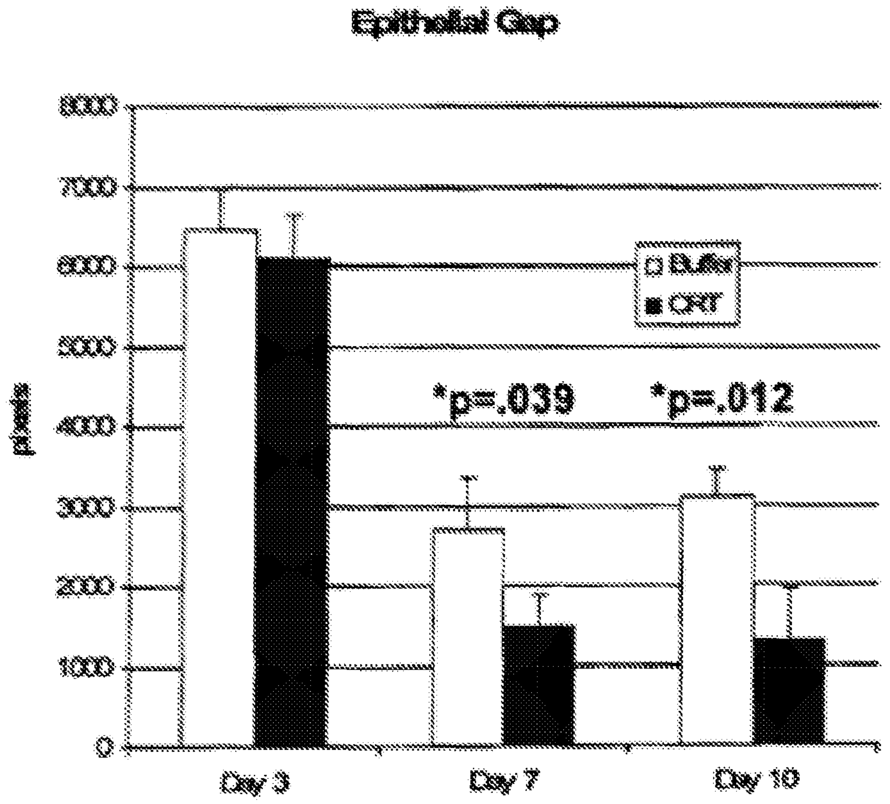
FIG. 14 is a quantitative graph showing reduction in the size of the epithelial gap (representing wound re-epithelialization) at days 3, 7, and 10 in calreticulin or buffer-treated wounds.

The two major components of wound healing are granulation tissue formation, produced by fibroblasts and other cells in the dermis that have migrated into the wound, and accelerated migration of the keratinocytes over the wound to close the epithelial gap. Re-epithelialization is a critical early marker of successful wound healing and it is aided by abundant granulation tissue formation, termed the 'micro-exudate carpet'. Calreticulin induces a significantly faster rate of re-epithelialization by day 7 ($p \leq 0.039$, n=6) and day 10 (p=0.012, n=6) (FIG. 14). By day 14, both the treated and untreated wounds were re-epithelialized, though not closed.

Figure 15:
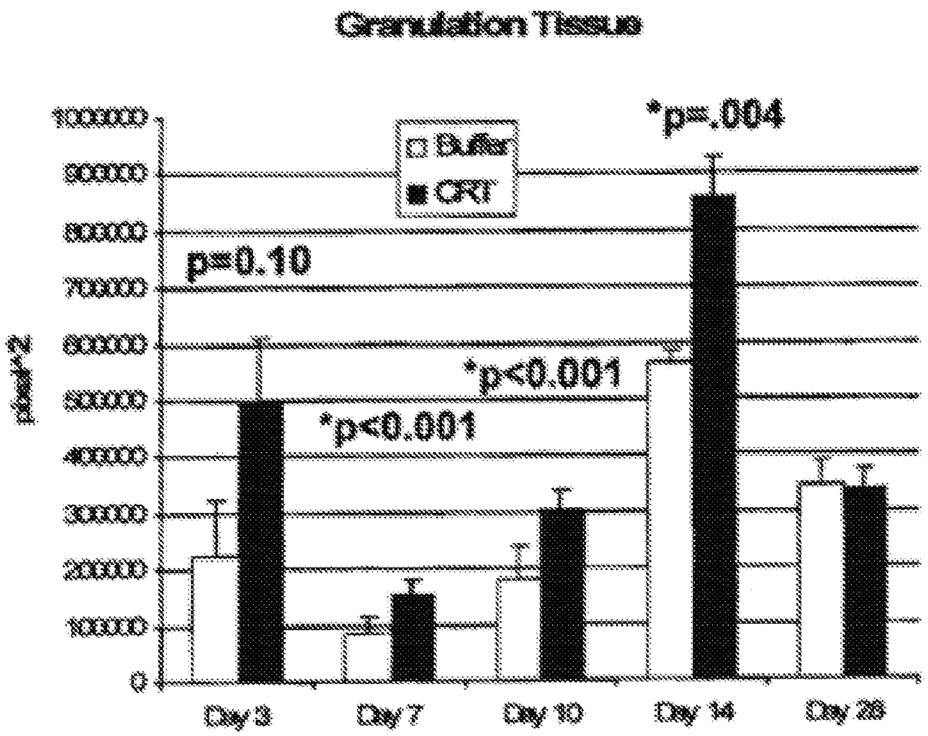
FIG. 15 is a quantitative graph showing the area of granulation tissue formation (neodermis) in buffer and calreticulin-treated murine exicisional full-thickness wounds on days 3, 7, 10, 14, and 28 post-wounding in diabetic mice.

By histological examination and quantitative analysis of the granulation tissue area, granulation tissue was significantly increased in calreticulin treated wound by day 7 (152226±27816 vs. 87624±25773 pixels$^2$ $p \leq 0.001$) and persisted through day 14 (857108±73784 vs. 564014±23982 pixels$^2$ p=0.004) (FIG. 15 and as observed in FIG. 12). The calreticulin treated wounds displayed increased collagen deposition and improved collagen maturation, as shown by picrosirius red staining under polarized light (data not shown).

The process of keratinocyte closing of the epithelial gap occurs not only due to migration of the cells over the wound, but also through the increased proliferation of the basal keratinocytes. Ki-67 staining (a marker of proliferation) of diabetic tissues showed intense areas of proliferating cells in the basal layer of the keratinocytes as well as in the fibroblasts explaining the high cellularity in the dermis of the wounds treated with calreticulin (not shown). In contrast, this was not observed in the buffer treated control wounds (not shown). Ki-67 immunostaining of basal keratinocytes and fibroblasts was identical in the calreticulin treated wounds of both the pig and mouse. Because cells that proliferate cannot be migrating (Werner, S. et al. (2000) Experimental Cell Research; 254:80-90; Onuma, H. et al. (2001) Archives of Dermatological Research; V293:133-138), the basal keratinocytes may be precursors to both m##igrating cells and those that rise from the basal layer to form the upper layer of the epidermis (i.e., stratum spinosum and corneum). The fact that both the pig (see Example 5, FIG. 6) and mouse showed identical Ki-67 staining pattern confirms a role for calreticulin in inducing proliferation of keratinocytes and cells of the dermis.

Example 11: Calreticulin Induced Keratinocyte, Fibroblast and Macrophage Migration, and Keratinocyte and Fibroblast Proliferation in an In Vitro Diabetic Model In these experiments, human fibroblasts and ketatinocytes were used as markers of granulation tissue formation and epithelialization, respectively. The experiments used a model of high (4.5 g/L) and normal level glucose environments to simulate the diabetic milieu in vivo. Cells grown in a high glucose environment for a minimum of 3 weeks are similar to isolated diabetic cells (cells derived from diabetic mammals) and display impaired proliferation, migration, and cytokine production, as in diabetes. Lerman et al., Am J Pathol 2003, 162:303-312; Deveci et al., British Journal of Dermatology 2005, 152:217-224; Loots et al., Archives of Dermatological Research 1999, V291:93-99. Macrophages, mediators of inflammatory signaling and phagocytosis, were also observed under these conditions.

Figure 16:
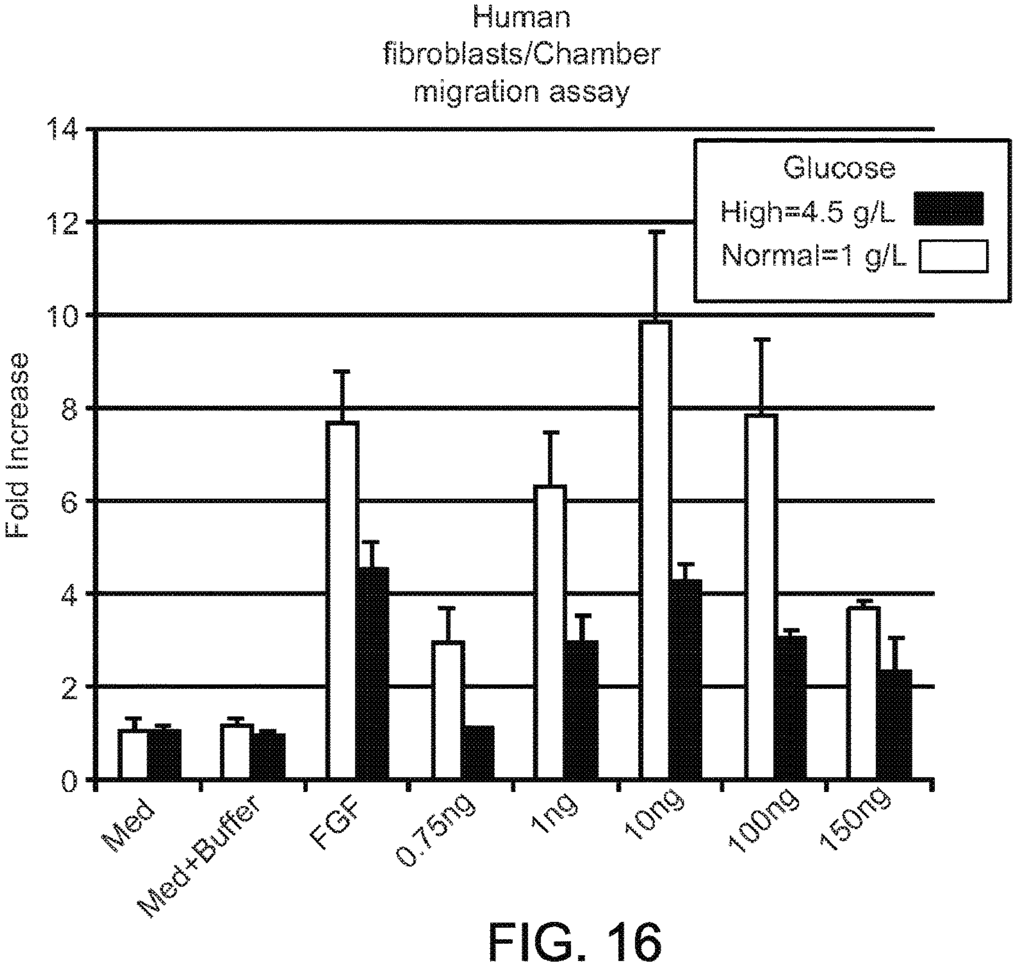
FIG. 16 is a quantitative graph depicting concentration-dependent directed migration (thin-membrane chamber assay) of human fibroblasts cultured in high or normal glucose conditions following treatment with increasing doses of calreticulin (CRT) compared to FGF (positive control), measured as fold induction (number of cells per high power field).
Figure 17:
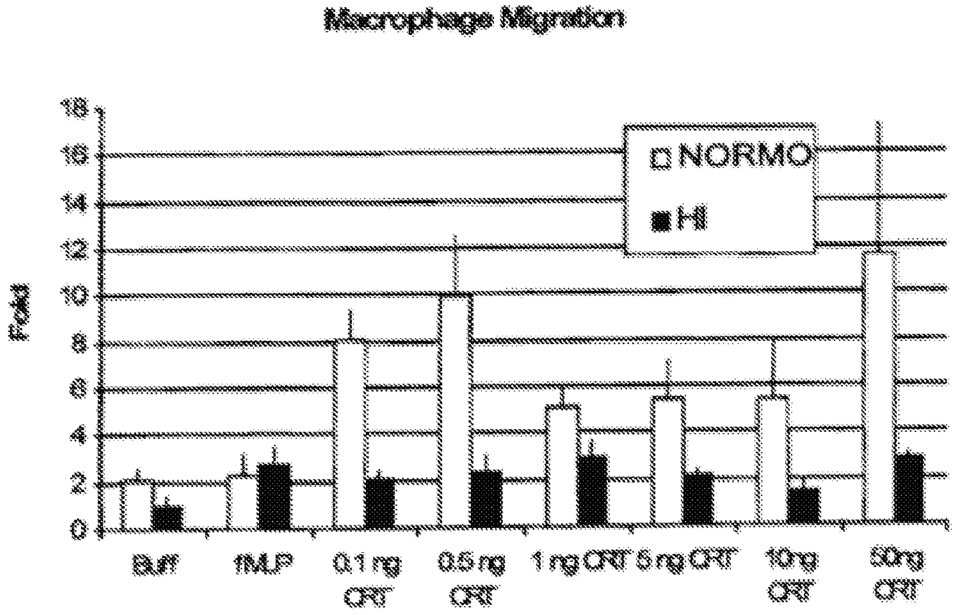
FIG. 17 is a quantitative graph showing concentration-dependent directed migration (thin-membrane chamber assay) of macrophages cultured in high (HI) or normal (Normo) glucose conditions following treatment with increasing doses of calreticulin (CRT) and measured as fold migration over media negative control compared to fMLP (positive control).
Figure 18:
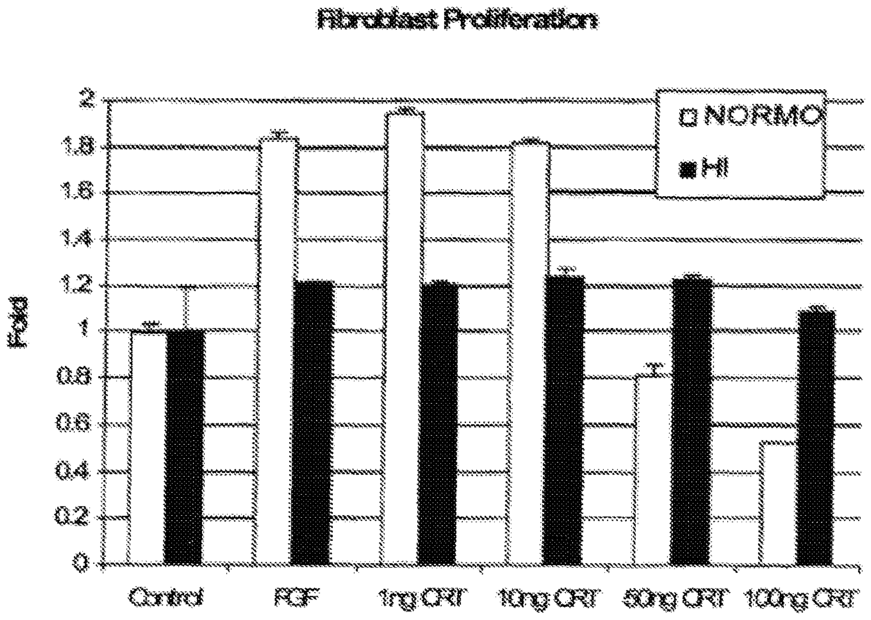
FIG. 18 is a graph depicting the proliferation of human fibroblasts cultured in high (HI) or normal (Normo) glucose conditions following exposure to increasing dose of calreticulin, FGF (positive control), or buffer.

Using wound cells, described above, cultured in high glucose conditions, calreticulin-mediated functions were compared to wound cells grown in normal glucose conditions in vitro migration and proliferation assays. Calreticulin (mixture of rabbit 5-CRT+ tag and 23-CRT+ tag) induced chemotaxis of human fibroblasts (FIG. 16) and macrophages (FIG. 17) with a maximal effect at 10 ng/ml and 0.5 and 50 ng/ml (a biphasic response), respectively, in normal levels of glucose. Importantly, calreticulin partially restored the migratory capacity of these wound cells assayed under high glucose conditions, which exhibited decreased migration relative to positive controls (FIGS. 16-17). Further, calreticulin stimulated proliferation of fibroblasts (FIG. 18) with a maximal induction of 1.9-fold at 1 ng/ml for normal glucose conditions and 1.2-fold (the same response was obtained for the FGF positive control) at 1.0 ng/ml under high glucose conditions. Of note, the induction with calreticulin was higher than FGF (1.9 fold vs. 1.8 fold) with fibroblasts under normal glucose condition (n=3).

The results of these in vitro experiments show that calreticulin had a significant affect on proliferation and migration of fibroblasts and macrophages in normal and high glucose environments. These findings are consistent with the in vivo findings that calreticulin increases: the rate of diabetic wound closure, diabetic wound cellularity and diabetic wound granulation tissue formation, all critical characteristics essential for wound healing.

Figure 19:
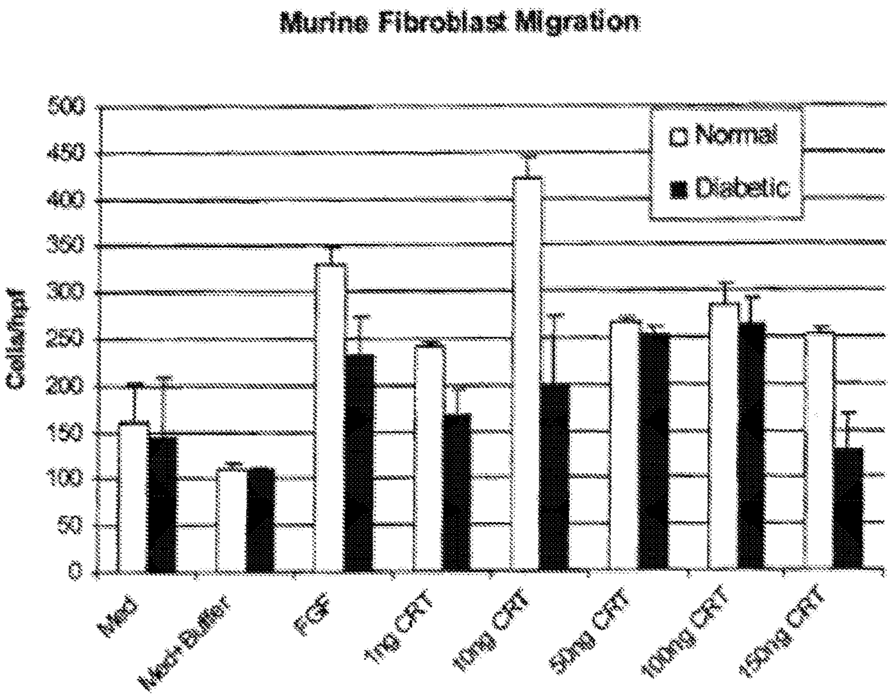
FIG. 19 is a graph showing concentration-dependent migration of murine fibroblasts isolated form normal wild type mice compared to fibroblasts isolated from diabetic skin in a thin-membrane chamber migration assay following exposure to increasing doses of calreticulin, FGF, or buffer, and measured as number of cells per high power field (hpf).

Fibroblasts were isolated from normal and diabetic (db/db) mice, as previously described above. As these cells were isolated from genetically homologous mice to those used in the in vivo work, the effects of calreticulin on diabetic cells could be determined. It was hypothesized that these diabetic cells, similar to human fibroblasts grown in a high glucose environment (FIG. 16), would also show a reduction in migration in vitro, because the dermis of a diabetic (db/db) mouse has decreased migration of fibroblasts into the wound bed compared to normal mice. Diabetic murine fibroblasts exhibited a reduction in migration compared to normal murine fibroblasts (FIG. 19; n=6). Addition of calreticulin resulted in a peak of migration at 10 ng/mL for the normal murine fibroblasts and 100 ng/ml for the diabetic murine fibroblasts, though significantly fewer diabetic cells migrated than the normal cells.

Therefore, although the diabetic murine fibroblasts responded to calreticulin in a dose-dependent manner, these cells were less sensitive requiring a ten times higher concentration of calreticulin for the peak response and moreover, the cells gave a less robust response (440 ceLL/hpf compared to 270 cells/hpf).

While studies have shown that diabetic fibroblasts are impaired in their capacity to undergo migration (Lerman, O. Z. et al. supra), this experiment revealed that they may require higher doses of calreticulin to significantly increase their migration. Whereas the diabetic fibroblasts responded less well to calreticulin in these migration experiments, these studies suggest that calreticulin has the potential to improve diabetic wound healing, as was observed in vivo, by increasing migration of fibroblasts into the diabetic wound.

In consideration of calreticulin inducing keratinocyte migration and proliferation in vivo in both the diabetic porcine and murine wound healing models (FIGS. 1,2,6,13, 14), calreticulin affects a specific trait of diabetic wounds, namely that they are poorly re-epithelialized due to lack of keratinocyte proliferation and migration.

The in vivo results that calreticulin improves wound healing in diabetic animal models and the in vitro results of the strong effect of calreticulin on increasing both the migratory and proliferative response of keratinocytes and fibroblasts from diabetic skin, support the use of calreticulin as a therapeutic agent for diabetic (and impaired) wound healing and sets an example for its positive wound healing effect for other chronic wounds such as, but not limited to, pressure ulcers and venous and arterial stasis ulcers.

Figure 20A:
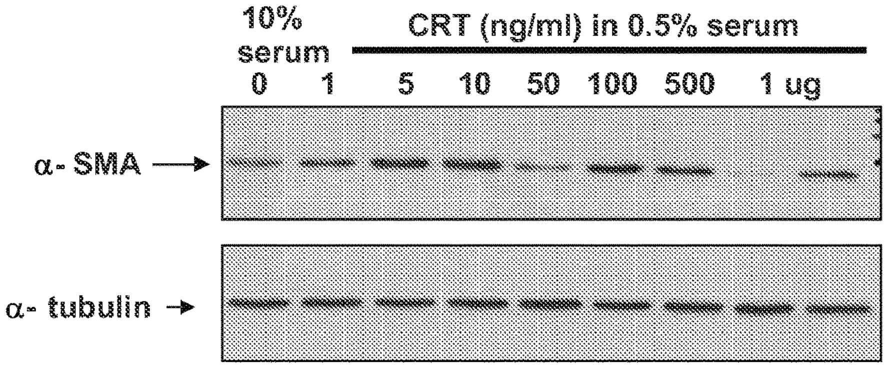
FIG. 20A is a Western blot (immunoblot). The cell lysates are applied to SDS-PAGE (polyacrlyamide gel electrophoresis) that separates proteins by their molecular weight size. The proteins are electro-transferred to a PVDF membrane and the membrane is incubated with a specific antibody to identify the protein. This figure shows an immunoblot for alpha-smooth muscle actin (SMA) induction of expression in human dermal fibroblasts treated with increasing concentrations of calreticulin for 24 hours. Cell lysates were prepared with RIPA buffer. Equal protein concentrations were subjected to immunoblot analysis using an antibody to SMA.
Figure 20B:
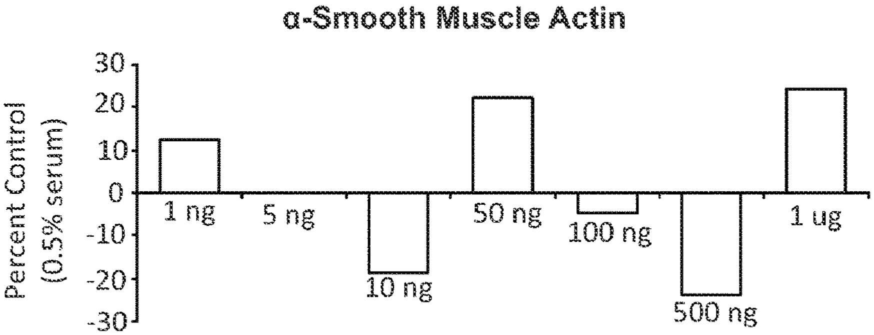
FIG. 20B is a graph representing the densitometric scan of the blot shown in FIG. 20 A.

Example 12: Calreticulin Induced α-Smooth Muscle Actin (α-SMA) as a Biphasic Response in Human Fibroblasts Induction of fibroblasts into a myofibroblast phenotype is consistent with wound healing as these cells are involved in wound contraction and in the deposition of collagen as well as other extracellular matrix proteins. Smooth muscle cell actin (SMA) is expressed by fibroblasts that have migrated into the wound (myofibroblasts). Myofibroblasts are distinguished by their expression of a-smooth muscle actin (α-SMA). To determine whether calreticulin functions to induce the myofibroblast phenotype, human dermal fibroblasts were treated in vitro with increasing concentrations of calreticulin (mixture of rabbit or human 5-CRT+ tag and 23 CRT+ tag) for 24 hours and cell lysates prepared with RIPA buffer. Fibroblasts are treated in the presence of 0.5% fetal bovine serum as a requirement for their vitality. Equal protein concentrations were subjected to SDS-PAGE analysis (5-20% acrylamide gradient gel) followed by immunoblot analysis using an antibody to α-SMA (FIG. 20A). As shown, calreticulin induces a biphasic (50 and 500 ng/ml) response of α-SMA expression with peak responses shown by the FIG. 20B graph, which represents a dens itometric scan of the blot. SMA expression is normalized to the quantity of α-tubulin in each sample (well). Thus, calreticulin induced the myofibroblast phenotype, important in wound contraction (for wound closure), thereby contributing to accelerated and enhanced wound repair.

Example 12: Calreticulin Increased Integrin Expression for Cellular Migration (Alpha5 on Keratinocytes and Betal on Fibroblasts)

Figures 21A, 21B, 21C, 21D:
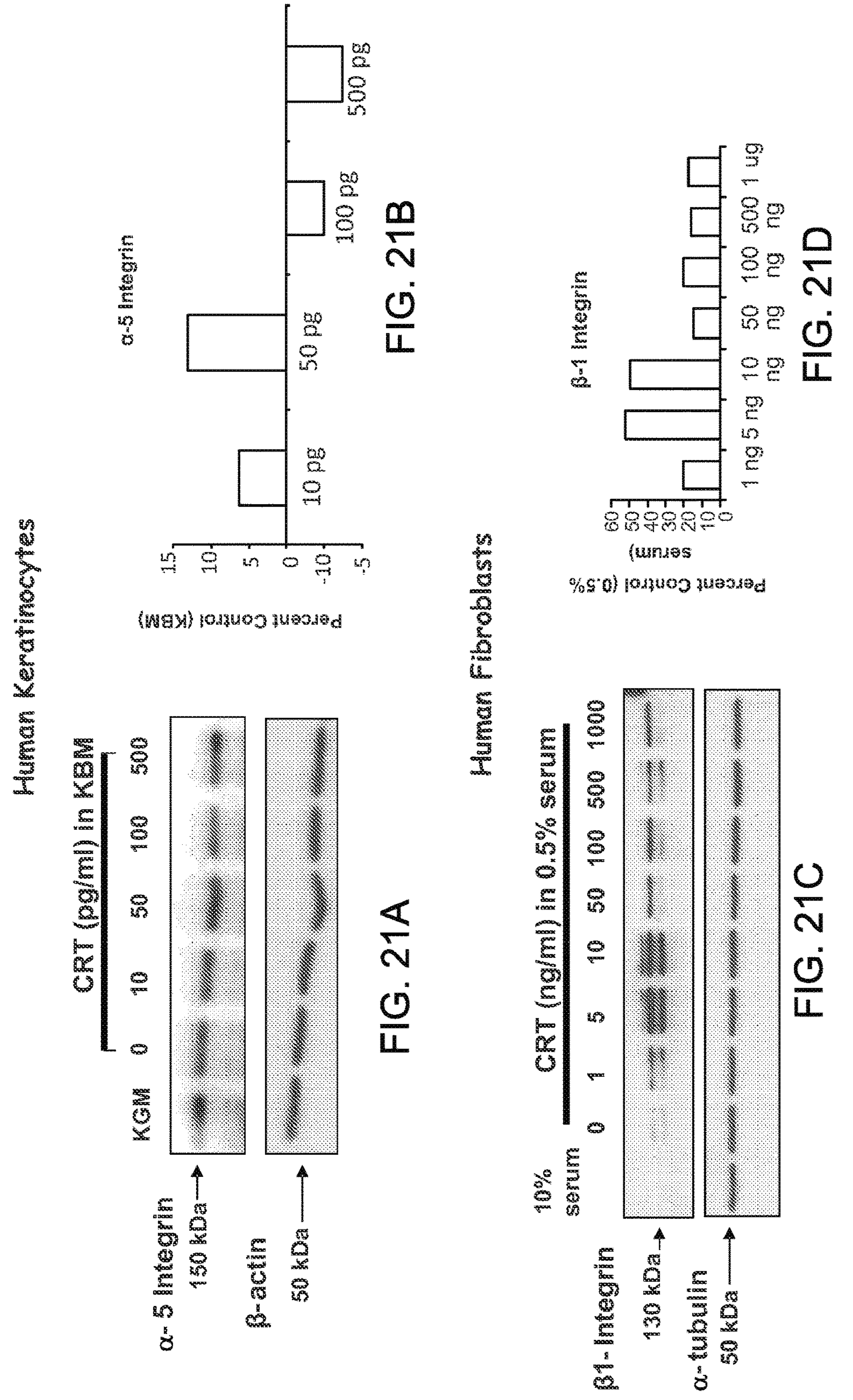
FIG. 21A shows an immunoblot of alpha (α) 5 and beta (β) 1 induction of integrin expression in primary human keratinocytes treated with increasing doses of calreticulin for 24 hours, lysed in RIPA buffer and subjected to α5-integrin antibodies.
FIG. 21C shows an immunoblot of human fibroblasts treated with increasing doses of calreticulin for 24 hours, lysed in RIPA buffer and subjected to β1-integrin antibodies.
FIG. 21B is a graph representing a densitometric scan of the blot shown in FIG. 21A, measuring the intensity/quanitity of the α-5 integrin expression normalized to β-actin.
FIG. 21D is a graph representing a densitometric scan of the blot shown in FIG. 21C; β-1 integrin expression is normalized to α-tubulin.
Figures 22A, 22B, 22C, 22D:
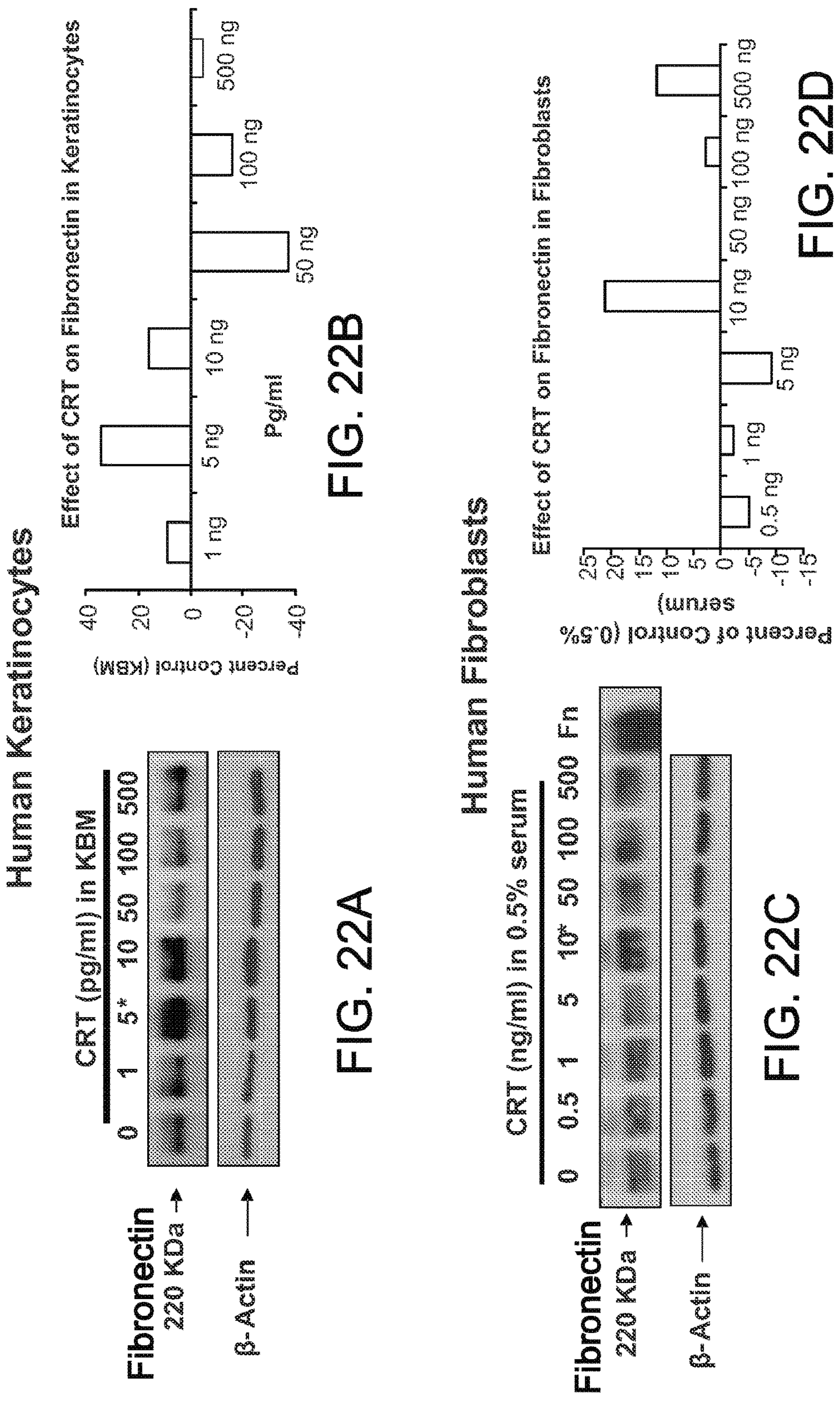
FIG. 22A shows an immunoblot of induction of fibronectin expression in human keratinocytes treated with increasing doses of calreticulin for 24 hours, lysed in RIPA buffer and subjected to immunoblot analysis using polyclonal fibronectin antibodies.
FIG. 22C shows the immunoblot of human fibroblasts treated with increasing doses of calreticulin for 24 hours, lysed in RIPA buffer and subjected to immunoblot analysis using polyclonal fibronectin antibodies.
FIG. 22B is a graph on the blot shown in FIG. 22A, representing a densitometric scan measuring the intensity/quantity of fibronectin expression normalized to β-actin.
FIG. 22D is a graph representing a densitometric scan of the blot shown in FIG. 22C.

Integrins, composed of two chains (alpha and beta), mediate cell adhesion and migration on most adherent cell types. α5 integrin and β1 integrin are upregulated during migration of keratinocytes and fibroblasts into the wound bed. Since calreticulin induced migration of these cells, this experiment was performed to determine whether calreticulin could induce integrin expression in vitro. Primary adult human epidermal keratinocytes (CC2501-Cambrex-Lonza) or human foreskin fibroblasts (CCD 1070SK; from ATCC) were treated with increasing doses of calreticulin (mixture of rabbit or human 5-CRT+ tag and 23-CRT+ tag) for 24 hours (serum-free) and cell lysates, prepared in RIPA buffer, were analyzed for integrin expression by SDS-PAGE (5-205 acrylamide gel) and immunoblotting with antibodies to α5 integrin by keratinoccytes and β1-intergrin by fibroblasts (FIGS. 21 A and B, respectively). The intensity of the bands (quantity) of integrin was measured by densitometric scans normalized to (β-actin or α-tubulin (FIGS. 21C,D). As shown, calreticulin induces the expression of integrins involved in migration of keratinocytes and fibroblasts into the wound with peak responses of 50 pg/ml for α5 integrin by keratinocytes and 5-10 ng/ml of β1 integrin by fibroblasts, as shown. KBM=keratinocyte basal media. These results suggest that keratinocytes and fibroblast migrate over and into wounds, respectively, by upregulating the expression of integrins. As shown in FIGS. 22A and 22B, keratinocytes and fibroblasts (FIGS. 22*c* and 22D) produce fibronectin in response to calreticulin. This suggests that alpha5 and beta 1 integrins are upregulated by these cells to migrate over the fibronectin that they secrete.

Example 13: Calreticulin Induced the Expression of Fibronectin in Human Keratinocytes and Dermal Fibroblasts Fibronectin is an important extracellular matrix protein. Increased fibronectin expression is important for granulation tissue formation (formation of the neodermis) critical to wound remodeling. To determine whether calreticulin induced fibronectin as a mechanism involved in its ability to increase granulation tissue in murine and porcine wounds, keratinocytes and fibroblasts were treated with increasing concentrations of calreticulin for 24 hours and cell lysates analyzed by immunoblotting, using a polyclonal antibody to fibronectin. As shown, calreticulin (mixture of rabbit or human 5-CRT+ tag and 23-CRT+ tag) induced fibronectin expression in both keratinocytes (FIGS. 22A,C) and fibroblasts (FIGS. 22B,D) with peak responses of 5 ng/ml (biphasic) and 10 ng/ml, respectively as shown. Note: calreticulin induced fibronectin expression with the same peak concentration that induces migration of keratinocytes (5-10 pg/ml) and fibroblasts (10 ng/ml), substantiating the role for calreticulin in enhancing wound healing in vivo through the migration of cells into the wound. Moreover, calreticulin induced alpha5 and beta 1 integrin expression in a pg/ml and ng/ml for keratinocytes and fibroblasts, respectively. These integrins specifically bind fibronectin for migration, as described above in Example 12. It is notable that calreticulin affects keratinocytes at pg/ml levels and fibroblasts at ng/ml levels, as this supports the specificity of calreticulin-induced responses.

Figure 23A:
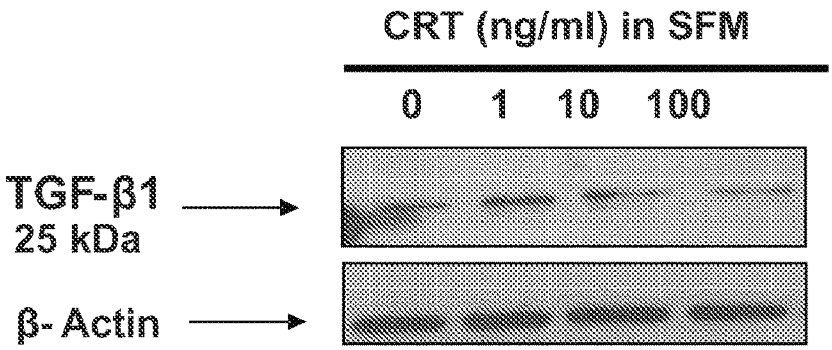
FIGS. 23A, 23B, 23C show immunoblots of induction of TGF-β1, TGF-β2, and TGF-β3 expression in human fibroblasts treated with increasing concentrations of calreticulin for 24 hours, lysed in RPIA buffer and subjected to immunoblot analysis using polyclonal antibodies to the individual TGF-β isoforms (TGF-β1, TGF-β2, TGF-β3).
Figure 23B:
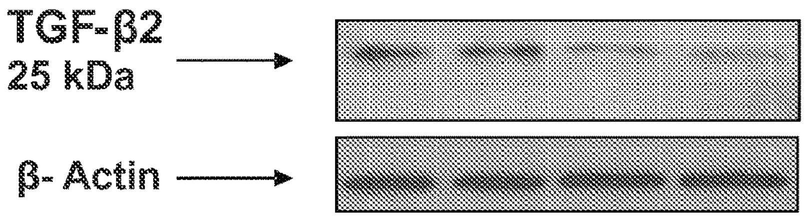
Figure 23C:
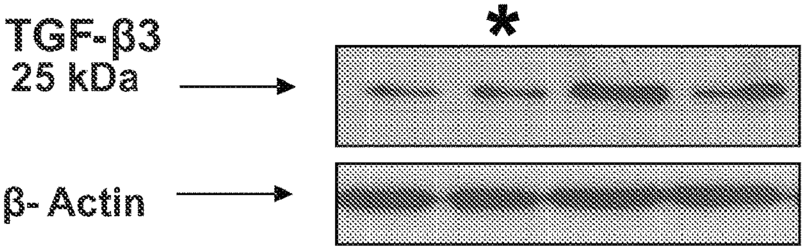
Figure 23D:
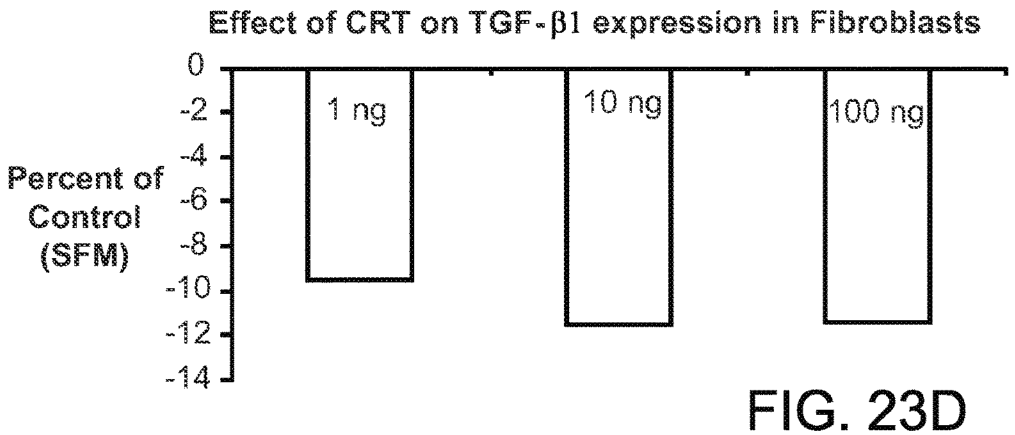
FIGS. 23D, 23E, 23F show graphs of the densitometric scanning of the intensity/quantity of the protein bands normalized to β-actin from the immunoblots shown in FIGS. 23A-23C.
Figure 23E:
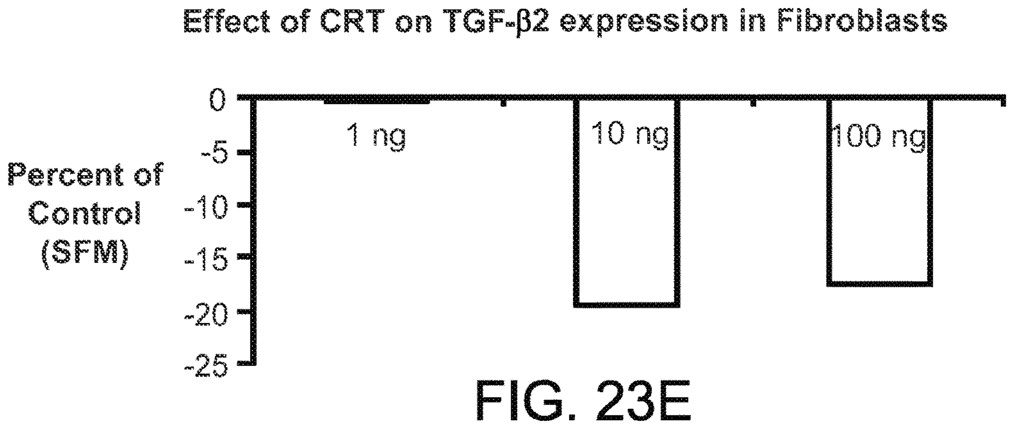
Figure 23F:
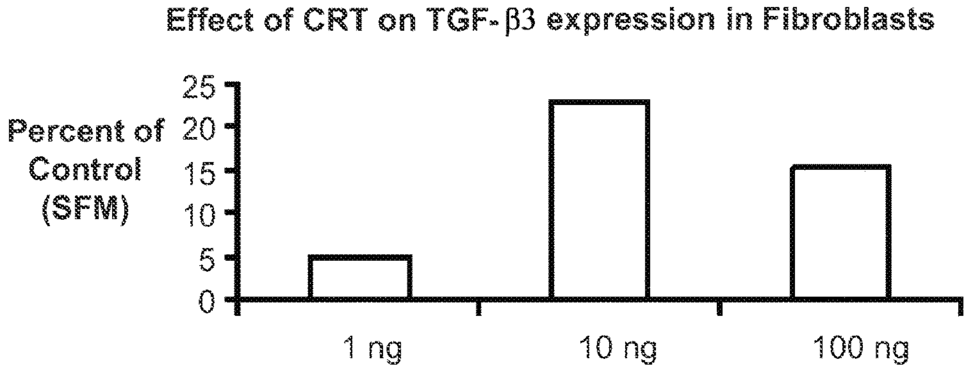

Example 14: Calreticulin Induced the Expression of TGF-β3 Isoform but, not TGF-β1 and TGF-β2 in Human Dermal Fibroblasts TGF-β isoforms are the master regulators of extracellular matrix formation and therefore, important to granulation tissue formation. Since the TGF-β3 isoform compared to TGF-β1 and TGF-β2, has specific positive effects on wound healing, as described in paragrpah 00138 and we show that topical application of calreticulin specifically increased TGF-β3 but not TGF-β1 nor TGF-β2 in the porcine wounds (Example 4, FIG. 5) and murine wounds (not shown), TGF-β isoform expression was analyzed in human fibroblasts in vitro. Human dermal fibroblasts were treated with increasing concentrations of calreticulin (mixture of human 5-CRT+ tag and 23-CRT+ tag) for 24 hours and the cell lysates prepared in RIPA buffer were analyzed by immunoblotting (as described above) using anti-peptide antibodies to the three individual TGF-β isoforms (TGF-β isoform antibodies were using at concentration of 2.0 μg/ml). The antibodies are described above. As was shown, in the neodermis of the calreticulin-treated porcine wounds (FIG. 5), predominantly in fibroblasts), TGF-β3 expression (FIG. 23C,F), but not TGF-β1 (FIG. 23A,D) nor TGF-β2 (FIG. 23B,E), was induced by calreticulin. The peak response of induction of TGF-β3 protein was at 10 ng/ml calreticulin. The increase in expression of TGF-β3 by fibroblasts in response to calreticulin suggests that calreticulin has anti-scarring effects (Ferguson, M. W. (2009) Lancet. 373:1264-1274).

The quantitative graphs below each Western blot represent the densitometric scan of the protein bands and reflect the levels of TGF-β isoforms normalized to β-actin or α-tubulin, as shown.

Figure 24A:
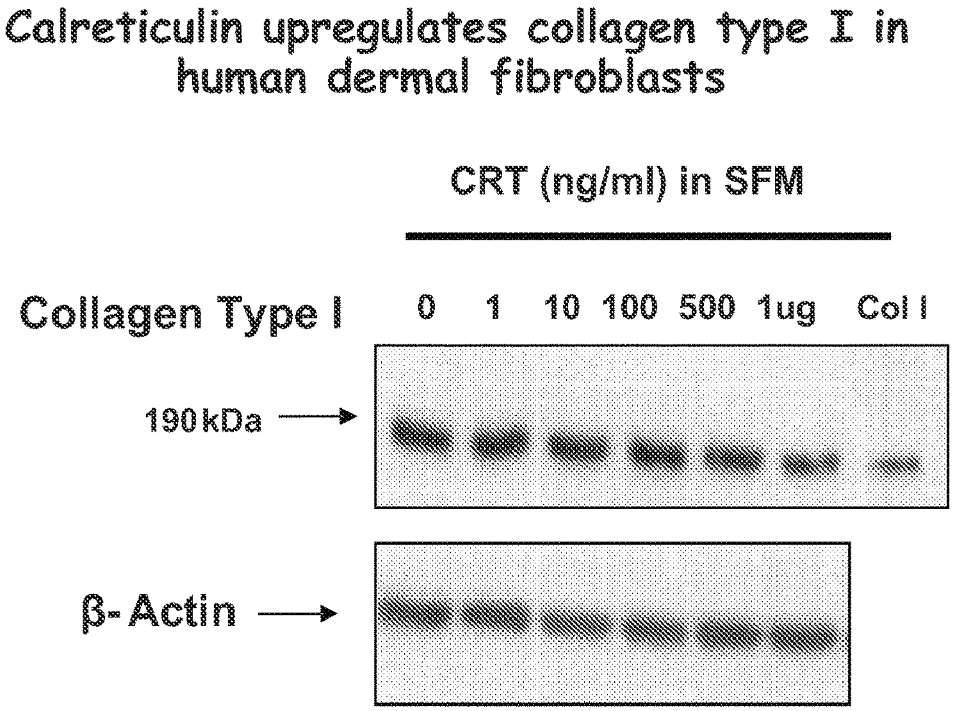
FIG. 24A shows an immunoblot of induction of collagen expression in human fibroblasts treated with increasing concentrations of calreticulin for 24 hours, lysed in RPIA buffer and subjected to immunoblot analysis using polyclonal antibodies to collagen type I. Collagen type I is control on the far right.
Figure 24B:
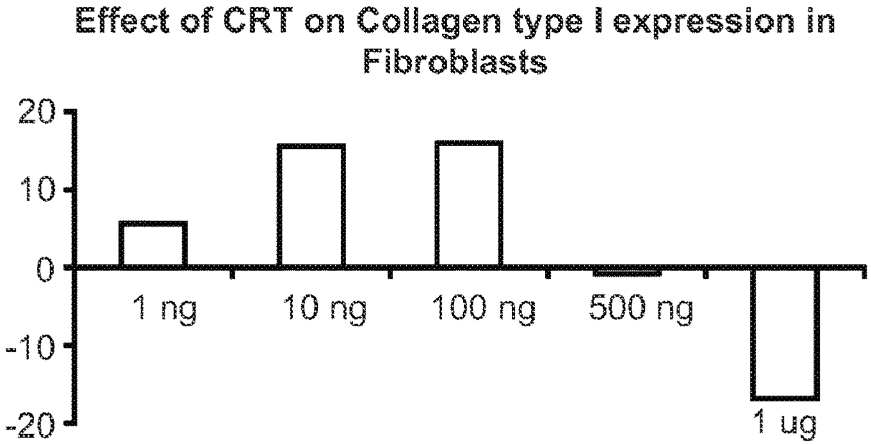
FIG. 24B shows a quantitative graph of the densitometric scanning of the intensity/quantity of the collagen protein band normalized to β-actin.

Example 15: Calreticulin Induced the Expression of Collagen Type I in Human Dermal Fibroblasts Collagen Type I is upregulated during normal wound healing and is important in providing a scaffold for cellular migration into the wound early in repair and remodeling of the neodermis later in the wound healing process. To determine whether calreticulin stimulated collage production in vitro as shown in vivo, human dermal fibroblasts, grown to 80-90% confluent, were treated with increasing concentrations of calreticulin (mixture of human 5-CRT+ tag and 23-CRT+ tag) in serum-free media for 24 hours and cell lysates prepared in RIPA buffer. Equal amounts of protein were loaded into the wells and the samples subjected to immunoblot analysis using an antibody to collagen type I. The intensity of each band on the blot was determined by densitometric scanning of the collagen and β-actin in each well to normalize expression to actin. Collagen type I expression is shown by the graph to the right. As shown by the immunoblot in FIG. 24A, calreticulin induces collagen type I expression in fibroblasts with a peak response (10-100 ng/ml) similar to calreticulin induction of migration. FIG. 24B shows a quantitative graph of the blot and represents the densitometric scan of the collagen type I protein band normalized to β-actin. Induction of collagen by calreticulin might be both direct and indirect through the induction of TGF-β3 expression.

Figure 25:
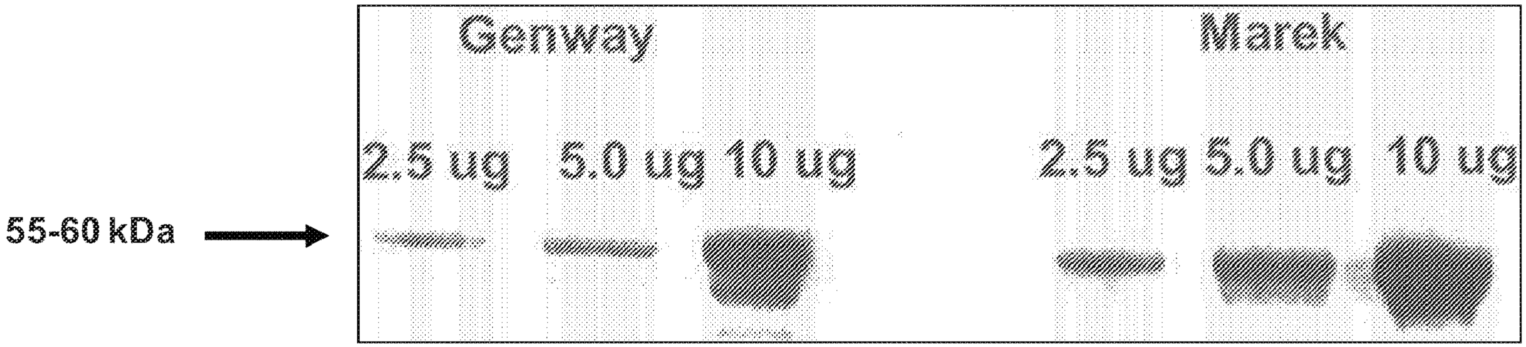
FIG. 25 is a SDS-PAGE (polyacrlyamide gel electrophoresis) that separates proteins by their molecular weight size. The gel shows that the product, human recombinant calreticulin (CRT) from GenWay Biotech (San Diego, Calif.) and rabbit recombinant CRT from M. Michalak (University of Alberta, Canada), migrates at the same molecular weight of approximately 55-60 KDa. Both sources of calreticulin are pure. The calreticulin from both sources are histadine (his)-tagged at their amino (N)-terminus for ease of isolation by affinity chromatography on a nickel-Sepharose resin Immedidately carboxy (C)-terminal to the his tag, GenWay calreticulin has two extra amino acids (Glu, Phe) and Michalak calreticulin has five amino acids (Thr, Met, Glu, Leu, Glu) prior to the N-terminal calreticulin amino acid sequences (5-CRT). The GenWay human calreticulin gene is inserted into the plasmid pTCA115 and expressed with the 17 amino acid signal peptide at the N-terminus. The rabbit and human calreticulin from the Michalak laboratory was inserted into the pBAD plasmid and expressed in an *E. coli* host.
Figure 26:
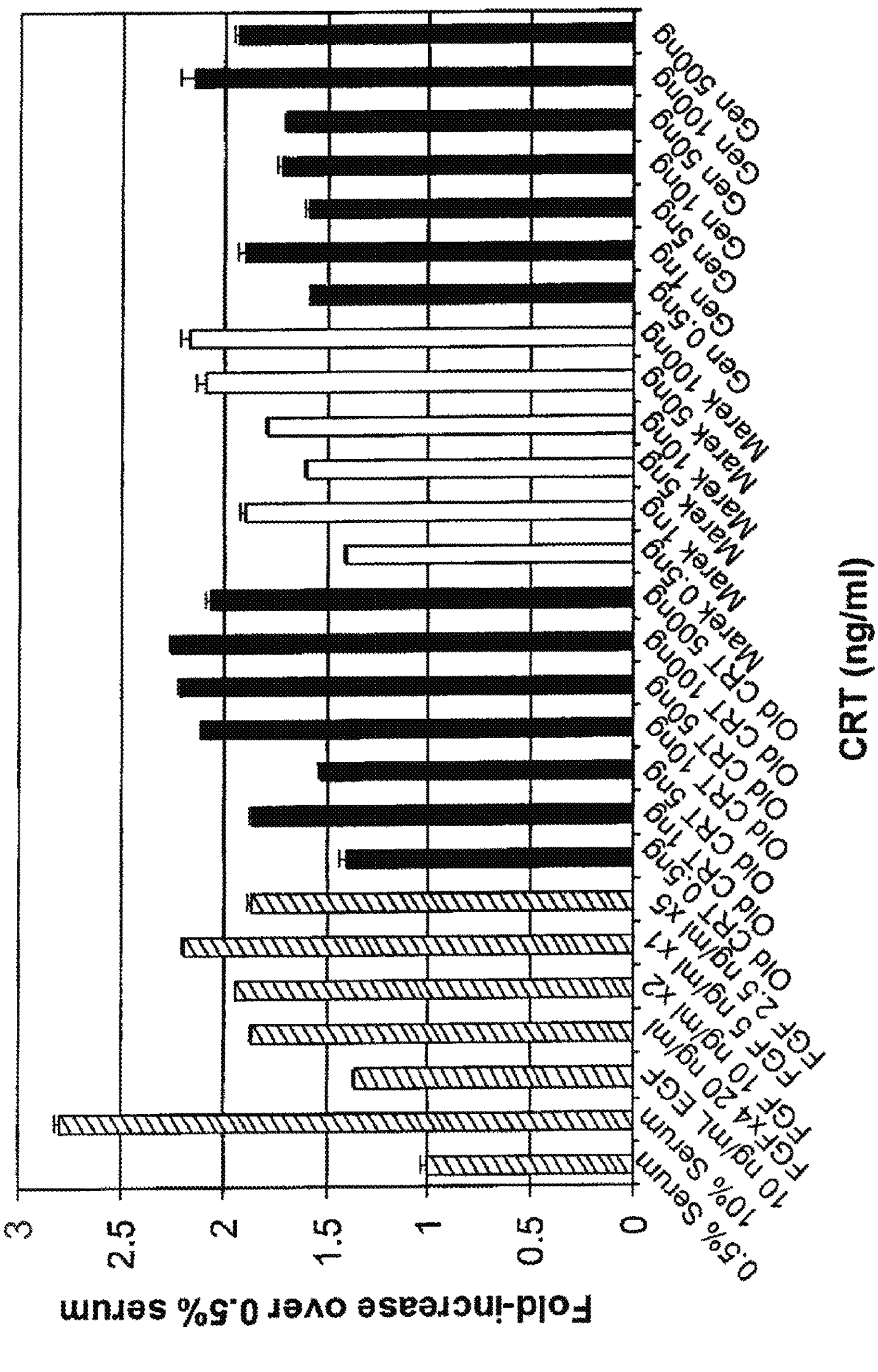
FIG. 26 is a bar graph showing that various calreticulin molecules stimulate the proliferation of human primary keratinocytes in a MTS proliferation assay.

Example 16: Various Calreticulin Molecules Stimulate Cellular Proliferation of Human Keratinocytes, Fibroblasts, and Microvascular Endothelial Cells The effect of calreticulin, derived from different sources, on proliferation of primary human dermal fibroblasts was tested in vitro. In FIG. 25, an SDS-PAGE shows that commercially available human recombinant calreticulin (his-tagged with two amino acids at the N-terminus preceding the calreticulin signal sequence; GenWay Biotech) and rabbit recombinant calreticulin from Marek Michalak, University of Alberta (his-tagged and containing a mixture of 5-CRT and 23-CRT) migrate with the identical expected molecular weight [m.w.=55-60 kDa] and relative migration and show similar purity (one band on the gel). Increasing concentrations of the calreticulins were applied to the gel (2.5, 5.0, 10 μgs) to try to resolve calreticulin fragments or impurities. As shown, a single band of protein was obtained with the higher concentration. These sources of calreticulin were employed in a proliferation assay. In addition, the stability of the biological activity of recombinant rabbit calreticulin (Michalak) at 4 C for 1.5 years was tested. The human fibroblasts were plated in 96-well tissue culture plates at $2.0\times10^3$ per well (the assay is described in Example 6 and Materials and Methods). At 70% confluency, the cells were synchronized for 24 hours in 0.5% fetal bovine serum in MEM and subsequently, increasing concentrations of calreticulin were added to the subconfluent primary fibroblasts. After 72 hours the MTS Proliferation assay (CellTiter96®) was performed in triplicate. The positive controls of Epidermal Growth Factor (EGF) at 10 ng/ml and Fibroblast Growth Factor at increasing concentration of 2.5 ng/ml, 5 ng/ml, 10 ng/ml, and 20 ng/ml [to obtain a dose-response curve of the positive control to ensure the responsiveness of the cells] were used. The data shown in FIG. 26 are expressed as fold increase±SEM compared to cells treated with 0.5% serum (negative control). The results show that old (1.5 year old) mixture of recombinant rabbit 5-CRT+ tag ("Old CRT") and 23-CRT+ tag and new (1-3 month old) mixture of recombinant rabbit 5-CRT+ tag and 23-CRT+ tag ("Marek") (both from Michalak), and GenWay CRT have similar biological activity in the stimulation of dermal fibroblasts. Thus, rabbit and human calreticulin have the same activity, and calreticulin is stable for a minimum of 1.5 years. The peak activity was between 10-100 ng/ml.

Example 17: Native/Natural Calreticulin (NAT-CRT) and 23-CRT Both from Michalak Induces Proliferation of Human Dermal Fibroblasts In Vitro Human dermal fibroblasts were synchronized in MEM media containing 0.2% fetal bovine serum (FBS) for 24 hours and subsequently treated with increasing concentrations of native calreticulin isolated from dog pancreas (NAT-CRT; obtained from Michalak) or calreticulin with 23 amino acids of the gene III periplasmic targeting sequence (pBAD/*E. coli* expression system) extended from the N-terminus of calreticulin (23-CRT; [not his-tagged] Michalak) in MEM media containing 0.2% serum. After 48 hours, proliferation was determined by the MTS assay (see Example 6). FIG. 27 shows that both NAT-CRT and 23-CRT stimulate proliferation; a triphasic response was obtained. This type of response represents the concentration-dependent gradient effects within the local wound environment. It was notable that both NAT-CRT and Michalak 23-CRT yield more than a 2-fold induction of proliferation at the peak concentrations shown. Although stimulation of cell proliferation by calreticulin was previously described (Nanney et al., Am J Pathol. 2008; 173:610-630), the calreticulin stimulatory effect was not known to occur at doses as low as shown in the instant experiments. However, as previously shown, calreticulin stimulates proliferation at ng quantities. Recombinant forms of CRT and natural CRT have the same specific biological activity in the stimulation of proliferation of fibroblasts.

Example 18: Native/Natural Calreticulin (NAT-CRT) and 23-CRT from Michalak Induce Proliferation of Mouse Embro Fibroblasts In Vitro Mouse embro fibroblasts (MEFs [K41 cells] obtained Marek Michalak, University of Alberta) were assayed for the ability of calreticulin to stimulate proliferation. The MEFs were treated exactly as described above and according to the method described in Example 6 and Materials and Methods. The MEFs were synchronized in MEM media containing 0.2% fetal bovine serum (FBS), treated with NAT-CRT or 23-CRT (Michalak) in MEM containing 0.2% serum, and analyzed for proliferation. FIG. 28 shows that, similar to the human fibroblasts (Example 17), both NAT-CRT and 23-CRT (Michalak) stimulated MEF proliferation with a triphasic response. This type of response represents the concentration-dependent gradient effects in the local wound environment. It was notable that both NAT-CRT and Michalak 23-CRT yielded more than a 1.8-2-fold induction of proliferation at the peak concentrations shown. The MEFs may have been more sensitive to the 23-CRT than the NAT-CRT because a greater response was achieved with the former at 500 pg/ml and 1 ng/ml.

Example 19: The C-Domain of Calreticulin Stimulates Proliferation of Human Dermal Fibroblasts These experiments were performed to designate which domain of calreticulin (N,P,C domain) exerts the function of stimulating proliferation. The domain structure of calreticulin is shown in FIG. 36 and FIG. 37. Human dermal fibroblasts were synchronized in serum-free MEM media for 24 hours and subsequently, treated with increasing concentrations of recombinant human calreticulin (SEQ ID NO:3) (GenWay Biotech, Inc., San Diego Calif.) or the C-domain of recombinant rabbit calreticulin (residues 285-400 [115 amino acids). The C-domain of calretculin of rabbit CRT (SEQ ID NO:7) is a GST-fusion protein produced in *E. coli* and obtained from Marek Michalak. After 24 hours, proliferation was determined by the MTS assay (described in Example 6 and Materials and Methods). The results were measured as percent growth stimulation over the untreated control. FIG. 29 shows that the C-domain of calreticulin contains the structure that dictates the function of stimulating cell proliferation. The data show that the C-domain of calreticulin may have higher specific activity than the entire molecule since it induces proliferation at a lower concentration (peak responses: 50 ng/ml versus 1.0 ng/ml) and stimulates a more robust response.

Example 20: Human Recombinant Calreticulin from GenWay (GenWay CRT) and the Michalak Lab (Mixture of 5-CRT+ Tag and 23-CRT+ Tag from Michalak) Stimulate Cellular Migration of Human Dermal Fibroblasts with Similar Peaks of Activity-Scratch Plate Assay The purpose of this experiment was to compare the biological activities in inducing migration of human dermal fibroblasts between recombinant human calreticulin purchased from GenWay Biotech (containing a 2 amino acid extension at the N-terminus) (SEQ ID NO:3) (GenWay CRT) and recombinant human calreticulin from the Michalak lab-University of Alberta Canada (containing a mixture of the five amino acid (5-CRT) (SEQ ID NO:4) and twenty-three amino acid (23-CRT) (SEQ ID NO:5) extension at the N-terminus of calreticulin+ tags) using the scratch plate assay. The scratch plate assay is the in vitro standard for wound healing. The cells migrate to cover a scratch made on the plate. The method is described in Example 7 and Materials and Methods. Briefly, the cells are grown to 80% confluency and the cells were scratched off to make a wound by drawing a line down the center of the well with a pipette tip. This assay for cell migration was performed under serum-free conditions for 24 h. Fetal bovine serum (containing many growth factors and proteins that induce migration) was a positive control and serum-free media (SFM) was a negative [untreated] control. FIG. 30 shows that both the recombinant human calreticulins from GenWay (Gen- Way-CRT) and Michalak (a mixture of 5-CRT+ tag and 23-CRT+ tag) resulted in similar induction of migration of HDFs. The data are expressed as percent healed (wound closure). The human CRT from Marek Michalak and GenWay appear to induce a peak of 40% wound closure at 0.1-1.0 ng/ml compared to the SFM control of 25.5% (approximately 2-fold).

Example 21: Natural Calreticulin Isolated from Dog Pancreas (NAT-CRT) and Calreticulin with a 23 Amino Acid Extension (23-CRT [not His-Tagged]) Induce Migration of Human Dermal Fibroblast with Similar Peaks of Activity Using an In Vitro Assay of Wound Closure-Scratch Plate Assay The fibroblasts were treated exactly as described above and in Example 7 and Materials and Methods. After 20 h, the percent wound closure (cell migration) was determined as described in Example 7. The positive control was 5% fetal bovine serum and serum-free media (SFM) served as a negative [untreated] control. The 24-well plates used for this assay contained separate negative and positive controls, each for 23-CRT (SEQ ID NO:9) and NAT-CRT (SEQ ID NO:6) [on separate plates]. FIG. 31 shows that compared to SFM, which induced 46-52% wound closure by the fibroblasts, both NAT-CRT and 23-CRT induced a similar peak response of 74% wound closure at 10 ng/ml. It is notable that induction of wound closure by both NAT-CRT and 23-CRT was to a similar extent as the positive control between 69-83%. Therefore, purified natural calreticulin isolated from dog pancreas (NAT-CRT) and recombinant calreticulin (23-CRT) behave similarly in the induction of migration of human fibroblasts using the scratch plate assay.

Example 22: Calreticulin Induces Migration of Human Mesenchymal Stem Cells (Fibrocytes) in the Scratch Plate In Vitro Wound Healing Assay Bone-marrow derived mesenchymal stem cells, termed fibrocytes, which have the cell surface markers (CD34+/ColI+), have been shown to migrate to sites of cutaneous wound injury and are important in wound healing. These cells proliferate and produce extracellular matrix proteins such as collagen to fill in the wound defect [among other functions]. Having shown that recombinant human calreticulin mediates the migration of keratinocytes, fibroblasts, monocytes, and macrophages using the scratch plate assay and migration chambers (see Nanney et al., Am J Pathol. 2008; 173:610-630), human recombinant calreticulin from GenWay Biotech (SEQ ID NO:3) (GenWay-CRT) was used to determine whether human mesenchymal stem cells (MSCs) could similarly be induced to migrate in response to increasing concentrations of GenWay-CRT using the scratch plate assay as an in vitro wound healing assay. The experiments were performed according to the methods described in Example 7 and Materials and Methods. The negative control was serum-free media (sfm) and the positive control was fetal bovine serum (FBS) at 0.1% and 2%. FIG. 32 shows that calreticulin induced migration of (hMSCs) above the sfm control. A biphasic response was obtained with peaks at 250 pg/ml and 5 ng/ml. This represents the physiological concentration-dependent effects of the local wound environment. The results indicate that calreticulin, exemplified by human calreticulin from GenWay (GenWay-CRT) likely recruits stem cells from the bone marrow to aid in wound healing (cell proliferation and extracellular matrix induction).

Example 23: Calreticulin-Treated Wounds Increase Collagen Deposition in Wounds in a Dose-Dependent Fashion Compared to Buffer-Treated Wounds Slides containing mouse tissue from wounds at 4 days and 10 days after injury, shown in FIG. 34, were stained with picrosirius red (Noorlander et al (2002) and examined by bright (left panels) and polarized light (right panels) to determine collagen content and organization. A dose-dependent increase in collagen induction was observed in the calreticulin-treated wounds. The yellow-green birefringence of the collagen fibrils in the wound bed suggested that the calreticulin-treated wounds (lower right panel) contained a more well organized and less cross-linked collagen matrix compared to a red-yellow pattern in the buffer (upper left panel/polarized light) and VEGF treated-wounds (not shown), which is consistent with higher cross-linking and potential scar formation. It is notable both, by light microscopy (FIG. 34, left panel) and by polarized light (right panel) that the calreticulin-treated wounds had increased neodermal depth consisting of granulation tissue at 10 days post-injury. (n.b., a greater area of granulation tissue induction was shown in the 5 mg/ml calreticulin-treated wounds than all other wounds). The dotted white line in the lower right panel of FIG. 34 illustrates the depth of collagen organization in the wound bed. Collagen organization was evident on day 4 after wounding as well (not shown). The increase in collagen organization is consistent with the increased expression of TGF-β3 observed in vivo in the calreticulin-treated porcine and murine wounds shown in FIG. 5 and in human fibroblasts treated with calreticulin in vitro, as shown by the Western Blot in FIG. 23 C. TGF-beta3 is known for its antiscarring effects and is being tested clinically to prevent scar formation after injury (Ferguson, M. W. (2009) Lancet. 373:1264-1274). Therefore, both the induction of expression of TGF-beta3 and the increased collagen organization in the mouse and porcine wounds treated with calreticulin indicates that calreticulin may have an anti-scarring effect on wounds. As noted in early studies, the striking dose-response to calreticulin treatment is apparent in the tissue treated with the 0.5% (5 mg/ml) calreticulin (FIG. 34, lower right panel) versus the 0.1% (1.0 mg/ml) calreticulin (FIG. 34, lower left panel showing tissue under polarized light). Both of these doses led to increased collagen stimulation over the buffer treated control, but the 0.5% dose also stimulated more production than the positive control of VEGF. The mouse wounding experiments are described in the Materials and Methods above.

Example 24: Calreticulin Enhances the Uptake of Heat Killed Staph Aureus by Human Polymorphonucleated Neutrophils Heat killed Staph Aureus at $2\times10^8$/ml were incubated with human peripheral blood neutrophils for 2 hours. The percent of neutrophils containing bacteria were determined compared to an untreated control. FIG. 38 demonstrates that calreticulin enhanced the uptake of bacteria by the neutrophils by 18%. These results suggest that calreticulin may have bactericidal effects. Since a major deterrent to acute and chronic wound healing is bacterial infection, this function of calreticulin may contribute to its overarching effect on wound repair.

Example 25: Use of Calreticulin (CRT) to Treat Skin Ulcers of Sickle Cell Disease Patients Sickle Cell Disease (SCD) is considered a rare and neglected disease and serious unmet medical need as to date, there is no agent that can successfully treat the impaired and delayed healing associated with this disease. SCD is a genetic disease caused by a single amino acid substitution in the hemoglobin gene (S hemoglobin). The pathology is characterized by hemoglobin polymerization, red blood cell rigidity that decreases microvascular blood flow leading to tissue ischemia and infarction. In addition, other pathologies of the vasculature are abnormal vascular tone, activated adhesive endothelium (lining of the blood vessels), and vasculitis. Among other pathologies such as pulmonary hypertension, this vascular occlusive disease causes very painful chronic leg ulcerations in 30% of patients globally. The ulcers usually occur on the medial and lateral malleoli and occur with no previous trauma. Less than 5% of SCU patients have complete wound closure. The chronic ulcers can last from 6 months to many years with repeated closures and re-opening. Mechanical obstruction resulting from the aggregated sickle cells, venous pathologies described above including vasoconstriction, bacterial infections, thrombosis, anemia with a decrease in oxygen capacity and decreased nitric oxide lead to endothelial malfunction. Decreased Nitric Oxide stimulates endogenous calreticulin synthesis (Gold et al., FASEB J., 2010, 24:665-683). However, atrio-venous shunting is considered to be a major contributing factor to the pathogenesis of ankle ulcerations in SCD patients (Minniti et al., 2010, Amer J of Hematol., 85:831-833).

Epidermolysis bullosa (EB) is a genetic connective tissue disease that causes skin blistering with an incidence of 1/50,000. Children suffer from this rare and neglected orphan disease. Mechanical friction or trauma separates layers of skin forming blisters or chronic wounds that do not heal.

Since, as demonstrated herein, calreticulin has wide-ranging diverse effects on the most important aspects of wound healing namely, stimulation of proliferation and migration of most wound cells and induction of matrix constituents composing granulation tissue thereby causing accelerated wound resurfacing, maturity and tissue remodeling, this protein is best suited to heal the most difficult chronic wounds characterized by delayed healing such as those of Sickle Cell Disease (SCD) and epidermolysis bullosa (EB). Calreticulin is unique in its wound healing capacity as other wound healing agents do not possess the same array of mechanisms of action in healing wounds.

40 patients with SCD having SCUs (sickle cell ulcers) are enrolled in the clinical study. These patients are treated with CRT (5 mg/ml; possible alternative concentrations are in the range from 2.5 mg/ml to 100 mg/ml) for 4 weeks and their SCUs are compared to SCUs before the start of the treatment. Calreticulin administration will be at 5 mg/ml but can be administered from 2.5 mg/ml to 100 mg/ml. Patient assessment is conducted for 3 months before the treatment, on the day of the first treatment and then weekly during treatment followed by assessments at 4 weeks, 3 months and 6 months after the completion the treatment.

The following parameters are assessed:

SCU healing rate (measured by % wound closure over time: the remaining wound opening is traced onto paper, the image scanned and the area of opening quantified by Image J or any other imaging program).

Increase in granulation tissue (measured by visual appearance).

Decrease in pain associated with SCU (subjective assessment by patients using a scale of 1-10).

Improved quality of life (subjective assessment by patients according to a questionnaire that specifically addresses quality of life issues).

Incidence of SCU infection, cellulitis, osteomyelitis, amputations, sepsis, hospitalizations, and death.

Example 26: Use of Calreticulin (CRT) to Treat Wrinkles 40 female subjects aged 45-55 years old are enrolled in the study. For each subject, forehead wrinkles are divided into three separate areas to which the following three compositions are injected once daily for 60 days: (1) buffer (control), (2) buffer+calreticulin, (3) buffer+calreticulin+hyaluronic acid.

Both subjective scoring by subjects themselves and objective scoring of wrinkle appearance is performed on the first day of the study, once a week during the administration and in three months and in six months following the end of administration. Objective scoring is performed using the CANFIELD™ clinical photography platform. Objective scoring is performed by non-biased observers who rate the pictures on a graded scale (0-12) based on the presence of lines and wrinkles. This rating is performed blinded, or without knowledge as to whether the picture is of calreticulin-treated or control skin. Subjective scoring is performed by the patients themselves, on a graded scale (0-12). Average scores for treated (groups 2 and 3) or untreated (control, group 1) skin as well as percent change are determined.

Fibroblast senescence assay. Fibroblasts are divided into two groups. Group 1 is treated with UVB light to cause damage to the cells analogous to skin aging (damage to cells from the sun exposure). Group 2 (control) does not receive UVB treatment. Each group is further subdivided into three subgroups, of which the first one is treated with calreticulin, the second one (negative control) receives only PBS, and the third one (positive control) is treated with 0.005% Trolox. Senescence from the UVB is measured by fixing the cells and staining with potassium ferricyanide, potassium ferrocyanide and X-gal solution in DMSO.

Example 27: Use of Calreticulin (CRT) to Treat Corneal Abrasions

Bilateral 6 mm diameter corneal epithelial abrasions are made in each of six rabbits. A calreticulin-containing formulation is applied topically four times per day in right eye of each rabbit for one week, and buffer alone is placed in left (control) eye of each rabbit. The wound size is determined by staining with 1% fluorescein and photographed at the slit lamp with a digital camera at 0, 1, 2, 3 days postoperatively. Rabbit corneas are collected for histological examination on day 7. Time to complete closure of corneal wound and thickness of the central corneal epithelium as well as epithelial and stromal organization is measured.

CONCLUSION

The present inventors have discovered that topical application of calreticulin to partial and full thickness excisional porcine wounds positively affects both epidermal and dermal aspects of cutaneous wound repair. Surprisingly, the calreticulin-treated wounds showed an increase in the rate of re-epithelialization and a greater degree of stratification of the epidermal layer and amount of granulation tissue, reaching wound maturity earlier than PDFG-BB-treated (Regranex®) wounds, used as positive control. Similar positive effects were observed in the dermis of the calreticulin-treated wounds of steroid-challenged pigs, indicating that calreticulin is an important new factor that may be used to promote healing of both acute wounds with deep and/or extensive tissue injury and chronic wounds, such as chronic diabetic wounds/ulcers, venous- and arterial-statsis wounds/ulcers, and pressure ulcers (bed sores). Furthermore, in the calreticulin-treated wounds, TGF-β3, an important protein in driving matrix formation and inducing cellular migration, including the influx of macrophages into the wounds, and also known for prevention of post-injury scarring (due to its ability to induce collagen organization) was markedly increased in the dermis. In addition, the calreticulin-treated wounds showed a comparatively remarkable increase in proliferating basal keratinocytes and cells of the neodermis (e.g., fibroblasts).

In the murine diabetic mouse model (leptin receptor null mice) of excisional wound repair, calreticulin treated wounds closed significantly faster than the buffer treated controls and resulted in increased granulation tissue formation. The ability of calreticulin to induce granulation tissue within 3 days of wounding supports a role for this protein in tissue remodeling of deep tissue wounds (e.g., wounds sustained by military in combat). The epithelial gap was significantly smaller in calreticulin treated wounds than buffer treated controls. Calreticulin treated wounds also exhibited increased proliferation of basal keratinocytes and fibroblasts. Calreticulin induced a decrease in time to closure of the diabetic wounds, which was statistically significant from day 3 after injury until final closure (day 17 vs. 21; $p<0.05$). There was a remarkable appearance of dermal appendages including hair follicles at day 28 that were lacking in the untreated controls. This finding is significant since the excisional wound extended through the murine dermis into the panniculus carnosus (muscle layer beneath the dermis in the mouse). Epithelial gap was reduced at days 7 and 10 ($p\leq0.05$) and granulation tissue was markedly increased at day 7 ($p\leq0.0006$). Histologically, the calreticulin-treated wounds appeared highly cellular with increased Ki67 and BrDU positive proliferating basal keratinocytes and fibroblasts ($p\leq0.05$). By picrosirius red staining, increased collagen organization was observed in the calreticulin treated porcine and murine wounds. Therefore, calreticulin should have anti-scarring effects. The quality of collagen cross-linking is also shown by calreticulin's ability to increase wound tensile strength in a rat model. Notably, the dose of calreticulin for optimal wound healing was identical in both the porcine and murine wound healing models (5.0 mg/ml in saline). Moreover, the histology of the wounds treated with calreticulin was remarkably similar in both animal models; this histology shows particular characteristics in calreticulin-treated wounds. Calreticulin targets many more aspects of wound repair than PDGF-BB (Regranex®). Of most significance it has strong effects on the epidermis (keratinocytges) whereas Regranex® only affects the dermis and does not prevent scarring. Calreticulin should be able to heal wounds with large areas of epidermal denudation since it induces wound resurfacing and early epidermal stratification (e.g., thermal and chemical burn wounds).

In vitro, calreticulin induced chemotaxis (concentration-dependent directed migration) of human fibroblasts, keratinocytes monocytes, and macrophages with maximal induction at 1-10 ng/ml, 10 pg/ml 1 ng/ml, and 5.0 ng/ml, respectively, which was greater than positive controls ($p<0.05$). Calreticulin induced alpha5 and beta1 integrin expression on keratincytes and fibroblasts; a function of cell surface expression of integrins is for cell migration [into the wounds from adjacent normal tissue]. In addition, calreticulin maximally stimulated proliferation of keratinocytes (100 pg/ml) and fibroblasts (100 ng/ml) by 2.2-fold and 2.4-fold, respectively over the untreated controls. In vitro, calreticulin dose-dependently induced fibronectin protein by keratinocytes and fibroblasts and collagen, TGF-β3, and alpha smooth muscle actin, in fibroblasts. These proteins are the most important constituents of granulation tissue necessary for wound remodeling and to provide a matrix for keratinocyte migration over the wound for resurfacing. Alpha smooth muscle actin is important in wound contraction/closure. These functions also explain how calreticulin accelerates and improves the quality of wound repair demonstrated in the animal models of wound repair and supports its utility as a successful agent for the treatment of deep tissue wounds requiring granulation tissue/neodermis to fill in the wound defect. The stimulation of proliferation of keratinocytes and fibroblasts and the stimulation of migration of keratinocytes, monocytes, and macrophages by calreticulin has not been previously described and moreover, the identification of the amino acid sequence responsible for cellular proliferation (the C-domain of recombinant rabbit calreticulin, residues 285-400) also has not been previously described.

Importantly, calreticulin induced migration and proliferation of fibroblasts under high glucose conditions (simulating the diabetic milieu of hyperglycemia etc.) and migration of diabetic fibroblasts isolated from diabetic mouse skin, as well as stimulated migration of macrophages under high glucose conditions; these are serious defective processes contributing to the abnormal and retarded healing of diabetic wounds. Whereas the cells assayed under high glucose conditions exhibited decreased migration and proliferation compared to positive controls, calreticulin nonetheless restored their proliferative and migratory capacity. The responses obtained in vitro support the physiological mechanisms involved in calreticulin-induced enhanced wound closure, cellularity, and thus healing of the diabetic and other chronic wounds that demonstrate impaired wound healing. As diabetic wounds remain classified as a serious unmet medical need and are one of the most difficult wounds to heal with a history of being recalcitrant to any wound healing agent, calreticulin should be useful for the treatment of all acute extensive and deep tissue injuries caused by severe trauma, for burn wounds, and for all chronic wounds. Another type of wound is a leg skin ulcer that results from sickle cell disease, classified as a rare, genetic and neglected disease. No therapeutic agent has successfully allowed healing of these wounds. Therefore, wound ulcers of sickle cell disease remain classified as a serious unmet medical need. Because of the wound healing attributes of calreticulin are indicated for poor and delayed healing, this protein should be particularly useful for improving the poor/impaired healing and reducing the pain of chronic ulcers associated with sickle cell disease. Furthermore, since calreticulin induces collagen, fibronectin and TGF-β3, it should have utility for cosmetic use in the treatment of skin wrinkles and prevent cell senescence, bone and cartilage repair, and tissue remodeling and reconstruction, in general. Since calreticulin is not angiogenic, it is believed that it would be useful for the treatment of corneal abrasions, in which blood vessel growth causes loss of vision.

Further, N-terminal sequences added to the natural CRT sequence as a consequence of the recombinant process and histadine tags added to aid in purification do not interfere with the beneficial effects of CRT on chronic wound healing. This has been demonstrated in the Examples above, which tested (1) recombinant human calreticulin having an N-terminus with an added histadine tag and two additional amino acids (GenWay Biotech, Inc., San Diego Calif.) ("GenWay CRT"), (2) recombinant rabbit and human calreticulin having a histadine tag and five additional amino acids at the N-terminus of the natural rabbit and human CRT amino acid sequence (from M. Michalak, University of Alberta) ("Michalak CRT 5"), (3) recombinant rabbit and human calreticulin having a histadine tag and 23 additional amino acids at the N-terminus of the natural rabbit and human CRT amino acid sequence (from M. Michalak, University of Alberta) ("Michalak CRT 23"), (4) recombinant human calreticulin having five additional amino acids at the N-terminus of the natural human CRT sequence without a his tag, (5) recombinant human calreticulin having 23 additional amino acids at the N-terminus of the natural human CRT amino acid sequence without a his tag, and (6) natural dog pancreas calreticulin ("NAT-CRT").

In conclusion, calreticulin has the potential to be a powerful therapeutic for the treatment of both acute wounds with extensive tissue damage and chronic wounds through multiple biological effects. The effects demonstrated in vivo are substantiated by in vitro bioactivities showing that calreticulin stimulates proliferation, migration of, and the production of extracellular matrix proteins by, cells critical to both wound resurfacing and remodeling.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method of stimulating de novo regeneration of an epidermal appendage in a wound or skin of a patient in need thereof, which method comprises administering to the wound or skin of the patient a therapeutically effective amount of calreticulin or a functional fragment of calreticulin, or a fusion protein comprising calreticulin or a functional fragment of calreticulin, wherein said functional fragment is N-, P- or C-domain of calreticulin, wherein said epidermal appendage was not present or was removed in said wound site or skin prior to the calreticulin administration.

2. The method of claim 1, wherein the epidermal appendage is a pigmented hair follicle.

3. The method of claim 1, further comprising monitoring the regeneration of the epidermal appendage.

* * * * *

SEQUENCE LISTING

```
<160> NUMBER OF SEQ ID NOS: 9

<210> SEQ ID NO 1
<211> LENGTH: 455
<212> TYPE: PRT
<213> ORGANISM: Homo sapiens

<400> SEQUENCE: 1

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Leu Glu Glu Ser Lys His Lys Ser Asp Phe
        35                  40                  45

Gly Lys Phe Val Leu Ser Ser Gly Lys Phe Tyr Gly Asp Glu Glu Lys
    50                  55                  60

Asp Lys Gly Leu Gln Thr Ser Gln Asp Ala Arg Phe Tyr Ala Leu Ser
65                  70                  75                  80

Ala Ser Phe Glu Pro Phe Ser Asn Lys Gly Gln Thr Leu Val Val Gln
                85                  90                  95

Phe Thr Val Lys His Glu Gln Asn Ile Leu Glu Asp Cys Gly Gly Gly
            100                 105                 110

Tyr Val Lys Leu Phe Pro Asn Ser Leu Asp Gln Thr Asp Met His Gly
        115                 120                 125

Asp Ser Glu Tyr Asn Ile Leu Glu Met Phe Gly Pro Asp Ile Leu Glu
    130                 135                 140

Cys Gly Pro Gly Thr Lys Lys Val His Val Ile Leu Glu Phe Asn Tyr
145                 150                 155                 160

Lys Gly Lys Asn Val Leu Ile Leu Glu Asn Lys Asp Ile Leu Glu Arg
                165                 170                 175

Cys Lys Asp Asp Glu Phe Thr His Leu Tyr Thr Leu Ile Leu Glu Val
            180                 185                 190

Arg Pro Asp Asn Thr Tyr Glu Val Lys Ile Leu Glu Asp Asn Ser Gln
        195                 200                 205
```

-continued

```
Val Glu Ser Gly Ser Leu Glu Asp Asp Trp Asp Phe Leu Pro Pro Lys
    210                 215                 220

Lys Ile Leu Glu Lys Asp Pro Asp Ala Ser Lys Pro Glu Asp Trp Asp
225                 230                 235                 240

Glu Arg Ala Lys Ile Leu Glu Asp Asp Pro Thr Asp Ser Lys Pro Glu
                245                 250                 255

Asp Trp Asp Lys Pro Glu His Ile Leu Glu Pro Asp Pro Asp Ala Lys
            260                 265                 270

Lys Pro Glu Asp Trp Asp Glu Glu Met Asp Gly Glu Trp Glu Pro Pro
        275                 280                 285

Val Ile Leu Glu Gln Asn Pro Glu Tyr Lys Gly Glu Trp Lys Pro Arg
    290                 295                 300

Gln Ile Leu Glu Asp Asn Pro Asp Tyr Lys Gly Thr Trp Ile Leu Glu
305                 310                 315                 320

His Pro Glu Ile Leu Glu Asp Asn Pro Glu Tyr Ser Pro Asp Pro Ser
                325                 330                 335

Ile Leu Glu Tyr Ala Tyr Asp Asn Phe Gly Val Leu Gly Leu Asp Leu
            340                 345                 350

Trp Gln Val Lys Ser Gly Thr Ile Leu Glu Phe Asp Asn Phe Leu Ile
        355                 360                 365

Leu Glu Thr Asn Asp Glu Ala Tyr Ala Glu Glu Phe Gly Asn Glu Thr
    370                 375                 380

Trp Gly Val Thr Lys Ala Ala Glu Lys Gln Met Lys Asp Lys Gln Asp
385                 390                 395                 400

Glu Glu Gln Arg Leu Lys Glu Glu Glu Glu Asp Lys Lys Arg Lys Glu
                405                 410                 415

Glu Glu Glu Ala Glu Asp Lys Glu Asp Asp Glu Asp Lys Asp Glu Asp
            420                 425                 430

Glu Glu Asp Glu Glu Asp Lys Glu Glu Asp Glu Glu Glu Asp Val Pro
        435                 440                 445

Gly Gln Ala Lys Asp Glu Leu
    450                 455
```

<210> SEQ ID NO 2
<211> LENGTH: 5881
<212> TYPE: DNA
<213> ORGANISM: Homo sapiens

<400> SEQUENCE: 2

```
gtccgtactg cagagccgct gccggagggt cgttttaaag ggcccgcgcg ttgccgcccc      60

ctcggcccgc catgctgcta tccgtgccgc tgctgctcgg cctcctcggc ctggccgtcg     120

ccgagcctgc cgtctacttc aaggagcagt ttctggacgg aggtaacgcc tggtcccgcc     180

tcgaggccgc cccgacgacg cggccggccc ccgatcctgg atctgcgttg tcgcccgtaa     240

ttaccgttta gaggtccaac acggtggcct cccgggacta gagccgcggg cgatttctct     300

tctgcgtccc tggggagcgc ggagggcgta gcggcctccc gcggcgggag ttagggttag     360

cccgaggatc tctgaaggca cccgacgtgt caaactagag gttggaatgg ggagtgtcgg     420

ggatctcctt tcctgtcccc agcagcttgt ggctctcggc agatgtttgg tgtggggggg     480

gattagcaca gccgctctga cctacccctc taatccccca cttagacggg tggacttccc     540

gctggatcga atccaaacac aagtcagatt ttggcaaatt cgttctcagt tccggcaagt     600

tctacggtga cgaggagaaa gataaaggta agagcctagg agtgggtgct cagatccggg     660
```

-continued

```
aggacttcct ggcagaagtc cttgtctgta cacacacagc cgggacagtc cccttggagg    720
aggacaggtg gaggaagtgg gggagtcttc tctattctct aagtcgaggg tcctcgcgag    780
tcaaggccca acggtgacct cactaccgtc ccgtctcagg tttgcagaca agccaggatg    840
cacgctttta tgctctgtcg gccagtttcg agcctttcag caacaaaggc cagacgctgg    900
tggtgcagtt cacggtgaaa catgagcaga acatcgactg tgggggcggc tatgtgaagc    960
tgtttcctaa tagtttggac cagacagaca tgcacggaga ctcagaatac aacatcatgt   1020
ttggtgaggg cctgcttcct ggtgctgatc tctgtcccat tagttagagg gagacccaga   1080
ccccattgac tttcttaata atgatttttt ttggaagggg agctaaaaga ataagtccca   1140
gcaacaattt attgcattat gatcgcagat ctaggctgtt aatttaattt gcgtgtttgt   1200
atatagttat ttcccaatct tactaatgag gattttgagt tctagagcac tgattttttt   1260
tttttctcct ttaaacttaa ggctccaccc acagcccatt caggacagaa tcagggtctg   1320
agtttctctt ctcagccttg acagacccga gttgaagaac caggtcttcc ttttataaag   1380
aggggtgaga gcctcgagat gatgggtagt ctctgactct taactggatc tgcttcacac   1440
ctaggtcccg acatctgtgg ccctggcacc aagaaggttc atgtcatctt caactacaag   1500
ggcaagaacg tgctgatcaa caaggacatc cgttgcaagg tgtgcctggg ggtggtggca   1560
aatggctgtc atggggagat tcagaggtca gcctcattgg ggggtggccc ccgctcacct   1620
tcttccttct tcaggatgat gagtttacac acctgtacac actgattgtg cggccagaca   1680
acacctatga ggtgaagatt gacaacagcc aggtggagtc cggctccttg gaagacgatt   1740
gggacttcct gccacccaag aagataaagg atcctgatgc ttcaaaaccg gaagactggg   1800
atgagcgggc caagatcgat gatcccacag actccaagcc tgaggttggt gtttgggcag   1860
gggctctgct ctccacattg gagggtgtgg aagacatctg ggccaactct gatctcttca   1920
tctacccccc aggactggga caagcccgag catatccctg accctgatgc taagaagccc   1980
gaggactggg atgaagagat ggacggagag tgggaacccc cagtgattca gaaccctgag   2040
tacaaggtga gtttggggct ctgagcaggg ctggggctca cagtggggag tgcaccaacc   2100
ttactcaccc ttcggtttcc ttctcccttc tgcagggtga gtggaagccc cggcagatcg   2160
acaacccaga ttacaagggc acttggatcc acccagaaat tgacaacccc gagtattctc   2220
ccgatcccag tatctatgcc tatgataact ttggcgtgct gggcctggac ctctggcagg   2280
tgagacttgg aggaaaaagg aggatccctg gggtacctca agtgcataag atcacccaag   2340
aggaaaggga cagggtaggc accccaggtg agtctgactc aaaaatggta cttcttgtaa   2400
acagtacttc ctggtctgtc cctgtgaagt cctcacagca accccttttaa ggttatactt   2460
gctgtgcacc aagtacttcc ccaagtactt ttatgcaaat caacttcttt acccccaaag   2520
acctagaagg tggtcaggta acccagttag ttagctgggg ctgggcacag tggctcaccc   2580
ttacaatcac ggtactttgg gaggctgaga cagaggattg cttgaggcca ggagttacac   2640
aactcaacct agcttggcaa cacagcgagg agaccctatc tctacaaaaa aaattttttt   2700
ttttgagaca gagtttcact cttgttgctg aggctggagt gcaatggcac gatctcagct   2760
cactgcgccc tccgtctcct ggtttcaagc gattctcctg cctcagcctc cggagtagct   2820
gggattacag gcatgtgcta ctatggatgc caggctaatt tttttttttt tttttttttt   2880
tgagaccgtg ccttgctctg tcgcccaggc tggagtgcag tggtgtgatc tctgctcact   2940
gcaagctccg cacgaccccc caggttcact ccattcttct gcctcagggt cccgagtaac   3000
tgggactaca ggcacccccc accatgcctg gctaattttt ttgtattttt ttttttagta   3060
```

-continued

```
cagacatggt ttcaccgtgt tagccaggat ggtctccatc tcctgacctc atgaaccacc   3120

caccttggcc tcccaaagtg ctgggattac aggcgtgagc cacctcaccc agccttttg   3180

tagagacagg gcttcatgtt gcccaggttg gtctcgaact cctggcctca ggtcatctgc   3240

ccgcctcggc ctcccaaagt gctgggatta caagggttag ccaccatgcc tagcctctac   3300

aaaaacttta aaaattggcg agatgtcatg catacctgta gtcccaacta ccaaggaaga   3360

aggatgatca cttgagcctg gggcatcgag gctgcagtga gccatgatta tgtcactgca   3420

ctccagcctc ggtgacagag tgagaccctc tcaaaaaaag ttgggacttg gccggacaca   3480

gtggctcaca cctgtaatcc cagcactttg ggaggccaag gcgggtggat cacaaggtca   3540

ggagatggag accatcctgg ctaacatggt gaatgaaacc ccatctctag taaaaataca   3600

aaaaatttgc caggtgtggt ggtgggcgcc tgtagtccca gctactcggg aggctgaggc   3660

aaaaggatga cgtgaacccg ggaggcggag cttgcagtga gctgagatca tgccattgca   3720

ctccagcctg ggtgatagcg agactctgtc ccaaaaaaaa aaaaaaatgc tgggactgaa   3780

tttttgtctg ttttggtcac tgaaatacct tctgtgccca agacagttct ggcatgtagt   3840

aggtacctga aaaatacctg aataagagag tgagaaacaa gaaacaggtg cagagaactg   3900

aagtcagtgg cccaaggtca tgggggtagg aaaccacaaa gctggggttt gaacctgggc   3960

agtacagcac ctgagtctct ccatcttttt tttttttttt ttttaagaca gagtcttgct   4020

ctgtcaccca ggttggagtg cagtggcttg atctcggctc actgcagcct ctgccttcca   4080

ggttcaagtg attctcatgc ctcatcctct cgagcagctg gaattacagg catgcgccac   4140

gacgctgggc tttttttttt ttgagatgga atttcactct tgttgcccag gctggagtgc   4200

aatgatgcaa tctcggcggc tcaccacaac ctctgcatcc cagattcaag cgattctcct   4260

gcctcggcct cctgagtagc tgggattaca gggatgcgcc atcacagacc ccgggctaat   4320

tttttttagt agagacagag tttcactatg ttgcccaggt tggtctcgaa ctcctggcct   4380

caagtgatcc gttcgccatg acctcccaaa gtgctgggat tacaggcatg agcccgtccc   4440

gtccctggct gtctctccat ctttccatct tttttttttt tttttttttt tttggagatg   4500

gagtctcact ctgtcaccca ggctggagtg cagtggcacg atcttggctc actgcaagct   4560

ccgcctcctg ggttcacatc attctcctgt ctcagcctcc caaatagctg ggactacagg   4620

cacttgccac cacgcctggc tgatttttttg tatttttagt agagacgggg tttcaccgtg   4680

ttagccaggg tggtctcgat ctcctgacct cgtgatccgc ccaccttggc ctctgggcga   4740

ggattacagg cgtgatccac ctcacctggc ctctccatct ttttaactgc agtgtcagcg   4800

gtgttccttg tcttctctgc agatgcaggc agcagaatat agtggttata ggaacacagg   4860

tggaaaccct gtccaaagca agggctatcg ggtatcacct ctgaccatcc ttcccattca   4920

tcctccaggt caagtctggc accatctttg acaacttcct catcaccaac gatgaggcat   4980

acgctgagga gtttggcaac gagacgtggg gcgtaacaaa ggtgaggcct ggtcctggtc   5040

ctgatgtcgg gggcgggcag ggctggcagg gggcaaggcc ctgaggtgtg tgctctgcct   5100

gcaggcagca gagaaacaaa tgaaggacaa acaggacgag gagcagaggc ttaaggagga   5160

ggaagaagac aagaaacgca aagaggagga ggaggcagag gacaaggagg atgatgagga   5220

caaagatgag gatgaggagg atgaggagga caaggaggaa gatgaggagg aagatgtccc   5280

cggccaggcc aaggacgagc tgtagagagg cctgcctcca gggctggact gaggcctgag   5340

cgctcctgcc gcagagctgg ccgcgccaaa taatgtctct gtgagactcg agaactttca   5400
```

-continued tttttttcca ggctggttcg gatttggggt ggattttggt tttgttcccc tcctccactc 5460
tcccccaccc cctccccgcc cttttttttt ttttttttta aactggtatt ttatctttga 5520
ttctccttca gccctcaccc ctggttctca tctttcttga tcaacatctt ttcttgcctc 5580
tgtccccttc tctcatctct tagctcccct ccaacctggg gggcagtggt gtggagaagc 5640
cacaggcctg agatttcatc tgctctcctt cctggagccc agaggagggc agcagaaggg 5700
ggtggtgtct ccaacccccc agcactgagg aagaacgggg ctcttctcat ttcacccctc 5760
cctttctccc ctgcccccag gactgggcca cttctgggtg gggcagtggg tcccagattg 5820
gctcacactg agaatgtaag aactacaaac aaaatttcta ttaaattaaa ttttgtgtct 5880
c 5881

<210> SEQ ID NO 3
<211> LENGTH: 11
<212> TYPE: PRT
<213> ORGANISM: Artificial Sequence
<220> FEATURE:
<223> OTHER INFORMATION: synthetic oligopeptide
<220> FEATURE:
<223> OTHER INFORMATION: N-terminus amino acid sequence of GenWay Biotech recombinant human calreticulin

<400> SEQUENCE: 3

Met His His His His His His His His Glu Phe
1 5 10

<210> SEQ ID NO 4
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<223> OTHER INFORMATION: N-terminus amino acid sequence of recombinant rabbit and human calreticulin including five additional amino acids and a his tag; Michalak 5 CRT + tag

<400> SEQUENCE: 4

Met His His His His His His His His Thr Met Glu Leu Glu
1 5 10

<210> SEQ ID NO 5
<211> LENGTH: 32
<212> TYPE: PRT
<213> ORGANISM: Artificial Sequence
<220> FEATURE:
<223> OTHER INFORMATION: synthetic oligopeptide
<220> FEATURE:
<223> OTHER INFORMATION: N-terminus amino acid sequence of recombinant rabbit and human calreticulin including 23 additional amino acids and a his tag; Michalak 23 CRT +tag

<400> SEQUENCE: 5

Met His His His His His His His His Met Lys Lys Leu Leu Phe Ala
1 5 10 15

Ile Pro Leu Val Val Pro Phe Tyr Ser His Ser Thr Met Glu Leu Glu
20 25 30

<210> SEQ ID NO 6
<211> LENGTH: 396
<212> TYPE: PRT
<213> ORGANISM: Cannis Familiaris

<400> SEQUENCE: 6

```
Glu Pro Ala Ile Tyr Phe Lys Glu Gln Phe Leu Asp Gly Asp Gly Trp
1               5                   10                  15

Thr Asp Arg Trp Ile Glu Ser Lys His Lys Ser Asp Phe Gly Lys Phe
            20                  25                  30

Val Leu Ser Ser Gly Lys Phe Tyr Asn Asp Gln Glu Lys Asp Lys Gly
        35                  40                  45

Leu Gln Thr Ser Gln Asp Ala Arg Phe Tyr Ala Leu Ser Ala Arg Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asp Gly Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Ser Asn Ile
        275                 280                 285

Tyr Ala Tyr Glu Asn Phe Ala Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Asp Cys Val Val Ser Val Gln Ala Ala Glu Lys Gln Met
                325                 330                 335

Lys Asp Lys Gln Asp Glu Glu Gln Arg Leu Lys Glu Glu Glu Glu Asp
            340                 345                 350

Lys Lys Arg Lys Glu Glu Glu Glu Ala Asp Lys Glu Asp Glu Glu Asp
        355                 360                 365

Lys Asp Glu Asp Glu Glu Asp Glu Asp Asp Lys Glu Glu Glu Glu Glu
    370                 375                 380

Asp Asp Ala Ala Ala Gly Gln Ala Lys Asp Glu Leu
385                 390                 395
```

<210> SEQ ID NO 7
<211> LENGTH: 400
<212> TYPE: PRT

-continued

<213> ORGANISM: Leporidae Cuniculas

<400> SEQUENCE: 7

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Lys Lys Arg Lys Glu Glu Glu Glu Ala Glu Asp Lys
        355                 360                 365

Glu Asp Asp Glu Asp Lys Asp Glu Asp Glu Glu Asp Glu Glu Asp Lys
    370                 375                 380

Glu Glu Asp Glu Glu Glu Asp Val Pro Gly Gln Ala Lys Asp Glu Leu
385                 390                 395                 400
```

-continued

```
<210> SEQ ID NO 8
<211> LENGTH: 5
<212> TYPE: PRT
<213> ORGANISM: Artificial Sequence
<220> FEATURE:
<223> OTHER INFORMATION: synthetic oligopeptide
<220> FEATURE:
<223> OTHER INFORMATION: N-terminus amino acid sequence of recombinant
      rabbit and human calreticulin including 5 additional
      amino acids; Michalak 5CRT

<400> SEQUENCE: 8

Thr Met Glu Leu Glu
1               5


<210> SEQ ID NO 9
<211> LENGTH: 23
<212> TYPE: PRT
<213> ORGANISM: Artificial Sequence
<220> FEATURE:
<223> OTHER INFORMATION: synthetic oligopeptide
<220> FEATURE:
<223> OTHER INFORMATION: N-terminus amino acid sequence of recombinant
      rabbit and human calreticulin including 23 additional amino acids;
      Michalak 23 CRT

<400> SEQUENCE: 9

Met Lys Lys Leu Leu Phe Ala Ile Pro Leu Val Val Pro Phe Tyr Ser
1               5                   10                  15

His Ser Thr Met Glu Leu Glu
            20
```